US00RE51039E

(19) United States
(12) Reissued Patent
Wang et al.

(10) Patent Number: US RE51,039 E
(45) Date of Reissued Patent: Sep. 22, 2026

(54) CRYSTAL OF BENZOFURAN DERIVATIVE FREE BASE AND PREPARATION METHOD

(71) Applicant: JIANGSU HENGRUI MEDICINE CO., LTD., Lianyungang (CN)

(72) Inventors: Likun Wang, Lianyungang (CN); Zhenxing Du, Lianyungang (CN); Qiyun Shao, Lianyungang (CN); Chao Xu, Lianyungang (CN)

(73) Assignee: Jiangsu Hengrui Medicine Co., LTD., Lianyungang (CN)

(21) Appl. No.: 18/350,653

(22) Filed: Jul. 11, 2023

Related U.S. Patent Documents

Reissue of:
(64) Patent No.: 11,155,537
Issued: Oct. 26, 2021
Appl. No.: 16/612,168
PCT Filed: May 17, 2018
PCT No.: PCT/CN2018/087272
§ 371 (c)(1),
(2) Date: Nov. 8, 2019
PCT Pub. No.: WO2018/210302
PCT Pub. Date: Nov. 22, 2018

(30) Foreign Application Priority Data

May 18, 2017 (CN) ..... 201710350574.5

(51) Int. Cl.
*C07D 405/14* (2006.01)
*A61K 31/4545* (2006.01)

(52) U.S. Cl.
CPC ..... *C07D 405/14* (2013.01); *A61K 31/4545* (2013.01)

(58) Field of Classification Search
CPC ..... C07D 405/14; A61K 31/4545
See application file for complete search history.

(56) References Cited

U.S. PATENT DOCUMENTS

| | | | |
|---|---|---|---|
| 3,236,625 | A | 2/1966 | Klein et al. |
| 5,344,968 | A | 9/1994 | Lilitkarntakul et al. |
| 6,211,203 | B1 | 4/2001 | Amschler |
| 6,331,556 | B2 | 12/2001 | Dyke et al. |
| 7,057,067 | B2 | 6/2006 | Kodama et al. |
| 8,030,529 | B2 | 10/2011 | Wang et al. |
| 8,846,935 | B2 | 9/2014 | Duquenne et al. |
| 9,018,382 | B2 | 4/2015 | Duquenne et al. |
| 9,730,925 | B2 | 8/2017 | Creasy et al. |
| 10,017,500 | B2 | 7/2018 | Kanno et al. |
| 10,759,787 | B2 * | 9/2020 | Lu ..... A61P 35/00 |
| 11,059,811 | B2 | 7/2021 | Lu et al. |
| 11,065,239 | B2 | 7/2021 | Ma et al. |
| 11,155,537 | B2 | 10/2021 | Creasy et al. |
| 11,390,614 | B2 | 7/2022 | Lu et al. |
| 2002/0128290 | A1 | 9/2002 | Ohshima et al. |
| 2003/0181759 | A1 | 9/2003 | Kodama et al. |
| 2004/0034047 | A1 | 2/2004 | Burri et al. |
| 2009/0131688 | A1 | 5/2009 | Burgos et al. |
| 2013/0053383 | A1 | 2/2013 | Duquenne et al. |
| 2014/0350013 | A1 | 11/2014 | Duquenne et al. |
| 2015/0065483 | A1 | 3/2015 | Kuntz et al. |
| 2016/0022684 | A1 | 1/2016 | Kuo et al. |
| 2018/0282313 | A1 | 10/2018 | Kanno et al. |
| 2018/0327394 | A1 | 11/2018 | Lu et al. |

(Continued)

FOREIGN PATENT DOCUMENTS

| | | | |
|---|---|---|---|
| CN | 1426388 | A | 6/2003 |
| CN | 101434582 | A | 5/2009 |

(Continued)

OTHER PUBLICATIONS

Abdel-Wahab, Omar, et al. "ASXL1 Mutations Promote Myeloid Transformation through Loss of PRC2-Mediated Gene Repression." Cancer Cell, vol. 22, No. 2, Aug. 2012, pp. 180-193. Crossref, https://doi.org/10.1016/j.ccr.2012.06.032.

Abdulla, Maysaa, et al. "Cell-of-origin Determined by Both Gene Expression Profiling and Immunohistochemistry Is the Strongest Predictor of Survival in Patients with Diffuse Large B-cell Lymphoma." American Journal of Hematology, vol. 95, No. 1, Nov. 2019, pp. 57-67. Portico, Crossref, https://doi.org/10.1002/ajh.25666.

Abrisqueta, Pau. "New Insights into First-Line Therapy in Diffuse Large B-Cell Lymphoma: Are We Improving Outcomes?" Journal of Clinical Medicine, vol. 13, No. 7, Mar. 2024, p. 1929. Crossref, https://doi.org/10.3390/jcm13071929.

(Continued)

*Primary Examiner* — Alan D Diamond
(74) *Attorney, Agent, or Firm* — Goodwin Procter LLP

(57) ABSTRACT

This application describes a crystal of a benzofuran derivative free base and a preparation method. Specifically, this application describes crystal A, crystal B, crystal C, and crystal D of N-((4,6-dimethyl-2-carbonyl-1,2-dihydropyridin-3-yl)methyl)-5-ethyl-6-(ethyl(tetrahydro-2H-pyran)4-yl)amino)-2-(piperidin-1-ylmethyl)benzofuran-4-carboxamide and a preparation method for the crystals. The crystals of the compound of formula (I) have great crystal stability and provides improved uses in clinical treatment.

(I)

128 Claims, 17 Drawing Sheets

(56) References Cited

U.S. PATENT DOCUMENTS

| | | | |
|---|---|---|---|
| 2020/0262813 | A1 | 8/2020 | Zhou et al. |
| 2021/0309630 | A1 | 10/2021 | Mahajan et al. |
| 2022/0127568 | A1 | 4/2022 | Mclean et al. |
| 2022/0192984 | A1 | 6/2022 | Mclean et al. |
| 2022/0281872 | A1 | 9/2022 | Jin et al. |
| 2024/0325371 | A1 | 10/2024 | Zhang et al. |
| 2025/0092026 | A1 | 3/2025 | Chen et al. |

FOREIGN PATENT DOCUMENTS

| | | | |
|---|---|---|---|
| CN | 103987842 | A | 8/2014 |
| CN | 110179796 | A | 8/2019 |
| CN | 110590559 | A | 12/2019 |
| CN | 112007162 | A | 12/2020 |
| CN | 112870365 | A | 6/2021 |
| CN | 112870366 | A | 6/2021 |
| CN | 112870367 | A | 6/2021 |
| CN | 110563590 | B | 3/2022 |
| CN | 114456156 | A | 5/2022 |
| CN | 110483222 | B | 6/2022 |
| CN | 110498745 | B | 6/2022 |
| CN | 118084881 | A | 5/2024 |
| CN | 113649053 | B | 6/2024 |
| EP | 1848678 | B1 | 7/2015 |
| EP | 3378859 | B1 | 10/2019 |
| EP | 3626715 | A1 | 3/2020 |
| JP | 2011512341 | A | 4/2011 |
| JP | 6828229 | B2 | 2/2021 |
| WO | WO-2008/117241 | A2 | 10/2008 |
| WO | 2011/140325 | A1 | 11/2011 |
| WO | 2012/005805 | A1 | 1/2012 |
| WO | 2012/050532 | A1 | 4/2012 |
| WO | WO-2012061602 | A1 | 5/2012 |
| WO | 2012/118812 | A2 | 9/2012 |
| WO | 2012/142504 | A1 | 10/2012 |
| WO | 2012/142513 | A1 | 10/2012 |
| WO | 2013/039988 | A1 | 3/2013 |
| WO | 2013/049770 | A2 | 4/2013 |
| WO | 2013/067300 | A1 | 5/2013 |
| WO | WO-2013173441 | A2 | 11/2013 |
| WO | WO-2014062732 | A1 | 4/2014 |
| WO | 2014/097041 | A1 | 6/2014 |
| WO | WO-2014166820 | A1 | 10/2014 |
| WO | WO-2014168975 | A1 | 10/2014 |
| WO | WO-2014177982 | A1 | 11/2014 |
| WO | 2015/141616 | A1 | 9/2015 |
| WO | WO-2015146159 | A1 | 10/2015 |
| WO | WO-2016007185 | A1 | 1/2016 |
| WO | WO-2016073903 | A1 | 5/2016 |
| WO | WO-2016201328 | A1 | 12/2016 |
| WO | 2017/084494 | A1 | 5/2017 |
| WO | WO-2017073335 | A1 | 5/2017 |
| WO | WO-2018086589 | A1 | 5/2018 |
| WO | WO-2018133795 | A1 | 7/2018 |
| WO | WO-2018210296 | A1 | 11/2018 |
| WO | WO-2018210302 | A1 | 11/2018 |
| WO | WO-2019091450 | A1 | 5/2019 |
| WO | WO-2020063863 | A1 | 4/2020 |
| WO | WO-2020163813 | A1 | 8/2020 |
| WO | WO-2020163814 | A1 | 8/2020 |
| WO | WO-2020/190754 | A1 | 9/2020 |
| WO | WO-2020192652 | A1 | 10/2020 |
| WO | WO-2020210388 | A1 | 10/2020 |
| WO | WO-2020224607 | A1 | 11/2020 |
| WO | WO-2020228591 | A1 | 11/2020 |
| WO | WO-2021035194 | A1 | 2/2021 |
| WO | WO-2021063331 | A1 | 4/2021 |
| WO | WO-2021063332 | A1 | 4/2021 |
| WO | WO-2021063340 | A1 | 4/2021 |
| WO | WO-2021074620 | A1 | 4/2021 |
| WO | WO-2021142230 | A1 | 7/2021 |
| WO | WO-2021209520 | A1 | 10/2021 |
| WO | WO-2022058405 | A2 | 3/2022 |
| WO | WO-2022087230 | A1 | 4/2022 |
| WO | WO-2022179584 | A1 | 9/2022 |
| WO | WO-2022212746 | A1 | 10/2022 |
| WO | WO-2022212748 | A1 | 10/2022 |
| WO | WO-2022232435 | A1 | 11/2022 |
| WO | WO-2023011533 | A1 | 2/2023 |
| WO | WO-2023015164 | A1 | 2/2023 |
| WO | WO-2023025856 | A1 | 3/2023 |
| WO | WO-2023030299 | A1 | 3/2023 |
| WO | WO-2023055885 | A2 | 4/2023 |
| WO | WO-2023061446 | A1 | 4/2023 |
| WO | WO-2023061467 | A1 | 4/2023 |
| WO | WO-2023108563 | A1 | 6/2023 |
| WO | WO-2023114460 | A1 | 6/2023 |
| WO | WO-2023209591 | A1 | 11/2023 |
| WO | WO-2023212504 | A1 | 11/2023 |
| WO | WO-2023215449 | A1 | 11/2023 |
| WO | WO-2023215471 | A1 | 11/2023 |
| WO | WO-2023215482 | A1 | 11/2023 |
| WO | WO-2023240038 | A1 | 12/2023 |
| WO | WO-2023244917 | A1 | 12/2023 |
| WO | WO-2023244918 | A1 | 12/2023 |
| WO | WO-2023249714 | A1 | 12/2023 |
| WO | WO-2024015566 | A1 | 1/2024 |

OTHER PUBLICATIONS

Adams, Scott V., et al. "Racial Patterns of Peripheral T-Cell Lymphoma Incidence and Survival in the United States." Journal of Clinical Oncology, vol. 34, No. 9, Mar. 2016, pp. 963-971. Crossref, https://doi.org/10.1200/jco.2015.63.5540.

Al Khatib, MHD Ouis, et al. "Benefits and Challenges of Inhibiting EZH2 in Malignant Pleural Mesothelioma." Cancers, vol. 15, No. 5, Feb. 2023, p. 1537. Crossref, https://doi.org/10.3390/cancers15051537.

Alaggio, Rita, et al. "The 5th Edition of the World Health Organization Classification of Haematolymphoid Tumours: Lymphoid Neoplasms." Leukemia, vol. 36, No. 7, Jun. 2022, pp. 1720-1748. Crossref, https://doi.org/10.1038/s41375-022-01620-2.

Al-Hasani, Keith, et al. "EZH2 Inhibitors Promote ß-like Cell Regeneration in Young and Adult Type 1 Diabetes Donors." Signal Transduction and Targeted Therapy, vol. 9, No. 1, Jan. 2024. Crossref, https://doi.org/10.1038/s41392-023-01707-x.

Alldredge, Jill K., and Ramez N. Eskander. "EZH2 Inhibition in ARID1A Mutated Clear Cell and Endometrioid Ovarian and Endometrioid Endometrial Cancers." Gynecologic Oncology Research and Practice, vol. 4, No. 1, Oct. 2017. Crossref, https://doi.org/10.1186/s40661-017-0052-y.

Amengual, J. E., et al. "ETCTN P10500: Phase 1/Expansion Study of Tazemetostat Plus Belinostat for the Treatment of Relapsed or Refractory Lymphoma." Hematological Oncology, vol. 41, No. S2, Jun. 2023, pp. 833-834. Portico, Crossref, https://doi.org/10.1002/hon.3166_ot14.

An, Ran, et al. "EZH1/2 as Targets for Cancer Therapy." Cancer Gene Therapy, vol. 30, No. 2, Nov. 2022, pp. 221-235. Crossref, https://doi.org/10.1038/s41417-022-00555-1.

Archer, Clive B., et al. "Management of Cutaneous T-Cell Lymphoma." Clinical Medicine, vol. 12, No. 2, Apr. 2012, pp. 160-164. Crossref, https://doi.org/10.7861/clinmedicine.12-2-160.

Argon, Evren Kocabas, et al. "Abstract CT170: Phase 1 Study to Characterize the Pharmacokinetics and Safety of Tazemetostat in b-Cell Lymphomas or Advanced Solid Tumors." Cancer Research, vol. 80, No. 16_Supplement, Aug. 2020, pp. CT170-CT170. Crossref, https://doi.org/10.1158/1538-7445.am2020-ct170.

Atallah-Yunes, Suheil Albert, et al. "Epigenetic Aberrations and Targets in Peripheral T-Cell Lymphoma." Clinical Lymphoma Myeloma and Leukemia, vol. 22, No. 9, Sep. 2022, pp. 659-665. Crossref, https://doi.org/10.1016/j.clml.2022.04.015.

Bagnato, Gianmarco, et al. "Successful Bridging to Allogeneic Transplantation With Valemetostat in Two Refractory/Relapsed Peripheral T-Cell Lymphoma Patients." Mediterranean Journal of Hematology and Infectious Diseases, vol. 16, No. 1, Jan. 2024, p. e2024004. Crossref, https://doi.org/10.4084/mjhid.2024.004.

Barghout, Samir H., et al. "Chemical Biology and Pharmacology of Histone Lysine Methylation Inhibitors." Biochimica et Biophysica

(56) References Cited

OTHER PUBLICATIONS

Acta (BBA)—Gene Regulatory Mechanisms, vol. 1865, No. 6, Aug. 2022, p. 194840. Crossref, https://doi.org/10.1016/j.bbagrm.2022.194840.

Bashore, Frances M., et al. "Protac Linkerology Leads to an Optimized Bivalent Chemical Degrader of Polycomb Repressive Complex 2 (PRC2) Components." ACS Chemical Biology, vol. 18, No. 3, Mar. 2023, pp. 494-507. Crossref, https://doi.org/10.1021/acschembio.2c00804.

Batlevi, C. L., et al. "Characteristics of Patients Achieving Complete or Partial Response (CR/PR) With Tazemetostat (Taz) in Wild-Type Relapsed/Refractory (R/R) Follicular Lymphoma (FL)." Hematological Oncology, vol. 39, No. S2, Jun. 2021. Portico, Crossref, https://doi.org/10.1002/hon.21_2880.

Batlevi, Connie Lee, et al. "Updated Interim Analysis of the Randomized Phase 1b/3 Study of Tazemetostat in Combination with Lenalidomide and Rituximab in Patients with Relapsed/Refractory Follicular Lymphoma." Journal of Clinical Oncology, vol. 40, No. 16_suppl, Jun. 2022, pp. 7572-7572. Crossref, https://doi.org/10.1200/jco.2022.40.16_suppl.7572.

Béguelin, Wendy, et al. "EZH2 and BCL6 Cooperate to Assemble CBX8-BCOR Complex to Repress Bivalent Promoters, Mediate Germinal Center Formation and Lymphomagenesis." Cancer Cell, vol. 30, No. 2, Aug. 2016, pp. 197-213. Crossref, https://doi.org/10.1016/j.ccell.2016.07.006.

Béguelin, Wendy, et al. "EZH2 Enables Germinal Centre Formation through Epigenetic Silencing of CDKN1A and an Rb-E2F1 Feedback Loop." Nature Communications, vol. 8, No. 1, Oct. 2017. Crossref, https://doi.org/10.1038/s41467-017-01029-x.

Béguelin, Wendy, et al. "EZH2 Is Required for Germinal Center Formation and Somatic EZH2 Mutations Promote Lymphoid Transformation." Cancer Cell, vol. 23, No. 5, May 2013, pp. 677-692. Crossref, https://doi.org/10.1016/j.ccr.2013.04.011.

Béguelin, Wendy, et al. "Mutant EZH2 Induces a Pre-Malignant Lymphoma Niche by Reprogramming the Immune Response." Cancer Cell, vol. 37, No. 5, May 2020, pp. 655-673.e11. Crossref, https://doi.org/10.1016/j.ccell.2020.04.004.

Bekric, Dino, et al. "Evaluation of Tazemetostat as a Therapeutically Relevant Substance in Biliary Tract Cancer." Cancers, vol. 15, No. 5, Mar. 2023, p. 1569. Crossref, https://doi.org/10.3390/cancers15051569.

Bellas, Carmen, et al. "Immunohistochemical and Molecular Characteristics with Prognostic Significance in Diffuse Large B-Cell Lymphoma." PloS One, edited by Syed A. Aziz, vol. 9, No. 6, Jun. 2014, p. e98169. Crossref, https://doi.org/10.1371/journal.pone.0098169.

Bellei, Monica, et al. "The Outcome of Peripheral T-Cell Lymphoma Patients Failing First-Line Therapy: A Report from the Prospective, International T-Cell Project." Haematologica, vol. 103, No. 7, Mar. 2018, pp. 1191-1197. Crossref, https://doi.org/10.3324/haematol.2017.186577.

Benevolo Savelli, Corrado, et al. "Advances in Hodgkin Lymphoma Treatment: From Molecular Biology to Clinical Practice." Cancers, vol. 16, No. 10, May 2024, p. 1830. Crossref, https://doi.org/10.3390/cancers16101830.

Blakemore, S. J., et al. "Preliminary Evidence of a Molecular Predictor of Tazemetostat Response, Beyond EZH2 Mutation, in NHL Patients via Characterization of Archive Tumor and Circulating Tumor DNA." Hematological Oncology, vol. 35, No. S2, Jun. 2017, pp. 159-160. Portico, Crossref, https://doi.org/10.1002/hon.2438_14.

Bosisio, Francesca M., and Lorenzo Cerroni. "Expression of T-Follicular Helper Markers in Sequential Biopsies of Progressive Mycosis Fungoides and Other Primary Cutaneous T-Cell Lymphomas." The American Journal of Dermatopathology, vol. 37, No. 2, Feb. 2015, pp. 115-121. Crossref, https://doi.org/10.1097/dad.0000000000000258.

Boss, Isaac W., and Ari M. Melnick. "VII. Are Lymphomas Driven by Epigenetic Lesions?" Hematological Oncology, vol. 33, No. S1, Jun. 2015, pp. 42-45. Portico, Crossref, https://doi.org/10.1002/hon.2215.

Broccoli, Alessandro, et al. "Peripheral T-Cell Lymphomas: Focusing on Novel Agents in Relapsed and Refractory Disease." Cancer Treatment Reviews, vol. 60, Nov. 2017, pp. 120-129. Crossref, https://doi.org/10.1016/j.ctrv.2017.09.002.

Buteyn, Nathaniel J., et al. EZH2-Driven Immune Evasion Defines High-Risk Pediatric AML with t(16;21) FUS::ERG Gene Fusion. May 2024. Crossref, https://doi.org/10.1101/2024.05.14.594150.

Caganova, Marieta, et al. "Germinal Center Dysregulation by Histone Methyltransferase EZH2 Promotes Lymphomagenesis." Journal of Clinical Investigation, vol. 123, No. 12, Nov. 2013, pp. 5009-5022. Crossref, https://doi.org/10.1172/jci70626.

Cai, Jin, et al. "Design, Synthesis and Activity Evaluation of Quinolinone Derivatives as EZH2 Inhibitors." Bioorganic & Medicinal Chemistry Letters, vol. 105, Jun. 2024, p. 129726. Crossref, https://doi.org/10.1016/j.bmcl.2024.129726.

Cai, Zhuo Ran, et al. "Incidence Trends of Primary Cutaneous T-Cell Lymphoma in the US From 2000 to 2018." JAMA Oncology, vol. 8, No. 11, Nov. 2022, p. 1690. Crossref, https://doi.org/10.1001/jamaoncol.2022.3236.

Campo, Elias, et al. "The International Consensus Classification of Mature Lymphoid Neoplasms: A Report from the Clinical Advisory Committee." Blood, vol. 140, No. 11, Sep. 2022, pp. 1229-1253. Crossref, https://doi.org/10.1182/blood.2022015851.

Campolo, Michela, et al. "EZH2 Inhibition to Counteract Oral Cancer Progression through Wnt/β-Catenin Pathway Modulation." Pharmaceuticals, vol. 17, No. 8, Aug. 2024, p. 1102. Crossref, https://doi.org/10.3390/ph17081102.

Cao, Ruolin, et al. "Recent Advances in Enhancer of Zeste Homolog 2 Inhibitors: Structural Insights and Therapeutic Applications." Bioorganic Chemistry, vol. 154, Jan. 2025, p. 108070. Crossref, https://doi.org/10.1016/j.bioorg.2024.108070.

Chang, Esther Wei Yin, et al. "Novel Clinical Risk Stratification and Treatment Strategies in Relapsed/Refractory Peripheral T-Cell Lymphoma." Journal of Hematology & Oncology, vol. 17, No. 1, Jun. 2024. Crossref, https://doi.org/10.1186/s13045-024-01560-7.

Chatterjee, Shankha S., et al. "Increased Translation Driven by Non-Canonical EZH2 Creates a Synthetic Vulnerability in Enzalutamide-Resistant Prostate Cancer." Nature Communications, vol. 15, No. 1, Nov. 2024. Crossref, https://doi.org/10.1038/s41467-024-53874-2.

Chebly, Alain, et al. "Diagnosis and Treatment of Lymphomas in the Era of Epigenetics." Blood Reviews, vol. 48, Jul. 2021, p. 100782. Crossref, https://doi.org/10.1016/j.blre.2020.100782.

Chen, Lingli, et al. "Compound AC1Q3QWB Upregulates CDKN1A and SOX17 by Interrupting the HOTAIR—EZH2 Interaction and Enhances the Efficacy of Tazemetostat in Endometrial Cancer." Cancer Letters, vol. 578, Dec. 2023, p. 216445. Crossref, https://doi.org/10.1016/j.canlet.2023.216445.

Chen, Yue, et al. "Five Trends of China's Pharmaceutical Industry in 2022." Acta Pharmaceutica Sinica B, vol. 13, No. 6, Jun. 2023, pp. 2812-2814. Crossref, https://doi.org/10.1016/j.apsb.2023.04.004.

Cheng, Yuxi, et al. "Polycomb Repressive Complex 2 and Its Core Component EZH2: Potential Targeted Therapeutic Strategies for Head and Neck Squamous Cell Carcinoma." Clinical Epigenetics, vol. 16, No. 1, Apr. 2024. Crossref, https://doi.org/10.1186/s13148-024-01666-2.

Cheson, Bruce D., et al. "Recommendations for Initial Evaluation, Staging, and Response Assessment of Hodgkin and Non-Hodgkin Lymphoma: The Lugano Classification." Journal of Clinical Oncology, vol. 32, No. 27, Sep. 2014, pp. 3059-3067. Crossref, https://doi.org/10.1200/jco.2013.54.8800.

Chi, Susan N., et al. "Phase I Study of Tazemetostat, an Enhancer of Zeste Homolog-2 Inhibitor, in Pediatric Pts with Relapsed/Refractory Integrase Interactor 1-Negative Tumors." Journal of Clinical Oncology, vol. 38, No. 15_suppl, May 2020, pp. 10525-10525. Crossref, https://doi.org/10.1200/jco.2020.38.15_suppl.10525.

Chi, Susan N., et al. "Tazemetostat in Patients with Tumors with Alterations in EZH2 or the SWI/SNF Complex: Results from

(56) References Cited

OTHER PUBLICATIONS

NCI-COG Pediatric Match Trial Arm C (APEC1621C)." Journal of Clinical Oncology, vol. 40, No. 16_suppl, Jun. 2022, pp. 10009-10009. Crossref, https://doi.org/10.1200/jco.2022.40.16_suppl.10009.

Chibaya, Loretah, et al. "EZH2 Inhibition Remodels the Inflammatory Senescence-Associated Secretory Phenotype to Potentiate Pancreatic Cancer Immune Surveillance." Nature Cancer, vol. 4, No. 6, May 2023, pp. 872-892. Crossref, https://doi.org/10.1038/s43018-023-00553-8.

Chu, Liping, et al. "EZH2 W113C Is a Gain-of-Function Mutation in B-Cell Lymphoma Enabling Both PRC2 Methyltransferase Activation and Tazemetostat Resistance." Journal of Biological Chemistry, vol. 299, No. 4, Apr. 2023, p. 103073. Crossref, https://doi.org/10.1016/j.jbc.2023.103073.

Collinson, Adam, et al. "Deletion of the Polycomb-Group Protein EZH2 Leads to Compromised Self-Renewal and Differentiation Defects in Human Embryonic Stem Cells." Cell Reports, vol. 17, No. 10, Dec. 2016, pp. 2700-2714. Crossref, https://doi.org/10.1016/j.celrep.2016.11.032.

Crotty, Shane. "Follicular Helper CD4 T Cells (TFH)." Annual Review of Immunology, vol. 29, No. 1, Apr. 2011, pp. 621-663. Crossref, https://doi.org/10.1146/annurev-immunol-031210-101400.

D'Amore, F., et al. "Peripheral T-Cell Lymphomas: ESMO Clinical Practice Guidelines for Diagnosis, Treatment and Follow-Up." Annals of Oncology, vol. 26, Sep. 2015, pp. v108-15. Crossref, https://doi.org/10.1093/annonc/mdv201.

De Leval, Laurence, et al. "A Practical Approach to the Modern Diagnosis and Classification of T- and NK-Cell Lymphomas." Blood, vol. 144, No. 18, Oct. 2024, pp. 1855-1872. Crossref, https://doi.org/10.1182/blood.2023021786.

Dockerill, Milly, et al. "Targeting PRC2 for the Treatment of Cancer: An Updated Patent Review (2016-2020)." Expert Opinion on Therapeutic Patents, vol. 31, No. 2, Jan. 2021, pp. 119-135. Crossref, https://doi.org/10.1080/13543776.2021.1841167.

Drescher, Charles, et al. "EZH2/EZH1 Inhibitor Tulmimetostat (CPI-0209) in Patients with Advanced Solid Tumors or Hematologic Malignancies: Preliminary Phase II Results." Journal of Clinical Oncology, vol. 41, No. 16_suppl, Jun. 2023, pp. 3094-3094. Crossref, https://doi.org/10.1200/jco.2023.41.16_suppl.3094.

Du, Jun, et al. "Comparison of Allogeneic Stem Cell Transplant and Autologous Stem Cell Transplant in Refractory or Relapsed Peripheral T-Cell Lymphoma." JAMA Network Open, vol. 4, No. 5, May 2021, p. e219807. Crossref, https://doi.org/10.1001/jamanetworkopen.2021.9807.

Duan, Ran, et al. "EZH2: A Novel Target for Cancer Treatment." Journal of Hematology & Oncology, vol. 13, No. 1, Jul. 2020. Crossref, https://doi.org/10.1186/s13045-020-00937-8.

DuCote, Tanner J., et al. "EZH2 Inhibition Promotes Tumor Immunogenicity in Lung Squamous Cell Carcinomas." Cancer Research Communications, Jan. 2024. Crossref, https://doi.org/10.1158/2767-9764.crc-23-0399.

DuCote, Tanner J., et al. EZH2 Inhibition Promotes Tumor Immunogenicity in Lung Squamous Cell Carcinomas. Jun. 2023. Crossref, https://doi.org/10.1101/2023.06.06.543919.

Dummer, Reinhard, et al. "Prospective International Multicenter Phase II Trial of Intravenous Pegylated Liposomal Doxorubicin Monochemotherapy in Patients With Stage IIB, IVA, or IVB Advanced Mycosis Fungoides: Final Results From EORTC 21012." Journal of Clinical Oncology, vol. 30, No. 33, Nov. 2012, pp. 4091-4097. Crossref, https://doi.org/10.1200/jco.2011.39.8065.

Dumont, Maëlle, et al. "Allogeneic Hematopoietic Stem Cell Transplantation in Cutaneous T-Cell Lymphomas." Cancers, vol. 12, No. 10, Oct. 2020, p. 2856. Crossref, https://doi.org/10.3390/cancers12102856.

Durand, Marie-Alice, et al. "Distinct Regulation of EZH2 and Its Repressive H3K27me3 Mark in Polyomavirus-Positive and -Negative Merkel Cell Carcinoma." Journal of Investigative Dermatology, vol. 143, No. 10, Oct. 2023, pp. 1937-1946.e7. Crossref, https://doi.org/10.1016/j.jid.2023.02.038.

Eich, Marie-Lisa, et al. "EZH2-Targeted Therapies in Cancer: Hype or a Reality." Cancer Research, vol. 80, No. 24, Dec. 2020, pp. 5449-5458. Crossref, https://doi.org/10.1158/0008-5472.can-20-2147.

Ennishi, Daisuke, et al. "Molecular and Genetic Characterization of MHC Deficiency Identifies EZH2 as Therapeutic Target for Enhancing Immune Recognition." Cancer Discovery, vol. 9, No. 4, Apr. 2019, pp. 546-563. Crossref, https://doi.org/10.1158/2159-8290.cd-18-1090.

Entezari, Maliheh, et al. "The Pharmacological and Biological Importance of EZH2 Signaling in Lung Cancer." Biomedicine & Pharmacotherapy, vol. 160, Apr. 2023, p. 114313. Crossref, https://doi.org/10.1016/j.biopha.2023.114313.

Epstein-Peterson, Zachary D., and Steven M. Horwitz. "Molecularly Targeted Therapies for Relapsed and Refractory Peripheral T-Cell Lymphomas." Seminars in Hematology, vol. 58, No. 2, Apr. 2021, pp. 78-84. Crossref, https://doi.org/10.1053/j.seminhematol.2021.02.004.

Extended European Search Report issued Feb. 4, 2021 in European Application No. 18802340.2.

Fang, Jinyong, et al. "The Epigenetic Role of EZH2 in Acute Myeloid Leukemia." PeerJ, vol. 12, Dec. 2024, p. e18656. Portico, Crossref, https://doi.org/10.7717/peerj.18656.

Fang, Minggang, et al. "EZH2 Inhibition Reactivates Epigenetically Silenced FMR1 and Normalizes Molecular and Electrophysiological Abnormalities in Fragile X Syndrome Neurons." Frontiers in Neuroscience, vol. 18, Feb. 2024. Crossref, https://doi.org/10.3389/fnins.2024.1348478.

Feldman, Andrew L., et al. "Classification and Diagnostic Evaluation of Nodal T- and NK-Cell Lymphomas." Virchows Archiv, vol. 482, No. 1, Oct. 2022, pp. 265-279. Crossref, https://doi.org/10.1007/s00428-022-03412-6.

Feng, Kaichao, et al. "Phase I Study of the Bifunctional Anti-PD-L1/TGF-BRII Agent SHR-1701 Combined with SHR2554, an EZH2 Inhibitor, in Patients with Previously Treated Advanced Lymphoma and Solid Tumors." Journal of Clinical Oncology, vol. 41, No. 16_suppl, Jun. 2023, pp. 2507-2507. Crossref, https://doi.org/10.1200/jco.2023.41.16_suppl.2507.

Fenu, Elena M., et al. "Primary Cutaneous T-follicular Helper Lymphoma." EJHaem, vol. 4, No. 4, Jul. 2023, pp. 1176-1178. Portico, Crossref, https://doi.org/10.1002/jha2.737.

Fernández-Serrano, Miranda, et al. "Histone Modifications and Their Targeting in Lymphoid Malignancies." International Journal of Molecular Sciences, vol. 23, No. 1, Dec. 2021, p. 253. Crossref, https://doi.org/10.3390/ijms23010253.

Fischetti, Irene, et al. "Combined Therapy Targeting AR and EZH2 Curbs Castration-Resistant Prostate Cancer Enhancing Anti-Tumor T-Cell Response." Epigenomics, vol. 16, No. 9, Mar. 2024, pp. 653-670. Crossref, https://doi.org/10.2217/epi-2023-0374.

Foss, Francine M., and Michael Girardi. "Mycosis Fungoides and Sezary Syndrome." Hematology/Oncology Clinics of North America, vol. 31, No. 2, Apr. 2017, pp. 297-315. Crossref, https://doi.org/10.1016/j.hoc.2016.11.008.

Francine M. Foss, et al., "A Global Phase 2 Study of Valemetostat Tosylate (Valemetostat) in Patients with Relapsed or Refractory (R/R) Peripheral T-Cell Lymphoma (PTCL), Including R/R Adult T-Cell Leukemia/Lymphoma (ATL)—Valentine-PTCL01", Blood, 138:2533-2535, (2021).

Fukae, Masato, et al. "Bayesian Sparse Regression for Exposure-Response Analyses of Efficacy and Safety Endpoints to Justify the Clinical Dose of Valemetostat for Adult T-cell Leukemia/Lymphoma." CPT: Pharmacometrics & Systems Pharmacology, vol. 13, No. 10, Aug. 2024, pp. 1655-1669. Portico, Crossref, https://doi.org/10.1002/psp4.13203.

Fukae, Masato, et al. "Population Pharmacokinetics of Total and Unbound Valemetostat and Platelet Dynamics in Healthy Volunteers and Patients with Non-Hodgkin Lymphoma." CPT: Pharmacometrics & Systems Pharmacology, vol. 13, No. 10, Jul. 2024, pp. 1641-1654. Portico, Crossref, https://doi.org/10.1002/psp4.13201.

(56) References Cited

OTHER PUBLICATIONS

Gallardo, Amador, et al. "EZH2 Represses Mesenchymal Genes and Upholds the Epithelial State of Breast Carcinoma Cells." Cell Death & Disease, vol. 15, No. 8, Aug. 2024. Crossref, https://doi.org/10.1038/s41419-024-07011-y.
Gallardo, Amador, et al. EZH2 Represses Mesenchymal Genes and Upholds the Epithelial State of Breast Carcinoma Cells. Mar. 2023. Crossref, https://doi.org/10.1101/2023.03.13.532335.
Gan, Lu, et al. "Epigenetic Regulation of Cancer Progression by EZH2: From Biological Insights to Therapeutic Potential." Biomarker Research, vol. 6, No. 1, Mar. 2018. Crossref, https://doi.org/10.1186/s40364-018-0122-2.
Garber, Ken. "Histone—Writer Cancer Drugs Enter Center Stage." Nature Biotechnology, vol. 38, No. 8, Aug. 2020, pp. 909-912. Crossref, https://doi.org/10.1038/s41587-020-0621-1.
Gardner, Eric E., et al. "Chemosensitive Relapse in Small Cell Lung Cancer Proceeds through an EZH2-SLFN11 Axis." Cancer Cell, vol. 31, No. 2, Feb. 2017, pp. 286-299. Crossref, https://doi.org/10.1016/j.ccell.2017.01.006.
Gaut, Daria, et al. "B-Cell Acute Lymphoblastic Leukemia as a Secondary Malignancy Following Diffuse Large B-Cell Lymphoma." Hematology Reports, vol. 11, No. 2, Jun. 2019, p. 8100. Crossref, https://doi.org/10.4081/hr.2019.8100.
Ghione, Paola, et al. "T Follicular Helper Phenotype Predicts Response to Histone Deacetylase Inhibitors in Relapsed/Refractory Peripheral T-Cell Lymphoma." Blood Advances, vol. 4, No. 19, Sep. 2020, pp. 4640-4647. Crossref, https://doi.org/10.1182/bloodadvances.2020002396.
Gilson, D., et al. "British Association of Dermatologists and U.K. Cutaneous Lymphoma Group Guidelines for the Management of Primary Cutaneous Lymphomas 2018." British Journal of Dermatology, vol. 180, No. 3, Dec. 2018, pp. 496-526. Portico, Crossref, https://doi.org/10.1111/bjd.17240.
Giri, Smith, et al. "Risk of Second Primary Malignancies in Patients With Follicular Lymphoma: A United States Population-Based Study." Clinical Lymphoma Myeloma and Leukemia, vol. 17, No. 9, Sep. 2017, pp. 569-574. Crossref, https://doi.org/10.1016/j.clml.2017.06.028.
Göbel, Camiel, et al. Targeting DOT1L and EZH2 Synergizes in Breaking the Germinal Center Identity of Diffuse Large B Cell Lymphoma. Jun. 2024. Crossref, https://doi.org/10.1101/2024.06.05.597556.
Gold, Sarah, and Ali Shilatifard. "Epigenetic therapies targeting histone lysine methylation: complex mechanisms and clinical challenges." The Journal of Clinical Investigation 134.20 (2024).
Gounder, Mrinal, et al. "Tazemetostat in Advanced Epithelioid Sarcoma with Loss of INI1/SMARCB1: An International, Open-Label, Phase 2 Basket Study." The Lancet Oncology, vol. 21, No. 11, Nov. 2020, pp. 1423-1432. Crossref, https://doi.org/10.1016/s1470-2045(20)30451-4.
Groß, Elisabeth, et al. "SAM-Competitive EZH2-Inhibitors Induce Platinum Resistance by EZH2-Independent Induction of ABC-Transporters." Cancers, vol. 15, No. 11, Jun. 2023, p. 3043. Crossref, https://doi.org/10.3390/cancers15113043.
Grover, Natalie S., et al. "The Optimal Management of Relapsed and Refractory Hodgkin Lymphoma: Post-Brentuximab and Checkpoint Inhibitor Failure." Hematology, vol. 2023, No. 1, Dec. 2023, pp. 510-518. Crossref, https://doi.org/10.1182/hematology.2023000450.
Guo, Chunming, et al. "Targeting the PRC2-Dependent Epigenetic Program Alleviates Urinary Tract Infections." IScience, vol. 26, No. 6, Jun. 2023, p. 106925. Crossref, https://doi.org/10.1016/j.isci.2023.106925.
Guo, Shuangping, et al. "Clinicopathological Features of Primary Diffuse Large B-cell Lymphoma of the Central Nervous System—Strong EZH2 Expression Implying Diagnostic and Therapeutic Implication." APMIS, vol. 124, No. 12, Nov. 2016, pp. 1054-1062. Portico, Crossref, https://doi.org/10.1111/apm.12623.
Guo, Yunyun, et al. "Regulation of EZH2 Protein Stability: New Mechanisms, Roles in Tumorigenesis, and Roads to the Clinic." EBioMedicine, vol. 100, Feb. 2024, p. 104972. Crossref, https://doi.org/10.1016/j.ebiom.2024.104972.
Guo, Zhirong, et al. "Design and Synthesis of Dual EZH2/BRD4 Inhibitors to Target Solid Tumors." Journal of Medicinal Chemistry, vol. 65, No. 9, May 2022, pp. 6573-6592. Crossref, https://doi.org/10.1021/acs.jmedchem.1c01876.
Hanaki, Shunsuke, and Midori Shimada. "Targeting EZH2 as Cancer Therapy." The Journal of Biochemistry, vol. 170, No. 1, Feb. 2021, pp. 1-4. Crossref, https://doi.org/10.1093/jb/mvab007.
Hara, Natsumi, and Yu Sawada. "Epigenetics of Cutaneous T-Cell Lymphomas." International Journal of Molecular Sciences, vol. 23, No. 7, Mar. 2022, p. 3538. Crossref, https://doi.org/10.3390/ijms23073538.
Hashemi, Mehrdad, et al. "EZH2 as a Potential Therapeutic Target for Gastrointestinal Cancers." Pathology—Research and Practice, vol. 253, Jan. 2024, p. 154988. Crossref, https://doi.org/10.1016/j.prp.2023.154988.
Hathuc, Vivian, and Friederike Kreisel. "Genetic Landscape of Peripheral T-Cell Lymphoma." Life, vol. 12, No. 3, Mar. 2022, p. 410. Crossref, https://doi.org/10.3390/life12030410.
Hein, Kyaw Z., et al. "Therapeutic Role of Synthetic Lethality in ARID1A-Deficient Malignancies." Journal of Immunotherapy and Precision Oncology, vol. 7, No. 1, Feb. 2024, pp. 41-52. Crossref, https://doi.org/10.36401/jipo-22-37.
Hong, Huangming, et al. "A Multicenter, Open-Label, Single-Arm, Phase Ib Clinical Trial of HH2853 in the Treatment of Patients with Relapsed and/or Refractory Peripheral T-Cell Lymphoma." Blood, vol. 142, No. Supplement 1, Nov. 2023, pp. 304-304. Crossref, https://doi.org/10.1182/blood-2023-180372.
Hong, Seong Hwi, et al. "Inhibition of EZH2 Exerts Antitumorigenic Effects in Renal Cell Carcinoma via LATS1." FEBS Open Bio, vol. 13, No. 4, Mar. 2023, pp. 724-735. Portico, Crossref, https://doi.org/10.1002/2211-5463.13579.
Honma, Daisuke, et al. "DS-3201, a Potent EZH1/2 Dual Inhibitor, Demonstrates Antitumor Activity Against Non-Hodgkin Lymphoma (NHL) Regardless of EZH2 Mutation." Blood, vol. 132, No. Supplement 1, Nov. 2018, pp. 2217-2217. Crossref, https://doi.org/10.1182/blood-2018-99-113379.
Honma, Daisuke, et al. "Novel Orally Bioavailable EZH1/2 Dual Inhibitors with Greater Antitumor Efficacy than an EZH2 Selective Inhibitor." Cancer Science, vol. 108, No. 10, Aug. 2017, pp. 2069-2078. Portico, Crossref, https://doi.org/10.1111/cas.13326.
Horwitz, Steven M., et al. "Efficacy and Safety of Valemetostat Monotherapy in Patients with Relapsed or Refractory Peripheral T-Cell Lymphomas: Primary Results of the Phase 2 VALENTINE-PTCL01 Study." Blood, vol. 142, No. Supplement 1, Nov. 2023, pp. 302-302. Crossref, https://doi.org/10.1182/blood-2023-179304.
Horwitz, Steven M., et al. "T-Cell Lymphomas, Version 2.2022, NCCN Clinical Practice Guidelines in Oncology." Journal of the National Comprehensive Cancer Network, vol. 20, No. 3, Mar. 2022, pp. 285-308. Crossref, https://doi.org/10.6004/jnccn.2022.0015.
Horwitz, Steven, et al. "Brentuximab Vedotin with Chemotherapy for CD30-Positive Peripheral T-Cell Lymphoma (ECHELON-2): A Global, Double-Blind, Randomised, Phase 3 Trial." The Lancet, vol. 393, No. 10168, Jan. 2019, pp. 229-240. Crossref, https://doi.org/10.1016/s0140-6736(18)32984-2.
Horwitz, Steven, et al. "TCL-394 Valemetostat for Patients With R/R Peripheral T-Cell Lymphomas (PTCLs): A Phase 2 VALENTINE-PTCL01 Trial." Clinical Lymphoma Myeloma and Leukemia, vol. 24, Sep. 2024, pp. S524-S525. Crossref, https://doi.org/10.1016/s2152-2650(24)01618-5.
Hou, Yingqin, and Peng Wu. "Abstract LB339: Transient EZH2 Suppression by Tazemetostat during in Vitro Expansion Maintains T Cell Stemness and Improves Adoptive T Cell Therapy." Cancer Research, vol. 84, No. 7_Supplement, Apr. 2024, pp. LB339-LB339. Crossref, https://doi.org/10.1158/1538-7445.am2024-lb339.
Hou, Yingqin, et al. Transient EZH2 Suppression by Tazemetostat duringin VitroExpansion Maintains T Cell Stemness and Improves Adoptive T Cell Therapy. Feb. 2023. Crossref, https://doi.org/10.1101/2023.02.07.527459.

(56) References Cited

OTHER PUBLICATIONS

Hristov, Alexandra C., et al. "Cutaneous T-cell Lymphomas: 2023 Update on Diagnosis, Risk-stratification, and Management." American Journal of Hematology, vol. 98, No. 1, Oct. 2022, pp. 193-209. Portico, Crossref, https://doi.org/10.1002/ajh.26760.
https://clinicaltrials.gov/study/NCT06093945, 2023.
https://clinicaltrials.gov/study/NCT06122389?term=NCT06122389&rank=1, 2024.
https://clinicaltrials.gov/study/NCT06519526?term=NCT06519526&rank=1, 2024.
https://seekingalpha.com/article/4598609-daiichi-sankyo-company-limited-dskyf-q4-2022-earnings-call-transcript, 2023.
https://www.onclive.com/view/tazemetostat-nda-receives-priority-review-in-china-for-r-r-follicular-lymphoma, 2024.
https://www.oncologypipeline.com/apexonco/ipsen-casts-doubt-pfizers-prostate-plan Jacob Plieth, Ipsen casts doubt on Pfizer's prostate plan, ApexOnco, 2024.
https://www.pharmaceutical-technology.com/news/eisai-national-cancer-center-tazemetostat/, 2023.
Hu, H., et al. "1941P Preliminary Efficacy and Safety of SHR-2554 in Advanced Epithelioid Sarcoma: A Phase II Trial." Annals of Oncology, vol. 34, Oct. 2023, p. S1042. Crossref, https://doi.org/10.1016/j.annonc.2023.09.1170.
Huang, Jiaqi, et al. "Easy or Not—The Advances of EZH2 in Regulating T Cell Development, Differentiation, and Activation in Antitumor Immunity." Frontiers in Immunology, vol. 12, Oct. 2021. Crossref, https://doi.org/10.3389/fimmu.2021.741302.
Huang, Xun, et al. "Targeting Epigenetic Crosstalk as a Therapeutic Strategy for EZH2-Aberrant Solid Tumors." Cell, vol. 175, No. 1, Sep. 2018, pp. 186-199.e19. Crossref, https://doi.org/10.1016/j.cell.2018.08.058.
Huang, Yeying, et al. EZH2 Synergizes with BRD4-NUT to Drive NUT Carcinoma Growth through Silencing of Key Tumor Suppressor Genes. Aug. 2023. Crossref, https://doi.org/10.1101/2023.08.15.553204.
International Search Report (and English translation thereof) dated Dec. 15, 2022 issued in International Application No. PCT/CN2022/125302.
International Search Report (and English translation thereof) dated Nov. 28, 2022 issued in International Application No. PCT/CN2022/115763.
Ishitsuka, K., et al. "First-in-Human Study of the EZH1 and EZH2 Dual Inhibitor Valemetostat Tosylate (DS-3201B) in Patients With Relapsed or Refractory Non-Hodgkin Lymphomas." Hematological Oncology, vol. 39, No. S2, Jun. 2021. Portico, Crossref, https://doi.org/10.1002/hon.14_2879.
Isshiki, Yusuke, and Ari Melnick. "Epigenetic Mechanisms of Therapy Resistance in Diffuse Large B Cell Lymphoma (DLBCL)." Current Cancer Drug Targets, vol. 21, No. 4, Apr. 2021, pp. 274-282. Crossref, https://doi.org/10.2174/1568009620666210106122750.
Isshiki, Yusuke, et al. "EZH2 Inhibition Enhances T Cell Immunotherapies by Inducing Lymphoma Immunogenicity and Improving T Cell Function." Cancer Cell, vol. 43, No. 1, Jan. 2025, pp. 49-68.e9. Crossref, https://doi.org/10.1016/j.ccell.2024.11.006.
Italiano, Antoine, et al. "Tazemetostat, an EZH2 Inhibitor, in Relapsed or Refractory B-Cell Non-Hodgkin Lymphoma and Advanced Solid Tumours: A First-in-Human, Open-Label, Phase 1 Study." The Lancet Oncology, vol. 19, No. 5, May 2018, pp. 649-659. Crossref, https://doi.org/10.1016/s1470-2045(18)30145-1.
Izutsu, Koji, et al. "An Open-Label, Single-Arm Phase 2 Trial of Valemetostat for Relapsed or Refractory Adult T-Cell Leukemia/Lymphoma." Blood, vol. 141, No. 10, Mar. 2023, pp. 1159-1168. Crossref, https://doi.org/10.1182/blood.2022016862.
Izutsu, Koji, et al. "Phase II Study of Tazemetostat for Relapsed or Refractory B-cell Non-Hodgkin Lymphoma with EZH2 Mutation in Japan." Cancer Science, vol. 112, No. 9, Jul. 2021, pp. 3627-3635. Portico, Crossref, https://doi.org/10.1111/cas.15040.
Izutsu, Koji, et al. "Tazemetostat for Relapsed/Refractory B-Cell Non-Hodgkin Lymphoma with EZH2 Mutation in Japan: 3-Year Follow-up for a Phase II Study." International Journal of Hematology, vol. 120, No. 5, Aug. 2024, pp. 621-630. Crossref, https://doi.org/10.1007/s12185-024-03834-9.
Izutsu, Koji, et al. "Valemetostat for Relapsed or Refractory B-Cell Lymphomas: Primary Results from a Phase 1 Trial." Blood, vol. 142, No. Supplement 1, Nov. 2023, pp. 1731-1731. Crossref, https://doi.org/10.1182/blood-2023-179301.
Jacobsen, Eric, et al. "Valemetostat for Relapsed or Refractory Peripheral T-Cell Lymphomas: Primary Results from a Phase 1 Trial." Blood, vol. 142, No. Supplement 1, Nov. 2023, pp. 303-303. Crossref, https://doi.org/10.1182/blood-2023-172512.
Jawed, Sarah I., et al. "Primary Cutaneous T-Cell Lymphoma (Mycosis Fungoides and Sézary Syndrome)." Journal of the American Academy of Dermatology, vol. 70, No. 2, Feb. 2014, pp. 205.e1-205.e16. Crossref, https://doi.org/10.1016/j.jaad.2013.07.049.
Jeon, Eun Young, et al. Inhibiting EZH2 Complements Steroid Effects in Duchenne Muscular Dystrophy. Aug. 2024. Crossref, https://doi.org/10.1101/2024.08.22.609220.
Jiang, Yanwen, et al. "The Many Layers of Epigenetic Dysfunction in B-Cell Lymphomas." Current Opinion in Hematology, vol. 23, No. 4, Jul. 2016, pp. 377-384. Crossref, https://doi.org/10.1097/moh.0000000000000249.
Jin, Cheng, et al. "EZH2 Deletion Promotes Spermatogonial Differentiation and Apoptosis." Reproduction, vol. 154, No. 5, Nov. 2017, pp. 615-625. Crossref, https://doi.org/10.1530/rep-17-0302.
Kaniskan, H. Ümit, et al. "Selective Inhibitors of Protein Methyltransferases." Journal of Medicinal Chemistry, vol. 58, No. 4, Dec. 2014, pp. 1596-1629. Crossref, https://doi.org/10.1021/jm501234a.
Kaur, Parminder, et al. "EZH2-Mediated Development of Therapeutic Resistance in Cancer." Cancer Letters, vol. 586, Apr. 2024, p. 216706. Crossref, https://doi.org/10.1016/j.canlet.2024.216706.
Kazansky, Yaniv, et al. "Overcoming Clinical Resistance to EZH2 Inhibition Using Rational Epigenetic Combination Therapy." Cancer Discovery, vol. 14, No. 6, Jun. 2024, pp. 965-981. Crossref, https://doi.org/10.1158/2159-8290.cd-23-0110.
Keam, Susan J. "Valemetostat Tosilate: First Approval." Drugs, vol. 82, No. 16, Nov. 2022, pp. 1621-1627. Crossref, https://doi.org/10.1007/s40265-022-01800-5.
Kenkre, Vaishalee P., et al. "A Phase I/II Study of Tazemetostat Combined with Abbreviated Rituximab/Bendamustine Therapy for High Tumor Burden Follicular Lymphoma in Frontline Treatment: A Big Ten Cancer Research Consortium Study." Blood, vol. 144, No. Supplement 1, Nov. 2024, pp. 4415-4415. Crossref, https://doi.org/10.1182/blood-2024-202639.
Khanna, Avinash, et al. "Design, Synthesis, and Pharmacological Evaluation of Second Generation EZH2 Inhibitors with Long Residence Time." ACS Medicinal Chemistry Letters, vol. 11, No. 6, Mar. 2020, pp. 1205-1212. Crossref, https://doi.org/10.1021/acsmedchemlett.0c00045.
Kim, Youn H., et al. "Mogamulizumab versus Vorinostat in Previously Treated Cutaneous T-Cell Lymphoma (MAVORIC): An International, Open-Label, Randomised, Controlled Phase 3 Trial." The Lancet Oncology, vol. 19, No. 9, Sep. 2018, pp. 1192-1204. Crossref, https://doi.org/10.1016/s1470-2045(18)30379-6.
Knutson, Sarah K., et al. "A Selective Inhibitor of EZH2 Blocks H3K27 Methylation and Kills Mutant Lymphoma Cells." Nature Chemical Biology, vol. 8, No. 11, Sep. 2012, pp. 890-896. Crossref, https://doi.org/10.1038/nchembio.1084.
Konze, Kyle D., et al. "An Orally Bioavailable Chemical Probe of the Lysine Methyltransferases EZH2 and EZH1." ACS Chemical Biology, vol. 8, No. 6, Apr. 2013, pp. 1324-1334. Crossref, https://doi.org/10.1021/cb400133j.
Kung, Pei-Pei, et al. "Optimization of Orally Bioavailable Enhancer of Zeste Homolog 2 (EZH2) Inhibitors Using Ligand and Property-Based Design Strategies: Identification of Development Candidate (R)-5,8-Dichloro-7-(Methoxy(Oxetan-3-Yl)Methyl)-2-((4-Methoxy-6-Methyl-2-Oxo-1,2-Dihydropyridin-3-Yl)Methyl)-3,4-Dihydroisoquinolin-1(2H)-One (PF-06821497)." Journal of Medicinal Chemistry, vol. 61, No. 3, Dec. 2017, pp. 650-665. Crossref, https://doi.org/10.1021/acs.jmedchem.7b01375.

(56) References Cited

OTHER PUBLICATIONS

Kunhong Deng, et al., "Study on pharmacokinetic interactions between SHR2554 and itraconazole in healthy subjects: A single-center, open-label phase I trial", Cancer Medicine, 12:1431-1440, (2023).
Kwok, Hui Si, et al. "Drug Addiction Unveils a Repressive Methylation Ceiling in EZH2-Mutant Lymphoma." Nature Chemical Biology, vol. 19, No. 9, Mar. 2023, pp. 1105-1115. Crossref, https://doi.org/10.1038/s41589-023-01299-1.
LaFave, Lindsay M., et al. "Loss of BAP1 Function Leads to EZH2-Dependent Transformation." Nature Medicine, vol. 21, No. 11, Oct. 2015, pp. 1344-1349. Crossref, https://doi.org/10.1038/nm.3947.
Lakhani, Nehal J., et al. "Phase 1/2 First-in-Human (FIH) Study of CPI-0209, a Novel Small Molecule Inhibitor of Enhancer of Zeste Homolog 2 (EZH2) in Patients with Advanced Tumors." Journal of Clinical Oncology, vol. 39, No. 15_suppl, May 2021, pp. 3104-3104. Crossref, https://doi.org/10.1200/jco.2021.39.15_suppl.3104.
Landman, Nick, et al. "Combination of EZH2 and ATM Inhibition in BAP1-Deficient Mesothelioma." British Journal of Cancer, vol. 130, No. 11, Mar. 2024, pp. 1855-1865. Crossref, https://doi.org/10.1038/s41416-024-02661-3.
Lanzi, Cinzia, et al. "Targeting EZH2 in SMARCB1-Deficient Sarcomas: Advances and Opportunities to Potentiate the Efficacy of EZH2 Inhibitors." Biochemical Pharmacology, vol. 215, Sep. 2023, p. 115727. Crossref, https://doi.org/10.1016/j.bcp.2023.115727.
Laribi, Kamel, et al. "Recent Advances in the Treatment of Peripheral T-Cell Lymphoma." The Oncologist, vol. 23, No. 9, Apr. 2018, pp. 1039-1053. Crossref, https://doi.org/10.1634/theoncologist.2017-0524.
Le, Meiling, et al. "Design, Synthesis, and Biological Evaluation of Potent EZH2/LSD1 Dual Inhibitors for Prostate Cancer." Journal of Medicinal Chemistry, vol. 67, No. 17, Aug. 2024, pp. 15586-15605. Crossref, https://doi.org/10.1021/acs.jmedchem.4c01250.
Li, Chen, et al. "Finding an Easy Way to Harmonize: A Review of Advances in Clinical Research and Combination Strategies of EZH2 Inhibitors." Clinical Epigenetics, vol. 13, No. 1, Mar. 2021. Crossref, https://doi.org/10.1186/s13148-021-01045-1.
Li, Fengyin, et al. "Ezh2 Programs TFH Differentiation by Integrating Phosphorylation-Dependent Activation of Bcl6 and Polycomb-Dependent Repression of P19Arf." Nature Communications, vol. 9, No. 1, Dec. 2018. Crossref, https://doi.org/10.1038/s41467-018-07853-z.
Li, Meng, and Ari M. Melnick. "An 'EZ' Epigenetic Road to Leukemia Stem Cell Metabolic Reprogramming?" Cancer Discovery, vol. 9, No. 9, Sep. 2019, pp. 1158-1160. Crossref, https://doi.org/10.1158/2159-8290.cd-19-0737.
Li, Mengjia, et al. "Stage-Specific Dual Function: EZH2 Regulates Human Erythropoiesis by Eliciting Histone and Non-Histone Methylation." Haematologica, Apr. 2023. Crossref, https://doi.org/10.3324/haematol.2022.282016.
Li, Ruoyan, et al. Cutaneous T Cell Lymphoma Atlas Reveals Malignant Th2 Cells Supported by a B Cell-Rich Microenvironment. Nov. 2023. Crossref, https://doi.org/10.1101/2023.11.06.565474.
Liao, Qili, et al. "Novel Insights into Histone Lysine Methyltransferases in Cancer Therapy: From Epigenetic Regulation to Selective Drugs." Journal of Pharmaceutical Analysis, vol. 13, No. 2, Feb. 2023, pp. 127-141. Crossref, https://doi.org/10.1016/j.jpha.2022.11.009.
Lin, Jiunn-Miin, et al. "BCL-6 Promotes the Methylation of miR-34a by Recruiting EZH2 and Upregulating CTRP9 to Protect Ischemic Myocardial Injury." BioFactors, vol. 47, No. 3, Jan. 2021, pp. 386-402. Portico, Crossref, https://doi.org/10.1002/biof.1704.
Lin, Xiao-Hu, et al. "The Heightened Importance of EZH2 in Cancer Immunotherapy." Cancer Screening and Prevention, vol. 000, No. 000, Jun. 2023, pp. 000-000. Crossref, https://doi.org/10.14218/csp.2023.00006.
Link, Brian K., et al. "Rates and Outcomes of Follicular Lymphoma Transformation in the Immunochemotherapy Era: A Report From the University of Iowa/Mayo Clinic Specialized Program of Research Excellence Molecular Epidemiology Resource." Journal of Clinical Oncology, vol. 31, No. 26, Sep. 2013, pp. 3272-3278. Crossref, https://doi.org/10.1200/jco.2012.48.3990.
Liu, Dongdong, et al. "BMP-ACVR1 Axis Is Critical for Efficacy of PRC2 Inhibitors in B-Cell Lymphoma." Advanced Science, vol. 11, No. 12, Jan. 2024. Portico, Crossref, https://doi.org/10.1002/advs.202306499.
Liu, Jiaxin, et al. "The Status and Prospects of Epigenetics in the Treatment of Lymphoma." Frontiers in Oncology, vol. 12, Apr. 2022. Crossref, https://doi.org/10.3389/fonc.2022.874645.
Liu, Linshan, et al. "Ezh2 Promotes Mammary Tumor Initiation through Epigenetic Regulation of the Wnt and MTORC1 Signaling Pathways." Proceedings of the National Academy of Sciences, vol. 120, No. 33, Aug. 2023. Crossref, https://doi.org/10.1073/pnas.2303010120.
Liu, Shuo, et al. "Epidemiological Characteristics of Peripheral T-Cell Lymphoma: A Population-Based Study." Frontiers in Oncology, vol. 12, Jul. 2022. Crossref, https://doi.org/10.3389/fonc.2022.863269.
Liu, Yuankai, and Qiong Yang. "The Roles of EZH2 in Cancer and Its Inhibitors." Medical Oncology, vol. 40, No. 6, May 2023. Crossref, https://doi.org/10.1007/s12032-023-02025-6.
Loi, Patrick, et al. "Epigenetic and Oncogenic Inhibitors Cooperatively Drive Differentiation and Kill KRAS-Mutant Colorectal Cancers." Cancer Discovery, vol. 14, No. 12, Aug. 2024, pp. 2430-2449. Crossref, https://doi.org/10.1158/2159-8290.cd-23-0866.
Lu, Biao, et al. "Discovery of EBI-2511: A Highly Potent and Orally Active EZH2 Inhibitor for the Treatment of Non-Hodgkin's Lymphoma." ACS Medicinal Chemistry Letters, vol. 9, No. 2, Feb. 2018, pp. 98-102. Crossref, https://doi.org/10.1021/acsmedchemlett.7b00437.
Luan, Yunpeng, et al. "Therapeutic Challenges in Peripheral T-Cell Lymphoma." Molecular Cancer, vol. 23, No. 1, Jan. 2024. Crossref, https://doi.org/10.1186/s12943-023-01904-w.
Lund, K., et al. "EZH2 in Normal and Malignant Hematopoiesis." Leukemia, vol. 28, No. 1, Oct. 2013, pp. 44-49. Crossref, https://doi.org/10.1038/leu.2013.288.
Ma, Anqi, et al. "Discovery of a First-in-Class EZH2 Selective Degrader." Nature Chemical Biology, vol. 16, No. 2, Dec. 2019, pp. 214-222. Crossref, https://doi.org/10.1038/s41589-019-0421-4.
Ma, Helen, et al. "The Peripheral T-Cell Lymphomas: An Unusual Path to Cure." The Lancet Haematology, vol. 7, No. 10, Oct. 2020, pp. e765-e771. Crossref, https://doi.org/10.1016/s2352-3026(20)30207-6.
Ma, Zetao, et al. "Novel Insights of EZH2-Mediated Epigenetic Modifications in Degenerative Musculoskeletal Diseases." Ageing Research Reviews, vol. 90, Sep. 2023, p. 102034. Crossref, https://doi.org/10.1016/j.arr.2023.102034.
Marchi, Enrica, and Owen A. O'Connor. "The Rapidly Changing Landscape in Mature T-cell Lymphoma (MTCL) Biology and Management." CA: A Cancer Journal for Clinicians, vol. 70, No. 1, Dec. 2019, pp. 47-70. Portico, Crossref, https://doi.org/10.3322/caac.21589.
Martin, M. Cynthia, et al. "Small Molecule Approaches for Targeting the Polycomb Repressive Complex 2 (PRC2) in Cancer." Journal of Medicinal Chemistry, vol. 63, No. 24, Dec. 2020, pp. 15344-15370. Crossref, https://doi.org/10.1021/acs.jmedchem.0c01344.
Maruyama, Dai, et al. "Valemetostat Monotherapy in Patients With Relapsed/Refractory Non-Hodgkin Lymphomas: Primary Results From a Phase 1 Trial." Clinical Lymphoma Myeloma and Leukemia, vol. 24, Sep. 2024, p. S229. Crossref, <https://doi.org/10.1016/s2152-2650(24)00908-x.>.
Maruyama, Dai, et al. "TCL-391 Valemetostat Monotherapy in Patients With Relapsed/Refractory Non-Hodgkin Lymphomas: Primary Results From a Phase 1 Trial." Clinical Lymphoma Myeloma and Leukemia, vol. 24, Sep. 2024, pp. S523-S524. Crossref, https://doi.org/10.1016/s2152-2650(24)01617-3.
Maruyama, Dai, et al. "Valemetostat Monotherapy in Patients with Relapsed or Refractory Non-Hodgkin Lymphoma: A First-in-Human, Multicentre, Open-Label, Single-Arm, Phase 1 Study." The

(56) References Cited

OTHER PUBLICATIONS

Lancet Oncology, vol. 25, No. 12, Dec. 2024, pp. 1589-1601. Crossref, https://doi.org/10.1016/s1470-2045(24)00502-3.
Marzochi, Ludimila Leite, et al. "Use of Histone Methyltransferase Inhibitors in Cancer Treatment: A Systematic Review." European Journal of Pharmacology, vol. 944, Apr. 2023, p. 175590. Crossref, https://doi.org/10.1016/j.ejphar.2023.175590.
Maurer, Matthew J., et al. "International Assessment of Event-Free Survival at 24 Months and Subsequent Survival in Peripheral T-Cell Lymphoma." Journal of Clinical Oncology, vol. 35, No. 36, Dec. 2017, pp. 4019-4026. Crossref, https://doi.org/10.1200/jco.2017.73.8195.
McCabe, Michael T., et al. "EZH2 Inhibition as a Therapeutic Strategy for Lymphoma with EZH2-Activating Mutations." Nature, vol. 492, No. 7427, Oct. 2012, pp. 108-112. Crossref, https://doi.org/10.1038/nature11606.
Mehta-Shah, Neha, and Steven M. Horwitz. "Failing Forward in Peripheral T-Cell Lymphoma." Journal of Clinical Oncology, vol. 42, No. 14, May 2024, pp. 1599-1602. Crossref, https://doi.org/10.1200/jco.23.02658.
Mehta-Shah, Neha, et al. "Prediction of Clinical Response By Phased Variants in Circulating Tumor DNA (CtDNA) in the VALENTINE-PTCL01 Trial of Patients with Relapsed or Refractory (R/R) Peripheral T-Cell Lymphoma (PTCL)." Blood, vol. 144, No. Supplement 1, Nov. 2024, pp. 4342-4342. Crossref, https://doi.org/10.1182/blood-2024-207594.
Mei, Husheng, et al. "Discovery of IHMT-337 as a Potent Irreversible EZH2 Inhibitor Targeting CDK4 Transcription for Malignancies." Signal Transduction and Targeted Therapy, vol. 8, No. 1, Jan. 2023. Crossref, https://doi.org/10.1038/s41392-022-01240-3.
Melnick, Ari. "Epigenetic Therapy Leaps Ahead with Specific Targeting of EZH2." Cancer Cell, vol. 22, No. 5, Nov. 2012, pp. 569-570. Crossref, https://doi.org/10.1016/j.ccr.2012.10.016.
Meng, Qingshu, et al. "EZH2 Directly Methylates PARP1 and Regulates Its Activity in Cancer." Science Advances, vol. 10, No. 48, Nov. 2024. Crossref, https://doi.org/10.1126/sciadv.adl2804.
Meyerson, Howard J., et al. "Follicular Center Helper T-Cell (TFH) Marker Positive Mycosis Fungoides/Sezary Syndrome." Modern Pathology, vol. 26, No. 1, Jan. 2013, pp. 32-43. Crossref, https://doi.org/10.1038/modpathol.2012.124.
Mhaidly, Rana, et al. "New Preclinical Models for Angioimmunoblastic T-Cell Lymphoma: Filling the Gap." Oncogenesis, vol. 9, No. 8, Aug. 2020. Crossref, https://doi.org/10.1038/s41389-020-00259-x.
Minson, Adrian, et al. "Targeted Agents in the Treatment of Indolent B-Cell Non-Hodgkin Lymphomas." Cancers, vol. 14, No. 5, Mar. 2022, p. 1276. Crossref, https://doi.org/10.3390/cancers14051276.
Miyashiro, Denis, and José Antonio Sanches. "Mycosis Fungoides and Sézary Syndrome: Clinical Presentation, Diagnosis, Staging, and Therapeutic Management." Frontiers in Oncology, vol. 13, Apr. 2023. Crossref, https://doi.org/10.3389/fonc.2023.1141108.
Mondejar, Rufino, et al. "Molecular Basis of Targeted Therapy in T/NK-Cell Lymphoma/Leukemia: A Comprehensive Genomic and Immunohistochemical Analysis of a Panel of 33 Cell Lines." PLOS ONE, edited by Renato Franco, vol. 12, No. 5, May 2017, p. e0177524. Crossref, https://doi.org/10.1371/journal.pone.0177524.
Montoto, Silvia, and Jude Fitzgibbon. "Transformation of Indolent B-Cell Lymphomas." Journal of Clinical Oncology, vol. 29, No. 14, May 2011, pp. 1827-1834. Crossref, https://doi.org/10.1200/jco.2010.32.7577.
Morris, Stephan W., et al. "Fusion of a Kinase Gene, ALK, to a Nucleolar Protein Gene, NPM, in Non-Hodgkin's Lymphoma." Science, vol. 263, No. 5151, Mar. 1994, pp. 1281-1284. Crossref, https://doi.org/10.1126/science.8122112.
Morschhauser, F., et al. "Interim Report From a Phase 2 Multicenter Study of Tazemetostat, an EZH2 Inhibitor, in Patients With Relapsed or Refractory B-Cell Non-Hodgkin Lymphomas." Hematological Oncology, vol. 35, No. S2, Jun. 2017, pp. 24-25. Portico, Crossref, https://doi.org/10.1002/hon.2437_3.
Morschhauser, Franck, et al. "Taking the EZ Way: Targeting Enhancer of Zeste Homolog 2 in B-Cell Lymphomas." Blood Reviews, vol. 56, Nov. 2022, p. 100988. Crossref, https://doi.org/10.1016/j.blre.2022.100988.
Morschhauser, Franck, et al. "Tazemetostat for Patients with Relapsed or Refractory Follicular Lymphoma: An Open-Label, Single-Arm, Multicentre, Phase 2 Trial." The Lancet Oncology, vol. 21, No. 11, Nov. 2020, pp. 1433-1442. Crossref, https://doi.org/10.1016/s1470-2045(20)30441-1.
Moskowitz, Alison J., et al. "Current and Upcoming Treatment Approaches to Common Subtypes of PTCL (PTCL, NOS; ALCL; and TFHs)." Blood, vol. 144, No. 18, Oct. 2024, pp. 1887-1897. Crossref, https://doi.org/10.1182/blood.2023021789.
Munakata, Wataru, et al. "Phase 1 Study of Tazemetostat in Japanese Patients with Relapsed or Refractory B-cell Lymphoma." Cancer Science, vol. 112, No. 3, Feb. 2021, pp. 1123-1131. Portico, Crossref, https://doi.org/10.1111/cas.14822.
Naina Marikar, Safiya, et al. "Pharmacological Inhibition of Human EZH2 Can Influence a Regenerative ß-like Cell Capacity with in Vitro Insulin Release in Pancreatic Ductal Cells." Clinical Epigenetics, vol. 15, No. 1, Jun. 2023. Crossref, https://doi.org/10.1186/s13148-023-01491-z.
Nakayama, Hirotaka, et al. "Validation of EZH2 Inhibitor Efficiency in Anaplastic Thyroid Carcinoma Cell Lines." Anticancer Research, vol. 43, No. 3, Feb. 2023, pp. 1073-1077. Crossref, https://doi.org/10.21873/anticanres.16252.
Nanjappa, Manjunatha K., et al. "The Histone Methyltransferase EZH2 Is Required for Normal Uterine Development and Function in Mice†." Biology of Reproduction, vol. 101, No. 2, Jun. 2019, pp. 306-317. Crossref, https://doi.org/10.1093/biolre/ioz097.
Naso, Julia R., et al. "EZH2 and POU2F3 Can Aid in the Distinction of Thymic Carcinoma from Thymoma." Cancers, vol. 15, No. 8, Apr. 2023, p. 2274. Crossref, https://doi.org/10.3390/cancers15082274.
Nastoupil, Loretta J., et al. "An Externally Controlled Trial to Indirectly Compare Tazemetostat Plus Lenalidomide and Rituximab Versus Lenalidomide and Rituximab after at Least One Prior Systemic Therapy in Patients with Refractory and Relapsed Follicular Lymphoma." Blood, vol. 142, No. Supplement 1, Nov. 2023, pp. 4410-4410. Crossref, https://doi.org/10.1182/blood-2023-181807.
Neves Filho, Eduardo Henrique, et al. "EZH2 Expression Is Dependent on MYC and TP53 Regulation in Diffuse Large B-cell Lymphoma." APMIS, vol. 128, No. 4, Feb. 2020, pp. 308-315. Portico, Crossref, https://doi.org/10.1111/apm.13029.
Ngu, Henry S., and Kerry J. Savage. "Frontline Management of Nodal Peripheral T-Cell Lymphomas." American Society of Clinical Oncology Educational Book, No. 43, May 2023. Crossref, https://doi.org/10.1200/edbk_390334.
Nizamuddin, Imran A., and Neha Mehta-Shah. "BV and beyond: How to Incorporate Novel Agents into PTCL Management." Hematology, vol. 2024, No. 1, Dec. 2024, pp. 54-61. Crossref, https://doi.org/10.1182/hematology.2024000530.
O'Brien, Eleanor, et al. "Pharmacological EZH2 Inhibition Combined with Retinoic Acid Treatment Promotes Differentiation and Apoptosis in Rhabdomyosarcoma Cells." Clinical Epigenetics, vol. 15, No. 1, Oct. 2023. Crossref, https://doi.org/10.1186/s13148-023-01583-w.
O'Donnell, Edmond, et al. Genetic and Epigenetic Characterization of Sarcoma Stem Cells Across Subtypes Identifies EZH2 as a Therapeutic Target. May 2024. Crossref, https://doi.org/10.1101/2024.05.14.594060.
Oaknin, Ana, et al. "Phase II Dose Optimization with EZH2/EZH1 Inhibitor Tulmimetostat in Patients (Pts) with Advanced Solid Tumors or Hematologic Malignancies." Journal of Clinical Oncology, vol. 42, No. 16_suppl, Jun. 2024, pp. 3097-3097. Crossref, https://doi.org/10.1200/jco.2024.42.16_suppl.3097.
Office action for Taiwan application No. 107139895 issued on Feb. 5, 2020 as well as its English Translation.
Office action for Taiwan application No. 107139895 issued on Jun. 3, 2020 as well as its English Translation.
Office action for Taiwan application No. 107139895 issued on Sep. 4, 2019 as well as its English Translation.

(56) References Cited

OTHER PUBLICATIONS

Olsen, Elise A., et al. "Primary Cutaneous Lymphoma: Recommendations for Clinical Trial Design and Staging Update from the ISCL, USCLC, and EORTC." Blood, vol. 140, No. 5, Aug. 2022, pp. 419-437. Crossref, https://doi.org/10.1182/blood.2021012057.
Ondrejka, Sarah L., et al. "Follicular Helper T-Cell Lymphomas: Disease Spectrum, Relationship with Clonal Hematopoiesis, and Mimics. A Report of the 2022 EA4HP/SH Lymphoma Workshop." Virchows Archiv, vol. 483, No. 3, Jul. 2023, pp. 349-365. Crossref, https://doi.org/10.1007/s00428-023-03607-5.
Oricchio, Elisa, et al. "Genetic and Epigenetic Inactivation of SESTRIN1 Controls MTORC1 and Response to EZH2 Inhibition in Follicular Lymphoma." Science Translational Medicine, vol. 9, No. 396, Jun. 2017. Crossref, https://doi.org/10.1126/scitranslmed.aak9969.
Ozgun, Gizem, et al. "Retinoids and EZH2 Inhibitors Cooperate to Orchestrate Anti-Oncogenic Effects on Bladder Cancer Cells." Cancer Gene Therapy, vol. 31, No. 4, Jan. 2024, pp. 537-551. Crossref, https://doi.org/10.1038/s41417-024-00725-3.
Ozgun, Gizem, et al. Retinoids and EZH2 Inhibitors Cooperate to Orchestrate Cytotoxic Effects on Bladder Cancer Cells. Apr. 2023. Crossref, https://doi.org/10.1101/2023.04.19.537500.
Palomba, M. L., et al. "Safety and Clinical Activity of Atezolizumab in Combination With Tazemetostat in Relapsed or Refractory Diffuse Large B-Cell Lymphoma: Primary Analysis of a Phase 1B Study." Hematological Oncology, vol. 37, No. S2, Jun. 2019, pp. 517-519. Portico, Crossref, https://doi.org/10.1002/hon.203_2631.
Palomba, Maria Lia, et al. "Combination of Atezolizumab and Tazemetostat in Patients With Relapsed/Refractory Diffuse Large B-Cell Lymphoma: Results From a Phase Ib Study." Clinical Lymphoma Myeloma and Leukemia, vol. 22, No. 7, Jul. 2022, pp. 504-512. Crossref, https://doi.org/10.1016/j.clml.2021.12.014.
Park, Steven I., et al. "The Role of Autologous Stem Cell Transplantation in Patients with Nodal Peripheral T-cell Lymphomas in First Complete Remission: Report from Complete, a Prospective, Multicenter Cohort Study." Cancer, vol. 125, No. 9, Jan. 2019, pp. 1507-1517. Portico, Crossref, https://doi.org/10.1002/cncr.31861.
Peng, Yu, et al. "The Role of EZH2 in Ocular Diseases: A Narrative Review." Epigenomics, vol. 15, No. 9, May 2023, pp. 557-570. Crossref, https://doi.org/10.2217/epi-2023-0147.
Prince, H. Miles, et al. "Brentuximab Vedotin or Physician's Choice in CD30-Positive Cutaneous T-Cell Lymphoma (ALCANZA): An International, Open-Label, Randomised, Phase 3, Multicentre Trial." The Lancet, vol. 390, No. 10094, Aug. 2017, pp. 555-566. Crossref, https://doi.org/10.1016/s0140-6736(17)31266-7.
Prorok, Paulina, et al. "Loss of Ezh2 Function Remodels the DNA Replication Initiation Landscape." Cell Reports, vol. 42, No. 4, Apr. 2023, p. 112280. Crossref, https://doi.org/10.1016/j.celrep.2023.112280.
Proudman, David, et al. "Tazemetostat (TAZ) in Relapsed/Refractory (R/R) Follicular Lymphoma (FL): Propensity-Score Matched Analysis of E7438-G000-101 Trial Outcomes." Journal of Clinical Oncology, vol. 39, No. 15_suppl, May 2021, pp. e18627-e18627. Crossref, https://doi.org/10.1200/jco.2021.39.15_suppl.e18627.
Qiang, Na, et al. "Alteration of the Tumor Microenvironment by Pharmacological Inhibition of EZH2 in Hepatocellular Carcinoma." International Immunopharmacology, vol. 118, May 2023, p. 110068. Crossref, https://doi.org/10.1016/j.intimp.2023.110068.
Quereux, Gaëlle, et al. "Prospective Multicenter Study of Pegylated Liposomal Doxorubicin Treatment in Patients With Advanced or Refractory Mycosis Fungoides or Sézary Syndrome." Archives of Dermatology, vol. 144, No. 6, Jun. 2008. Crossref, https://doi.org/10.1001/archderm.144.6.727.
Rai, Shinya, et al. "Abstract CT176: Phase 2 Study of Tazemetostat in Japanese Patients with Relapsed or Refractory EZH2 Mutation-Positive B-Cell Non-Hodgkin's Lymphoma." Cancer Research, vol. 81, No. 13_Supplement, Jul. 2021, pp. CT176-CT176. Crossref, https://doi.org/10.1158/1538-7445.am2021-ct176.
Richart, Laia, and Raphaël Margueron. "Drugging Histone Methyltransferases in Cancer." Current Opinion in Chemical Biology, vol. 56, Jun. 2020, pp. 51-62. Crossref, https://doi.org/10.1016/j.cbpa.2019.11.009.
Ridwansyah, Hastono, et al. "The Role of Chidamide in the Treatment of B-Cell Non-Hodgkin Lymphoma: An Updated Systematic Review." Biomolecules and Biomedicine, Mar. 2023. Crossref, https://doi.org/10.17305/bb.2023.8791.
Romero, Pierre, et al. "EZH2 Mutations in Follicular Lymphoma Distort H3K27me3 Profiles and Alter Transcriptional Responses to PRC2 Inhibition." Nature Communications, vol. 15, No. 1, Apr. 2024. Crossref, https://doi.org/10.1038/s41467-024-47701-x.
Rondeaux, Julie, et al. "Ezh2 Emerges as an Epigenetic Checkpoint Regulator during Monocyte Differentiation Limiting Cardiac Dysfunction Post-MI." Nature Communications, vol. 14, No. 1, Jul. 2023. Crossref, https://doi.org/10.1038/s41467-023-40186-0.
Sabour-Takanlou, Maryam, et al. "EZH2-associated Tumor Malignancy: A Prominent Target for Cancer Treatment." Clinical Genetics, vol. 106, No. 4, Jun. 2024, pp. 377-385. Portico, Crossref, https://doi.org/10.1111/cge.14576.
Sadaf, Hummaira, et al. "New Molecular Targets in Hodgkin and Reed-Sternberg Cells." Frontiers in Immunology, vol. 14, May 2023. Crossref, https://doi.org/10.3389/fimmu.2023.1155468.
Saleh, Khalil, et al. "Updates in the Treatment of Peripheral T-Cell Lymphomas." Journal of Experimental Pharmacology, vol. vol. 13, Jun. 2021, pp. 577-591. Crossref, https://doi.org/10.2147/jep.s262344.
Salles, Gilles, et al. "IBCL-485 A Phase III, Randomized, Double-Blind, Study of Tazemetostat or Placebo Plus Lenalidomide and Rituximab in Patients With Relapsed/Refractory Follicular Lymphoma." Clinical Lymphoma Myeloma and Leukemia, vol. 23, Sep. 2023, pp. S454-S455. Crossref, https://doi.org/10.1016/s2152-2650(23)01363-0.
Sarkozy, Clémentine, et al. "A LYSA Phase Ib Study of Tazemetostat (EPZ-6438) plus R-CHOP in Patients with Newly Diagnosed Diffuse Large B-Cell Lymphoma (DLBCL) with Poor Prognosis Features." Clinical Cancer Research, vol. 26, No. 13, Jul. 2020, pp. 3145-3153. Crossref, https://doi.org/10.1158/1078-0432.ccr-19-3741.
Satoko Morishima, et al., "First-in-Human Study of the EZH1/2 Dual Inhibitor Valemetostat in Relapsed or Refractory Non-Hodgkin Lymphoma (NHL)—Updated Results Focusing on Adult T-Cell Leukemia-Lymphoma (ATL)", Blood, Nov. 13, 2019.
Sawalha, Amr H. "BCL-6 and EZH2 Cooperate to Epigenetically Repress Anti-Inflammatory MiR-142-3p/5p in Lupus CD4+T Cells." Cellular & Molecular Immunology, vol. 18, No. 2, Sep. 2019, pp. 504-505. Crossref, https://doi.org/10.1038/s41423-019-0288-z.
Scarisbrick, Julia J., et al. "Cutaneous Lymphoma International Consortium Study of Outcome in Advanced Stages of Mycosis Fungoides and Sézary Syndrome: Effect of Specific Prognostic Markers on Survival and Development of a Prognostic Model." Journal of Clinical Oncology, vol. 33, No. 32, Nov. 2015, pp. 3766-3773. Crossref, https://doi.org/10.1200/jco.2015.61.7142.
Schade, Amy E., et al. "AKT and EZH2 Inhibitors Kill TNBCs by Hijacking Mechanisms of Involution." Nature, vol. 635, No. 8039, Oct. 2024, pp. 755-763. Crossref, https://doi.org/10.1038/s41586-024-08031-6.
Schade, Amy E., et al. "Combating Castration-Resistant Prostate Cancer by Co-Targeting the Epigenetic Regulators EZH2 and HDAC." PLOS Biology, edited by Albana Gattelli, vol. 21, No. 4, Apr. 2023, p. e3002038. Crossref, https://doi.org/10.1371/journal.pbio.3002038.
Scholze, Hanna, et al. "Combined EZH2 and Bcl-2 Inhibitors as Precision Therapy for Genetically Defined DLBCL Subtypes." Blood Advances, vol. 4, No. 20, Oct. 2020, pp. 5226-5231. Crossref, https://doi.org/10.1182/bloodadvances.2020002580.
Schümann, Franziska Lea, et al. "Divergent Effects of EZH1 and EZH2 Protein Expression on the Prognosis of Patients with T-Cell Lymphomas." Biomedicines, vol. 9, No. 12, Dec. 2021, p. 1842. Crossref, https://doi.org/10.3390/biomedicines9121842.
Schweizer, M., et al. "488P Phase I Trial of PF-06821497, a Potent and Selective Inhibitor of Enhancer of Zeste Homolog 2 (EZH2), in Follicular Lymphoma (FL), Small Cell Lung Cancer (SCLC) and

(56) References Cited

OTHER PUBLICATIONS

Castration-Resistant Prostate Cancer (CRPC)." Annals of Oncology, vol. 33, Sep. 2022, pp. S763-S764. Crossref, https://doi.org/10.1016/j.annonc.2022.07.616.
Schweizer, Michael Thomas, et al. "Phase 1 Trial of Mevrometostat (PF-06821497), a Potent and Selective Inhibitor of Enhancer of Zeste Homolog 2 (EZH2), in Castration-Resistant Prostate Cancer (CRPC)." Journal of Clinical Oncology, vol. 42, No. 16_suppl, Jun. 2024, pp. 5061-5061. Crossref, https://doi.org/10.1200/jco.2024.42.16_suppl.5061.
Serganova, Inna, et al. "Epigenetic, Metabolic, and Immune Crosstalk in Germinal-Center-Derived B-Cell Lymphomas: Unveiling New Vulnerabilities for Rational Combination Therapies." Frontiers in Cell and Developmental Biology, vol. 9, Jan. 2022. Crossref, https://doi.org/10.3389/fcell.2021.805195.
Sermer, David, et al. "Emerging Epigenetic-Modulating Therapies in Lymphoma." Nature Reviews Clinical Oncology, vol. 16, No. 8, Mar. 2019, pp. 494-507. Crossref, https://doi.org/10.1038/s41571-019-0190-8.
Shen, Yue, et al. "Differences between Lung Adenocarcinoma and Lung Squamous Cell Carcinoma: Driver Genes, Therapeutic Targets, and Clinical Efficacy." Genes & Diseases, Jul. 2024, p. 101374. Crossref, https://doi.org/10.1016/j.gendis.2024.101374.
Shi, Lihong, et al. "Pharmacological Inhibition of EZH2 Using a Covalent Inhibitor Suppresses Human Ovarian Cancer Cell Migration and Invasion." Molecular and Cellular Biochemistry, vol. 479, No. 4, May 2023, pp. 831-841. Crossref, https://doi.org/10.1007/s11010-023-04767-3.
Shin, Daniel Sanghoon, et al. "Targeting EZH2 to Overcome the Resistance to Immunotherapy in Lung Cancer." Seminars in Oncology, vol. 49, No. 3-4, Jun. 2022, pp. 306-318. Crossref, https://doi.org/10.1053/j.seminoncol.2022.06.005.
Shishido, Katherine, et al. "Targeting B7-H3 through EZH2 Inhibition in MYC-positive Group 3 Medulloblastoma." Oncology Reports, vol. 49, No. 6, Apr. 2023. Crossref, https://doi.org/10.3892/or.2023.8556.
Sibon, David. "Peripheral T-Cell Lymphomas: Therapeutic Approaches." Cancers, vol. 14, No. 9, May 2022, p. 2332. Crossref, https://doi.org/10.3390/cancers14092332.
Simon, R et al. "Randomized phase II clinical trials." Cancer treatment reports vol. 69,12 (1985):1375-81.
Singh, Pankaj Kumar. "Histone Methyl Transferases: A Class of Epigenetic Opportunities to Counter Uncontrolled Cell Proliferation." European Journal of Medicinal Chemistry, vol. 166, Mar. 2019, pp. 351-368. Crossref, https://doi.org/10.1016/j.ejmech.2019.01.069.
Song, Y., et al. "Enhancer of Zeste Homolog 2 (EZH2) Inhibitor SHR2554 in Relapsed or Refractory (R/R) Peripheral T-Cell Lymphoma (PTCL): Updated Outcomes From the First-in-Human Phase 1 Study." Hematological Oncology, vol. 41, No. S2, Jun. 2023, pp. 132-134. Portico, Crossref, https://doi.org/10.1002/hon.3163_89.
Song, Yuqin, et al. "SHR2554, an Enhancer of Zeste Homolog 2 (EZH2) Inhibitor, in Relapsed or Refractory (r/r) Mature Lymphoid Neoplasms: A First-in-Human Phase 1 Study." Journal of Clinical Oncology, vol. 40, No. 16_suppl, Jun. 2022, pp. 7525-7525. Crossref, https://doi.org/10.1200/jco.2022.40.16_suppl.7525.
Sprinzen Houghton, Lisa, et al. EZH2 Inhibition Sensitizes IDH1R132H Mutant Gliomas to Histone Deacetylase Inhibitor. Aug. 2023. Crossref, https://doi.org/10.1101/2023.07.31.551045.
Sprinzen, Lisa, et al. "EZH2 Inhibition Sensitizes IDH1R132H-Mutant Gliomas to Histone Deacetylase Inhibitor." Cells, vol. 13, No. 3, Jan. 2024, p. 219. Crossref, https://doi.org/10.3390/cells13030219.
Stein, H., et al. "The Expression of the Hodgkin's Disease Associated Antigen Ki-1 in Reactive and Neoplastic Lymphoid Tissue: Evidence That Reed-Sternberg Cells and Histiocytic Malignancies Are Derived from Activated Lymphoid Cells." Blood, vol. 66, No. 4, Oct. 1985, pp. 848-858. Crossref, https://doi.org/10.1182/blood.v66.4.848.848.
Straining, PharmD, Rachael, and William Eighmy, PharmD. "Tazemetostat: EZH2 Inhibitor." Journal of the Advanced Practitioner in Oncology, vol. 13, No. 2, Mar. 2022, pp. 158-163. Crossref, https://doi.org/10.6004/jadpro.2022.13.2.7.
Stuckey, Jacob I., et al. "Identification and Characterization of Second-Generation EZH2 Inhibitors with Extended Residence Times and Improved Biological Activity." Journal of Biological Chemistry, vol. 296, Jan. 2021, p. 100349. Crossref, https://doi.org/10.1016/j.jbc.2021.100349.
Stuver, Robert, and Shamir Geller. "Advances in the Treatment of Mycoses Fungoides and Sézary Syndrome: A Narrative Update in Skin-Directed Therapies and Immune-Based Treatments." Frontiers in Immunology, vol. 14, Oct. 2023. Crossref, https://doi.org/10.3389/fimmu.2023.1284045.
Stuver, Robert, et al. "Cumulative Incidence of Myeloid Neoplasms in Patients with Nodal T-Follicular Helper Cell Lymphoma." Blood, vol. 142, No. Supplement 1, Nov. 2023, pp. 4438-4438. Crossref, https://doi.org/10.1182/blood-2023-182272.
Sun, Shanshan, et al. "EZH2, a Prominent Orchestrator of Genetic and Epigenetic Regulation of Solid Tumor Microenvironment and Immunotherapy." Biochimica et Biophysica Acta (BBA)—Reviews on Cancer, vol. 1877, No. 2, Mar. 2022, p. 188700. Crossref, https://doi.org/10.1016/j.bbcan.2022.188700.
Sun, Yichen, et al. "Therapeutic Potential of Tucidinostat, a Subtype-Selective HDAC Inhibitor, in Cancer Treatment." Frontiers in Pharmacology, vol. 13, Sep. 2022. Crossref, https://doi.org/10.3389/fphar.2022.932914.
Susanibar-Adaniya, Sandra, and Stefan K. Barta. "2021 Update on Diffuse Large B Cell Lymphoma: A Review of Current Data and Potential Applications on Risk Stratification and Management." American Journal of Hematology, vol. 96, No. 5, Mar. 2021, pp. 617-629. Portico, Crossref, https://doi.org/10.1002/ajh.26151.
Tabata Hidetsugu et al: ""A Complete Gear System in N -Benzoyl-Carbazole Derivatives"", Organic Letters., [Online] vol. 16, No. 5, Feb. 24, 2014 (Feb. 24, 2014), pp. 1514-1517, XP055808348, us ISSN: 1523-7060, DOI: 10.1021/ol500417t Retrieved from the Internet: URL:https://pubs.acs.org/doi/pdf/10.1021 lo 1500417t> [retrieved on May 27, 2021] * Scheme 1; Citation 4.
Tabata Hidetsugu et al: ""Supporting Information A Complete Gear System in N-Benzoyl-Carbazole Derivatives"", Organic Letters, Feb. 14, 2014 (Feb. 14, 2014), pp. S0-S45, XP055808305, Retrieved from the Internet: URL:https://pubs.acs.org/doi/full/10.1021 /ol500417t [retrieved on May 27, 2021] * Page SI, paragraph 2., compound SI.
Takata, Katsuyoshi, et al. "Tumor-Associated Antigen PRAME Exhibits Dualistic Functions That Are Targetable in Diffuse Large B Cell Lymphoma." Journal of Clinical Investigation, vol. 132, No. 10, May 2022. Crossref, https://doi.org/10.1172/jci145343.
Teras, Lauren R., et al. "2016 US Lymphoid Malignancy Statistics by World Health Organization Subtypes." CA: A Cancer Journal for Clinicians, vol. 66, No. 6, Sep. 2016, pp. 443-459. Portico, Crossref, https://doi.org/10.3322/caac.21357.
Thandra, Krishna C., et al. "Epidemiology of Non-Hodgkin's Lymphoma." Medical Sciences, vol. 9, No. 1, Jan. 2021, p. 5. Crossref, https://doi.org/10.3390/medsci9010005.
Twiss and Heinzelmann, "The Oxidation of Iodinated Phthalic and Benzoic Acids", The Journal of Organic Chemistry, 1950, pp. 496-510.
Vaswani, Rishi G., et al. "Identification of (R)-N-((4-Methoxy-6-Methyl-2-Oxo-1,2-Dihydropyridin-3-YI)Methyl)-2-Methyl-1-(1-(1-(2,2,2-Trifluoroethyl)Piperidin-4-YI)Ethyl)-1H-Indole-3-Carboxamide (CPI-1205), a Potent and Selective Inhibitor of Histone Methyltransferase EZH2, Suitable for Phase I Clinical Trials for B-Cell Lymphomas." Journal of Medicinal Chemistry, vol. 59, No. 21, Oct. 2016, pp. 9928-9941. Crossref, https://doi.org/10.1021/acs.jmedchem.6b01315.
Velez, Julia, et al. "Discovery of a Novel, Highly Potent EZH2 Protac Degrader for Targeting Non-Canonical Oncogenic Functions of EZH2." European Journal of Medicinal Chemistry, vol. 267, Mar. 2024, p. 116154. Crossref, https://doi.org/10.1016/j.ejmech.2024.116154.
Velichutina, Irina, et al. "EZH2-Mediated Epigenetic Silencing in Germinal Center B Cells Contributes to Proliferation and

(56) References Cited

OTHER PUBLICATIONS

Lymphomagenesis." Blood, vol. 116, No. 24, Dec. 2010, pp. 5247-5255. Crossref, https://doi.org/10.1182/blood-2010-04-280149.
Verma, Ayushi, et al. "Emerging Role of EZH2 in Solid Tumor Metastasis." Biochimica et Biophysica Acta (BBA)—Reviews on Cancer, vol. 1880, No. 1, Feb. 2025, p. 189253. Crossref, https://doi.org/10.1016/j.bbcan.2024.189253.
Von Keudell, Gottfried, and Gilles Salles. "The Role of Tazemetostat in Relapsed/Refractory Follicular Lymphoma." Therapeutic Advances in Hematology, vol. 12, Jan. 2021. Crossref, https://doi.org/10.1177/20406207211015882.
Vose, Julie et al. "International Peripheral T-Cell and Natural Killer/T-Cell Lymphoma Study: Pathology Findings and Clinical Outcomes." Journal of Clinical Oncology, vol. 26, No. 25, Sep. 2008, pp. 4124-4130. Crossref, https://doi.org/10.1200/jco.2008.16.4558.
Wan, Guoquan, et al. "A Patent Review of EZH2 Inhibitors from 2017 and Beyond." Expert Opinion on Therapeutic Patents, vol. 33, No. 4, Apr. 2023, pp. 293-308. Crossref, https://doi.org/10.1080/13543776.2023.2206018.
Wang, Bohan, et al. "EZH2 in Hepatocellular Carcinoma: Progression, Immunity, and Potential Targeting Therapies." Experimental Hematology & Oncology, vol. 12, No. 1, Jun. 2023. Crossref, https://doi.org/10.1186/s40164-023-00405-2.
Wang, Jun, et al. "EZH2 Noncanonically Binds CMyc and P300 through a Cryptic Transactivation Domain to Mediate Gene Activation and Promote Oncogenesis." Nature Cell Biology, vol. 24, No. 3, Feb. 2022, pp. 384-399. Crossref, https://doi.org/10.1038/s41556-022-00850-x.
Wei, Lai, et al. "Dual-Target EZH2 Inhibitor: Latest Advances in Medicinal Chemistry." Future Medicinal Chemistry, vol. 16, No. 15, Jul. 2024, pp. 1561-1582. Crossref, https://doi.org/10.1080/17568919.2024.2380243.
Whittaker, Sean, et al. "How I Treat Mycosis Fungoides and Sézary Syndrome." Blood, vol. 127, No. 25, Jun. 2016, pp. 3142-3153. Crossref, https://doi.org/10.1182/blood-2015-12-611830.
Wilhelm, M., et al. "First-Line Therapy of Peripheral T-Cell Lymphoma: Extension and Long-Term Follow-up of a Study Investigating the Role of Autologous Stem Cell Transplantation." Blood Cancer Journal, vol. 6, No. 7, Jul. 2016, pp. e452-e452. Crossref, https://doi.org/10.1038/bcj.2016.63.
Wozniak, Michal, and Malgorzata Czyz. "Exploring Oncogenic Roles and Clinical Significance of EZH2: Focus on Non-Canonical Activities." Therapeutic Advances in Medical Oncology, vol. 17, Jan. 2025. Crossref, https://doi.org/10.1177/17588359241306026.
Written Opinion of the International Search Authority (and English translation thereof) dated Dec. 15, 2022 issued in International Application No. PCT/CN2022/125302.
Written Opinion of the International Search Authority (and English translation thereof) dated Nov. 28, 2022 issued in International Application PCT/CN2022/115763.
Wu, Di, et al. "Discovery of Novel Pyridone-Benzamide Derivatives Possessing a 1-Methyl-2-Benzimidazolinone Moiety as Potent EZH2 Inhibitors for the Treatment of B-Cell Lymphomas." Bioorganic & Medicinal Chemistry, vol. 105, May 2024, p. 117725. Crossref, https://doi.org/10.1016/j.bmc.2024.117725.
Wu, Gongwei, et al. "TP63 Fusions Drive Multicomplex Enhancer Rewiring, Lymphomagenesis, and EZH2 Dependence." Science Translational Medicine, vol. 15, No. 714, Sep. 2023. Crossref, https://doi.org/10.1126/scitranslmed.adi7244.
Xiao, Boren, et al. "Design, Synthesis, and Evaluation of VHL-Based EZH2 Degraders for Breast Cancer." Bioorganic Chemistry, vol. 143, Feb. 2024, p. 107078. Crossref, https://doi.org/10.1016/j.bioorg.2023.107078.
Xie, Caiqin, et al. "Molecular Insights into Pathogenesis and Targeted Therapy of Peripheral T Cell Lymphoma." Experimental Hematology & Oncology, vol. 9, No. 1, Nov. 2020. Crossref, https://doi.org/10.1186/s40164-020-00188-w.
Xie, Huiru, et al. "Design, Synthesis and Evaluation of EZH2-Based PROTACs Targeting PRC2 Complex in Lymphoma." Bioorganic Chemistry, vol. 140, Nov. 2023, p. 106762. Crossref, https://doi.org/10.1016/j.bioorg.2023.106762.
Xing Wang, et al., "The Synergistic Anti-Tumor Activity of EZH2 Inhibitor SHR2554 and HDAC Inhibitor Chidamide through ORC1 Reduction of DNA Replication Process in Diffuse Large B Cell Lymphoma", Cancers, 13:4249-4249, (2021).
Xu, Mengfei, et al. "Treating Human Cancer by Targeting EZH2." Genes & Diseases, Apr. 2024, p. 101313. Crossref, https://doi.org/10.1016/j.gendis.2024.101313.
Xu, Pingsheng, et al. Effect of a Strong CYP3A4 Inducer Rifampin on the Pharmacokinetics of SHR2554 in Healthy Chinese Volunteers: A Drug-Drug Interaction Study. May 2023. Crossref, https://doi.org/10.22541/au.168322865.51461018/v1.
Xu, Xin, et al. "Conformationally Constrained Potent Inhibitors for Enhancer of Zeste Homolog 2 (EZH2)." Bioorganic & Medicinal Chemistry Letters, vol. 97, Jan. 2024, p. 129558. Crossref, https://doi.org/10.1016/j.bmcl.2023.129558.
Yamagishi, Makoto, et al. "Mechanisms of action and resistance in histone methylation-targeted therapy." Nature 627.8002 (2024): 221-228.
Yang, Xiaobao, et al. "Structure-Activity Relationship Studies for Enhancer of Zeste Homologue 2 (EZH2) and Enhancer of Zeste Homologue 1 (EZH1) Inhibitors." Journal of Medicinal Chemistry, vol. 59, No. 16, Aug. 2016, pp. 7617-7633. Crossref, https://doi.org/10.1021/acs.jmedchem.6b00855.
Yang, Xiaojuan, et al. "Recent Advances in EZH2-Based Dual Inhibitors in the Treatment of Cancers." European Journal of Medicinal Chemistry, vol. 256, Aug. 2023, p. 115461. Crossref, https://doi.org/10.1016/j.ejmech.2023.115461.
Yang, Yiqi, et al. "FGFR4 and EZH2 Inhibitors Synergistically Induce Hepatocellular Carcinoma Apoptosis via Repressing YAP Signaling." Journal of Experimental & Clinical Cancer Research, vol. 42, No. 1, Apr. 2023. Crossref, https://doi.org/10.1186/s13046-023-02659-4.
Yang, Yiying, et al. "EZH2 Inhibition Dampens Autoantibody Production in Lupus by Restoring B Cell Immune Tolerance." International Immunopharmacology, vol. 119, Jun. 2023, p. 110155. Crossref, https://doi.org/10.1016/j.intimp.2023.110155.
Yomtoubian, Shira, et al. "Inhibition of EZH2 Catalytic Activity Selectively Targets a Metastatic Subpopulation in Triple-Negative Breast Cancer." Cell Reports, vol. 30, No. 3, Jan. 2020, pp. 755-770.e6. Crossref, https://doi.org/10.1016/j.celrep.2019.12.056.
Yoshimitsu, Makoto, et al. "Pivotal Phase 2 Study of the EZH1 and EZH2 Inhibitor Valemetostat Tosylate (DS-3201b) in Patients with Relapsed or Refractory Adult T-Cell Leukemia/Lymphoma." Blood, vol. 138, No. Supplement 1, Nov. 2021, pp. 303-303. Crossref, https://doi.org/10.1182/blood-2021-146657.
Ysebaert, Loic, et al. "Tazemetostat in Combination with R-CHOP in Patients with High-Risk, Frontline Follicular Lymphoma (Epi-RCHOP): A Phase II Study from the Lysa." Blood, vol. 142, No. Supplement 1, Nov. 2023, pp. 297-297. Crossref, https://doi.org/10.1182/blood-2023-185057.
Yu, Lei, et al. "Dysregulation of Iron Homeostasis by TfR-1 Renders EZH2 Wild Type Diffuse Large B-Cell Lymphoma Resistance to EZH2 Inhibition." Acta Pharmacologica Sinica, vol. 44, No. 10, May 2023, pp. 2113-2124. Crossref, https://doi.org/10.1038/s41401-023-01097-4.
Yu, Xufen, et al. "Dissecting and Targeting Noncanonical Functions of EZH2 in Multiple Myeloma via an EZH2 Degrader." Oncogene, vol. 42, No. 13, Feb. 2023, pp. 994-1009. Crossref, https://doi.org/10.1038/s41388-023-02618-5.
Yuan, Hongchao, et al. "Epigenetic Inhibitors for Cancer Treatment." Epigenetic Regulation of Cancer—Part B, 2024, pp. 89-144. Crossref, https://doi.org/10.1016/bs.ircmb.2023.06.003.
Yun Kyoung Ryu, et al., "Easy does it! New EZH2 inhibitor SHR2554 is safe and active in relapsed or refractory lymphoma", The Lancet Haematology, 9:e463-e465, Jul. 2022.
Yuqin Song, et al., "Enhancer of zeste homolog 2 inhibitor SHR2554 in relapsed or refractory peripheral T-cell lymphoma: data from the first-in-human phase 1 study", Clinical Cancer Research, Jan. 9, 2024.

(56) References Cited

OTHER PUBLICATIONS

Yuqin Song, et al., "SHR2554, an EZH2 inhibitor, in relapsed or refractory mature lymphoid neoplasms: a first-in-human, dose-escalation, dose-expansion, and clinical expansion phase 1 trial", The Lancet Haematology, 9:e493-e503, Jul. 2022.
Zain, Jasmine, and Avyakta Kallam. "Challenges in Nodal Peripheral T-Cell Lymphomas: From Biological Advances to Clinical Applicability." Frontiers in Oncology, vol. 13, Apr. 2023. Crossref, https://doi.org/10.3389/fonc.2023.1150715.
Zauderer, Marjorie G., et al. "EZH2 Inhibitor Tazemetostat in Patients with Relapsed or Refractory, BAP1-Inactivated Malignant Pleural Mesothelioma: A Multicentre, Open-Label, Phase 2 Study." The Lancet Oncology, vol. 23, No. 6, Jun. 2022, pp. 758-767. Crossref, https://doi.org/10.1016/s1470-2045(22)00277-7.
Zauderer, Marjorie Glass, et al. "Safety and Efficacy of Tazemetostat, an Enhancer of Zeste-Homolog 2 Inhibitor, in Patients with Relapsed or Refractory Malignant Mesothelioma." Journal of Clinical Oncology, vol. 38, No. 15_suppl, May 2020, pp. 9058-9058. Crossref, https://doi.org/10.1200/jco.2020.38.15_suppl.9058.
Zeng, Jia, et al. "Targeting EZH2 for Cancer Therapy: From Current Progress to Novel Strategies." European Journal of Medicinal Chemistry, vol. 238, Aug. 2022, p. 114419. Crossref, https://doi.org/10.1016/j.ejmech.2022.114419.
Zhang, Huilai, et al. "Clinical Significance of Enhancer of Zeste Homolog 2 and Histone Deacetylases 1 and 2 Expression in Peripheral T-cell Lymphoma." Oncology Letters, May 2019. Crossref, https://doi.org/10.3892/ol.2019.10410.
Zhang, Jinwei, et al. Discovery of Epigenetic Modulators Targeting Hdacs and Ezh2 Simultaneously for the Treatment of Hematological Malignancies. 2024. Crossref, https://doi.org/10.2139/ssrn.4987105.
Zhang, Ping, and Mingzhi Zhang. "Epigenetic Alterations and Advancement of Treatment in Peripheral T-Cell Lymphoma." Clinical Epigenetics, vol. 12, No. 1, Nov. 2020. Crossref, https://doi.org/10.1186/s13148-020-00962-x.
Zhang, Qian, et al. "EZH2 Serves as a Promising Therapeutic Target for Fibrosis." Bioorganic Chemistry, vol. 137, Aug. 2023, p. 106578. Crossref, https://doi.org/10.1016/j.bioorg.2023.106578.
Zhang, Shengzhe, et al. CRACD Loss Promotes Small Cell Lung Cancer Tumorigenesis via EZH2-Mediated Immune Evasion. Feb. 2023. Crossref, https://doi.org/10.1101/2023.02.15.528365.
Zhang, Xi, et al. "Combined Inhibition of PARP and EZH2 for Cancer Treatment: Current Status, Opportunities, and Challenges." Frontiers in Pharmacology, vol. 13, Oct. 2022. Crossref, https://doi.org/10.3389/fphar.2022.965244.
Zhang, Yaping, et al. "Therapeutic Options in Peripheral T Cell Lymphoma." Journal of Hematology & Oncology, vol. 9, No. 1, Apr. 2016. Crossref, https://doi.org/10.1186/s13045-016-0267-0.
Zhang, Yi, et al. "Discovery of a New-Generation S-Adenosylmethionine-Noncompetitive Covalent Inhibitor Targeting the Lysine Methyltransferase Enhancer of Zeste Homologue 2." Journal of Medicinal Chemistry, vol. 66, No. 11, May 2023, pp. 7629-7644. Crossref, https://doi.org/10.1021/acs.jmedchem.3c00504.
Zhang, Zhuangzhuang, et al. "Downregulation of EZH2 Inhibits Epithelial-Mesenchymal Transition in Enzalutamide-resistant Prostate Cancer." The Prostate, vol. 83, No. 15, Jul. 2023, pp. 1458-1469. Portico, Crossref, https://doi.org/10.1002/pros.24602.
Zhao, Zhou, et al. "Safety Profile of EZH2 Inhibitors for Cancer: A Systematic Review and Meta-Analysis." PeerJ, vol. 13, Jan. 2025, p. e18871. Portico, Crossref, https://doi.org/10.7717/peerj.18871.
Zheng, Xiaoqing, et al. "Ezh2 Knockout in B Cells Impairs Plasmablast Differentiation and Ameliorates Lupus-like Disease in MRL/Lpr Mice." Arthritis & Rheumatology, vol. 75, No. 8, May 2023, pp. 1395-1406. Portico, Crossref, https://doi.org/10.1002/art.42492.
Zhou, Bin, et al. "Discovery of Dihydropyridinone Derivative as a Covalent EZH2 Degrader." European Journal of Medicinal Chemistry, vol. 261, Dec. 2023, p. 115825. Crossref, https://doi.org/10.1016/j.ejmech.2023.115825.
Zhou, Yan, et al. "Efficacy and Safety of SHR-2554 in Advanced Epithelioid Sarcoma: A Phase 2 Trial." Journal of Clinical Oncology, vol. 42, No. 16_suppl, Jun. 2024, pp. 11549-11549. Crossref, https://doi.org/10.1200/jco.2024.42.16_suppl.11549.
Zhu, Yongxia, et al. "Pharmacological Inhibition of EZH2 by ZLD1039 Suppresses Tumor Growth and Pulmonary Metastasis in Melanoma Cells in Vitro and in Vivo." Biochemical Pharmacology, vol. 210, Apr. 2023, p. 115493. Crossref, https://doi.org/10.1016/j.bcp.2023.115493.
Zinzani, Pier Luigi, et al. "Valemetostat for Patients with Relapsed or Refractory Peripheral T-Cell Lymphoma (VALENTINE-PTCL01): A Multicentre, Open-Label, Single-Arm, Phase 2 Study." The Lancet Oncology, vol. 25, No. 12, Dec. 2024, pp. 1602-1613. Crossref, https://doi.org/10.1016/s1470-2045(24)00503-5.
Zlocowski, N., et al. "The Epigenetic EZH2/H3K27me3 Axis Modulates Lactotroph Tumor Cell Proliferation." Journal of Endocrinology, vol. 257, No. 2, Feb. 2023. Crossref, https://doi.org/10.1530/joe-22-0195.
Anandan et al., "1-(1-Acetyl-peperidin-4-yl)-3-adamantan-1-yl-urea (AR9281) as a potent, selective, and orally available soluble epoxide hydrolase inhibitor with efficacy in rodent models of hypertension and dysglycemia," Bioorganic & Medicinal Chemistry Letters, vol. 21, pp. 983-988 (2011).
Arbuckle et al., "Optimisation of Pharmacokinetic Properties to Afford an Orally Bioavailable and Selective V1A Receptor Antagonist," Bioorganic & Medicinal Chemistry Letters, vol. 21, pp. 4622-4628 (2011).
Chang et al., "The Role of EZH2 in Tumour Progression," British Journal of Cancer, vol. 106, No. 2, pp. 243-247 (2012).
Hewings et al., "Optimization of 3,5-Dimethylisoxazole Derivatives as Potent Bromodomain Ligands," Journal of Medicinal Chemistry, vol. 56, pp. 3217-3227 (2013).
Horig, H., Pullman, W. From bench to clinic and back: Perspective on the 1st IQPC Translational Research conference. Journal of Translational Medicine. Dec. 2004, 2, 44.
International Search Report issued Jan. 22, 2017 in International Application No. PCT/CN2016/104318.
Int'l Search Report issued Aug. 14, 2018 in Int'l Application No. PCT/CN2018/087272.
Lue et al., Emerging EZH2 inhibitors and Their Application in Lymphoma. Current Hematologic Malignancy Reports, 2018, 13, 369-382.
Lund et al., "EZH2 in Normal and Malignant Hematopoiesis," Leukemia, vol. 28, No. 1, pp. 44-49 (2014).
Schafer, S., Kolkhof, P. Failure is an option: learning from unsuccessful proof-of-concept trials. Drug Discovery Today. Nov. 2008, 13, 913-916.
Schultz et al., "Asymmetric syntheses of 1,6-Dialkyl-1,4-cyclohexadiene Derivatives," Journal of American Chemical Society, vol. 113, No. 13, pp. 4931-4936 (1991).
Shen et al., "Update of Research on the Role of EZH2 in Cancer Progression," Onco Targets and Therapy, vol. 6, pp. 321-324 (2013).
Yan et al., "EZH2 Overexpression in Natural Killer/T-cell Lymphoma Confers Growth Advantage Independently of Histone Methyltransferase Activity," Blood, vol. 121, pp. 4512-4520 (2013).
Chemical Abstracts Registry No. 1804457-76-8, indexed in the Registry file on Sep. 10, 2015. (Year:2015).
Chemical Abstracts Registry No. 1895361-02-0, indexed in the Registry file on Apr. 22, 2016. (Year:2016).
Chemical Abstracts Registry No. 1896401-67-4, indexed in the Registry file on Apr. 24, 2016. (Year:2016).
Chemical Abstracts Registry No. 2110161-86-7, indexed in the Registry file on Aug. 8, 2017. (Year:2017).
International Search Report and Written Opinion for International Patent Application No. PCT/CN2018/087246, mailed Aug. 1, 2018.
International Search Report and Written Opinion for International Patent Application No. PCT/CN2018/114798, mailed Feb. 15, 2019.
Knutson, Sarah K., et al. "Selective Inhibition of EZH2 by EPZ-6438 Leads to Potent Antitumor Activity in EZH2-Mutant Non-Hodgkin Lymphoma." Molecular Cancer Therapeutics, vol. 13, No. 4, Apr. 2014, pp. 842-854. Crossref, https://doi.org/10.1158/1535-7163.mct-13-0773.

(56) References Cited

OTHER PUBLICATIONS

Tiacci, Enrico, et al. "High-Risk Clonal Hematopoiesis as the Origin of AITL and NPM1-Mutated AML." New England Journal of Medicine, vol. 379, No. 10, Sep. 2018, pp. 981-984. Crossref, https://doi.org/10.1056/nejmc1806413.
Yamagishi, Makoto, et al. "Targeting Excessive EZH1 and EZH2 Activities for Abnormal Histone Methylation and Transcription Network in Malignant Lymphomas." Cell Reports, vol. 29, No. 8, Nov. 2019, pp. 2321-2337.e7. Crossref, https://doi.org/10.1016/j.celrep.2019.10.083.
Morissette et al, Advanced Drug Delivery Reviews, vol. 56, pp. 275-300 (Year: 2004).*
Int'l Search Report dated Aug. 14, 2018 in Int'l Application No. PCT/CN2018/087272.

* cited by examiner

CRYSTAL OF BENZOFURAN DERIVATIVE FREE BASE AND PREPARATION METHOD

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATION

This application is a *reissue application of U.S. application Ser. No. 16/612,168, filed Nov. 8, 2019, which issued as U.S. Pat. No. 11,155,537 on Oct. 26, 2021, and which is a* Section 371 of International Application No. PCT/CN2018/087272, filed May 17, 2018, which was published in the Chinese language on Nov. 22, 2018, under International Publication No. WO 2018/210302 A1, which claims priority under 35 U.S.C. § 119(b) to Chinese Application No. 201710350574.5, filed May 18, 2017, the disclosures of which are incorporated herein by reference in their entirety.

FIELD OF THE INVENTION

The present invention relates to crystal forms A, B, C and D of N-((4,6-dimethyl-2-oxo-1,2-dihydropyridin-3 -yl) methyl)-5-ethyl-6-(ethyl(tetrahydro-2 H-pyran-4-yl) amino)-2-(piperidin-1-ylmethyl)benzofuran-4-carboxamide, as well as preparation methods thereof.

BACKGROUND OF THE INVENTION

Lymphoma is a malignant tumor originating from the lymphoid hematopoietic system. It is classified into non-Hodgkin lymphoma (NHL) and Hodgkin lymphoma (HL) according to the tumor cells. In Asia, 90% of lymphoma patients are NHL patients having lymphocytes, histiocytes or reticular cells with different degrees of differentiation in pathology. According to the natural course of NHL, NHL can be classified into three major clinical types, namely highly invasive, invasive and indolent lymphoma. According to the different lymphocyte origins, it can be classified into B cells, T cells and natural killer (NK) cells lymphoma. The main function of B cells is to secrete various antibodies to protect the body against various external invasions.

The histone methyltransferase encoded by the EZH2 gene is a catalytic component of polycomb repressive complex 2 (PRC2). EZH2 levels are abnormally elevated in cancer tissues compared to normal tissues, and EZH2 is most highly expressed in advanced cancers or poor prognosis. In some types of cancers, EZH2 overexpression occurs simultaneously with amplification of the EZH2 gene. A number of si/shRNA experimental studies show that reduction of EZH2 expression in tumor cell lines can inhibit tumor cell proliferation, migration and invasion, or angiogenesis, and lead to apoptosis. WO2017084494 (PCT/CN2016/104318, filing date of 2 Nov. 2016) discloses an EZH2 inhibitor having the following structure:

(I)

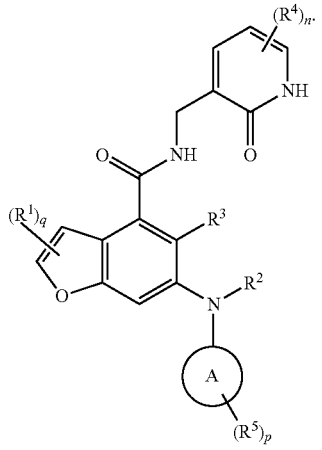

Patent application that discloses selective EZH2 inhibitor includes WO2012005805, WO2012050532, WO2012118812, WO2012142513, WO2012142504, WO2013049770, WO2013039988, WO2013067300, WO2015141616, WO2011140325 and the like.

The crystal structure of a pharmaceutically active ingredient often affects the chemical stability of the drug. Different crystallization conditions and storage conditions may lead to changes in the crystal structure of a compound, and sometimes accompanying production of other crystal forms. In general, an amorphous drug product does not have a regular crystal structure, and often has other defects such as poor product stability, excessively fine crystal, difficult filtration, easy agglomeration, and poor liquidity. The polymorphic forms of a drug have different requirements on storage, production and amplification. Therefore, it is necessary to investigate the crystal forms of the compound of formula (I) and the preparation method thereof so as to improve the various properties of the compound of formula (I).

SUMMARY OF THE INVENTION

The technical problem to be solved by the present invention is to provide crystal forms A, B, C and D of N-((4,6-dimethyl-2-oxo-1,2-dihydropyridin-3-yl)methyl)-5 -ethyl-6-(ethyl(tetrahydro-2 H-pyran-4-yl)amino)-2-(piperidin-1-ylmethyl)benzofuran-4-carboxamide, as well as preparation methods thereof. The crystal forms prepared by the present invention have a good stability.

The technical solution of the present invention is as follows:

The present invention provides crystal form A of a compound of formula (I), characterized in that: the crystal form A has a powder X-ray diffraction spectrum, which is obtained by using Cu-Kα radiation and represented by diffraction angle 2θ angle, in which there are characteristic peaks at diffraction angle 2θ angles of 7.60, 8.51, 11.80, 12.38, 13.52, 13.73, 14.48, 15.23, 15.99, 16.10, 16.82, 16.99, 17.35, 18.24, 20.82, 21.57, 21.91, 22.57, 22.76, 22.88, 24.29, 24.47, 25.24, 25.90, 27.23 and 27.74, wherein the error range of 2θ angle of each characteristic peak is±0.2, (I)

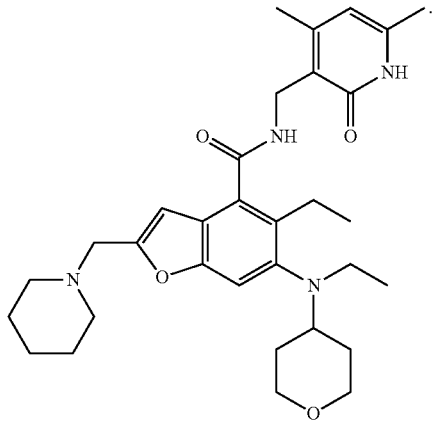

Preferably, there are characteristic peaks at diffraction angle 2θ angles of 7.60, 8.51, 10.37, 11.16, 11.80, 12.38, 12.89, 13.52, 13.73, 14.03, 14.48, 15.23, 15.99, 16.10, 16.43, 16.82, 16.99, 17.35, 18.24, 18.92, 19.17, 20.68, 20.82, 21.57, 21.91, 22.57, 22.76, 22.88, 23.53, 23.68, 24.00, 24.29, 24.47, 24.91, 25.24, 25.72, 25.90, 27.23, 27.74 and 35.63, wherein the error range of 2θ angle of each characteristic peak is ±0.2.

The present invention also provides the single crystal data of crystal form A, characterized in that the crystal form A is an orthorhombic crystal system; the space group is Pbca; the unit cell parameters are a=17.051(3)Å, b=15.840(3)Å, c=23.249(5)Å, α=β=γ=90.0; and the unit cell volume is 6279(2)Å$^3$.

The present invention also provides a method for preparing the crystal form A, characterized in that the method is selected from the group consisting of:

method I, dissolving the compound of formula (I) in a solvent to crystallize, filtering, washing and drying the resulting crystal to obtain the desired crystal form A, wherein the solvent is selected from the group consisting of an amide solvent, a mixed solvent of an amide solvent and water, and a mixed solvent of a halohydrocarbon and a nitrile, the amide solvent is selected from the group consisting of N,N-dimethylformamide and N,N-dimethylacetamide, the halohydrocarbon solvent is dichloromethane, and the nitrile solvent is acetonitrile, and the crystallization method is selected from the group consisting of room temperature crystallization, cooling crystallization, solvent volatilization crystallization and crystallization induced by addition of a seed crystal;

method II, dissolving the compound of formula (I) in a good solvent, adding an anti-solvent to crystallize, filtering and drying the resulting crystal to obtain the desired crystal form A, wherein the good solvent is an alcohol solvent, the alcohol solvent is selected from the group consisting of methanol, ethanol and isopropanol, and the anti-solvent is water, and the crystallization method is selected from the group consisting of room temperature crystallization, cooling crystallization, solvent volatilization crystallization and crystallization induced by addition of a seed crystal; and method III, adding the compound of formula (I) to a solvent, pulping the mixture, filtering and drying the resulting crystal to obtain the desired crystal form A, wherein the solvent is selected from the group consisting of a mixed solvent of an amide solvent and water, and a mixed solvent of a halohydrocarbon and a nitrile, the amide solvent is selected from the group consisting of N,N-dimethylformamide and N,N-dimethylacetamide, the halohydrocarbon solvent is dichloromethane, and the nitrile solvent is acetonitrile.

The present invention also provides a method for preparing the single crystal of crystal form A, characterized in that the method comprises:

dissolving the compound of formula (I) in a solvent to crystallize, filtering and drying the resulting crystal to obtain the desired single crystal of crystal form A, wherein the solvent is a mixed solvent of a halohydrocarbon and a nitrile, the halohydrocarbon solvent is dichloromethane, and the nitrile solvent is acetonitrile; the ratio of the halohydrocarbon to the nitrile is 20:1-1:20, and preferably 1:10, the crystallization method is selected from the group consisting of room temperature crystallization, cooling crystallization, solvent volatilization crystallization and crystallization induced by addition of a seed crystal.

The present invention also provides crystal form B of the compound of formula (I), characterized in that: the crystal form B has a powder X-ray diffraction spectrum, which is obtained by using Cu-Kα radiation and represented by diffraction angle 2θ angle, in which there are characteristic peaks at diffraction angle 2θ angles of 6.31, 7.24, 10.99, 12.07, 14.56, 17.94, 19.13, 19.71, 21.48, 24.15, 27.10 and 28.83, wherein the error range of 20 angle of each characteristic peak is ±0.2.

Preferably, there are characteristic peaks at diffraction angle 2θ angles of 6.31, 7.24, 8.92, 10.38, 10.99, 12.07, 14.56, 15.10, 16.36, 17.29, 17.94, 19.13, 19.71, 21.12, 21.48, 22.59, 24.15, 25.45, 26.28, 26.52, 27.10, 28.83, 30.07, 31.37, 32.56, 33.65, 34.64, 36.09, 37.13 and 40.04, wherein the error range of 2θ angle of each characteristic peak is ±0.2.

The present invention also provides a method for preparing the crystal form B, characterized in that the method is selected from the group consisting of:

method I, dissolving the compound of formula (I) in a solvent to crystallize, filtering and drying the resulting crystal to obtain the desired crystal form B, wherein the solvent is ethanol, and the crystallization method is selected from the group consisting of room temperature crystallization, cooling crystallization, solvent volatilization crystallization and crystallization induced by addition of a seed crystal; and method II, dissolving the compound of formula (I) in a good solvent, adding an anti-solvent to crystallize, filtering and drying the resulting crystal to obtain the desired crystal form B, wherein the good solvent is ethanol, and the anti-solvent is water, the crystallization method is selected from the group consisting of room temperature crystallization, cooling crystallization, solvent volatilization crystallization and crystallization induced by addition of a seed crystal.

The present invention further provides crystal form C of the compound of formula (I), characterized in that: the crystal form C has a powder X-ray diffraction spectrum, which is obtained by using Cu-Kα radiation and represented by diffraction angle 2θ angle, in which there are characteristic peaks at diffraction angle 2θ of 7.40, 8.62, 9.49, 12.32, 13.39, 15.52, 19.15, 19.17, 21.42 and 22.78, wherein the error range of 2θ angle of each characteristic peak is ±0.2.

Preferably, there are characteristic peaks at diffraction angle 2θ angles of 7.40, 8.62, 9.49, 9.96, 11.12, 12.32, 13.39, 14.21, 14.85, 15.52, 16.50, 17.67, 18.28, 19.15, 19.17, 20.06, 20.80, 21.42, 21.89, 22.20, 22.78, 23.41, 24.74, 25.34, 26.70, 27.38, 28.64, 29.63, 30.20 and 31.15, wherein the error range of 2θ angle of each characteristic peak is ±0.2.

The present invention also provides a method for preparing the crystal form C, characterized in that the method comprises the following steps of:

dissolving the compound of formula (I) in a good solvent, adding an anti-solvent to crystallize, filtering and drying the resulting crystal to obtain the desired crystal form C, wherein the good solvent is an ether solvent, the ether solvent is 1,4-dioxane, the anti-solvent is selected from the group consisting of an aliphatic hydrocarbon solvent and an alicyclic hydrocarbon solvent, the aliphatic hydrocarbon solvent is n-heptane, and the alicyclic hydrocarbon solvent is cyclohexane, and the crystallization method is selected from the group consisting of room temperature crystallization, cooling crystallization, solvent volatilization crystallization and crystallization induced by addition of a seed crystal.

The present invention also provides crystal form D of the compound of formula (I), characterized in that: the crystal form D has a powder X-ray diffraction spectrum, which is obtained by using Cu-Kα radiation and represented by diffraction angle 2θ angle, in which there are characteristic peaks at diffraction angle 2θ angles of 8.41, 8.85, 11.38, 12.18, 13.45, 15.15, 16.73, 17.59, 17.68, 20.45, 21.51, 22.72, 24.53, 24.91 and 27.11, wherein the error range of 2θ angle of each characteristic peak is ±0.2.

Preferably, there are characteristic peaks at diffraction angle 2θ angles of 8.41, 8.85, 10.15, 11.38, 12.18, 13.45, 14.40, 15.15, 16.73, 17.59, 17.68, 18.42, 18.91, 19.22, 20.45, 21.15, 21.51, 22.11, 22.72, 24.03, 24.53, 24.91, 25.54, 26.54, 27.11, 27.61, 29.04, 30.49, 31.31, 33.00, 33.88, 35.52, 37.53, 40.46, 41.36, 42.40 and 44.02, wherein the error range of 2θ angle of each characteristic peak is ±0.2.

The present invention also provides the single crystal data of crystal form D, characterized in that the crystal form D is an orthorhombic crystal system; the space group is Pbca; the unit cell parameters are a=17.4737(6)Å, b=17.5933(5)Å, c=19.9907(7)Å, α=β=γ=90.0°; and the unit cell volume is 6145.5 (3)$Å^3$.

The present invention also provides a method for preparing the crystal form D, characterized in that the method is selected from the group consisting of:

method I, dissolving the compound of formula (I) in a solvent to crystallize, filtering and drying the resulting crystal to obtain the desired crystal form D, wherein the solvent is selected from the group consisting of an alcohol solvent, an ether solvent, a mixed solvent of an alcohol and water, a mixed solvent of an ether and water, a mixed solvent of an alcohol and an aliphatic hydrocarbon, and a mixed solvent of an ether and an aliphatic hydrocarbon, the alcohol solvent is selected from the group consisting of methanol, ethanol and isopropanol, the ether solvent is selected from the group consisting of tetrahydrofuran and 1,4-dioxane, and the aliphatic hydrocarbon solvent is n-heptane, and the crystallization method is selected from the group consisting of room temperature crystallization, cooling crystallization, solvent volatilization crystallization and crystallization induced by addition of a seed crystal;

method II, dissolving the compound of formula (I) in a good solvent, adding an anti-solvent to crystallize, filtering and drying the resulting crystal to obtain the desired crystal form D, wherein the good solvent is selected from the group consisting of an alcohol solvent and an ether solvent, the alcohol solvent is selected from the group consisting of methanol and isopropanol, the ether solvent is tetrahydrofuran, and the anti-solvent is water; or the good solvent is an ether, the ether solvent is tetrahydrofuran, the anti-solvent is selected from the group consisting of an aliphatic hydrocarbon solvent and an alicyclic hydrocarbon solvent, the aliphatic hydrocarbon solvent is n-heptane, and the alicyclic hydrocarbon solvent is cyclohexane, and the crystallization method is selected from the group consisting of room temperature crystallization, cooling crystallization, solvent volatilization crystallization and crystallization induced by addition of a seed crystal; and method III, adding the compound of formula (I) to a solvent, pulping the mixture, filtering and drying the resulting crystal to obtain the desired crystal form D, wherein the solvent is selected from the group consisting of water, an ester, an ether, an aliphatic hydrocarbon, an alicyclic hydrocarbon, a nitroalkane solvent, an arene, an alcohol, a nitrile, a halohydrocarbon, a ketone, a sulfoxide, an amide, a mixed solvent of an alcohol and an ether, a mixed solvent of an alcohol and water, and a mixed solvent of one or more alcohol, the ester solvent is selected from the group consisting of ethyl acetate, isopropyl acetate and butyl acetate, the ether solvent is selected from the group consisting of tetrahydrofuran, 1,4-dioxane, propylene glycol methyl ether and methyl tert-butyl ether, the aliphatic hydrocarbon is n-heptane, the alicyclic hydrocarbon is cyclohexane, the nitroalkane solvent is nitromethane, the arene solvent is selected from the group consisting of xylene and cumene, the alcohol solvent is selected from the group consisting of methanol, ethanol and isopropanol, the nitrile solvent is acetonitrile, the halohydrocarbon solvent is dichloromethane, the ketone solvent is acetone, the sulfoxide is dimethyl sulfoxide, the mixed solvent of one or more alcohol is selected from the group consisting of a mixed solvent of methanol and ethanol, a mixed solvent of methanol and isopropanol, and a mixed solvent of ethanol and isopropanol.

The present invention also provides a method for preparing the single crystal of crystal form D, characterized in that the method comprises the following steps of:

dissolving the compound of formula (I) in a solvent to crystallize, filtering and drying the resulting crystal to obtain the desired single crystal of crystal form D, wherein the solvent is a mixed solvent of an alcohol and water, the alcohol solvent is selected from the group consisting of methanol and ethanol; the ratio of the alcohol to water is 20:1-1:20, and preferably 6:1, and the crystallization method is selected from the group consisting of room temperature crystallization, cooling crystallization, solvent volatilization crystallization and crystallization induced by addition of a seed crystal.

The present invention also relates to a pharmaceutical composition of the crystal form A, B, C or D, characterized by further comprising one or more pharmaceutically acceptable carriers, diluents or excipients.

The present invention also relates to a use of the crystal form A, B, C or D, or the pharmaceutical composition in the preparation of a medicament for treating a disease associated with EZH2 inhibitor. According to the use of the present invention, the disease associated with EZH2 inhibitor is selected from the group consisting of lymphoma, leukemia, breast cancer, lung cancer, prostate cancer, ovarian cancer, liver cancer, melanoma, rhabdoid tumor, synovial sarcoma, mesothelioma, cervical cancer, colon cancer, rectal cancer, stomach cancer, pancreatic cancer, brain cancer, skin cancer, oral cancer, bone cancer, kidney cancer, bladder cancer, fallopian tube tumor, ovarian tumor, peritoneal tumor, glioma, glioblastoma, head and neck tumor and myeloma; preferably lymphoma, leukemia, breast cancer, lung cancer, prostate cancer, ovarian cancer, liver cancer, melanoma, rhabdoid tumor, synovial sarcoma and mesothelioma; the leukemia is preferably chronic myeloid leukemia, acute myeloid leukemia or mixed lineage leukemia; and the lymphoma is preferably non-Hodgkin lymphoma, diffuse large B-cell lymphoma or follicular lymphoma.

The resulting crystal forms of the compound of formula (I) are determined by X-ray powder diffraction spectrum (XRPD) and differential scanning calorimetry (DSC).

The recrystallization method for the crystal form is not particularly limited, and can be carried out by a conventional recrystallization process. For example, the material, i.e., the compound of formula (I), can be dissolved in an organic solvent followed by adding an anti-solvent to crystallize. After the completion of crystallization, the desired crystal can be obtained via filtering and drying.

The crystallization method of the present invention includes room temperature crystallization, cooling crystallization, solvent volatilization crystallization, crystallization induced by addition of a seed crystal and the like; and the cooling temperature is below 40° C., preferably from −10° C. to 40° C.

The starting material used in the method for preparing the crystal form of the present invention can be the compound of formula (I) in any form, and the specific forms include, but are not limited to, amorphous form, arbitrary crystal forms and the like.

Definitions

In the specification and claims of the present application, unless otherwise indicated, the scientific and technical terms used herein have the meanings generally understood by a person skilled in the art. However, in order to understand the present invention better, definitions and explanations of some related terms are provided. In addition, when the definitions and explanations of the terms provided in the present application are inconsistent with the meanings generally understood by a person skilled in the art, the definitions and explanations of the terms provided in the present application shall prevail.

The term "$C_{1-6}$alkyl" used in the present invention refers to a linear or branched alkyl containing 1 to 6 carbon atoms. Its specific examples include, but are not limited to: methyl, ethyl, n-propyl, isopropyl, n-butyl, isobutyl, sec-butyl, tent-butyl, n-pentyl, isopentyl, 2-methylbutyl, neo-pentyl, 1-ethylpropyl, n-hexyl, isohexyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3 -dimethylbutyl, 2-ethylbutyl, 1,2-dimethylpropyl and the like.

The term "ether solvent" used in the present invention refers to a chain compound or a cyclic compound having an ether bond —O— and having 1 to 10 carbon atoms. Its specific examples include, but are not limited to: tetrahydrofuran, diethyl ether, propylene glycol methyl ether, methyl tent-butyl ether and 1,4-dioxane.

The term "alcohol solvent" used in the present invention refers to a group derived from the substitution of one or more hydrogen atoms on the "$C_{1-6}$ alkyl" by one or more "hydroxy", wherein the "hydroxy" and "$C_{1-6}$ alkyl" are as defined above. Its specific examples include, but are not limited to: methanol, ethanol, isopropanol, n-propanol, isopentanol and trifluoroethanol.

The term "ester solvent" used in the present invention refers to a combination of a lower organic acid having 1 to 4 carbon atoms and a lower alcohol having 1 to 6 carbon atoms. Its specific examples include, but are not limited to: ethyl acetate, isopropyl acetate or butyl acetate.

The term "ketone solvent" used in the present invention refers to a compound in which a carbonyl group (—C(O)—) is bonded to two hydrocarbon groups. Ketones can be classified into aliphatic ketones, alicyclic ketones, aromatic ketones, saturated ketones, and unsaturated ketones, depending on the hydrocarbon group in the molecule. Its specific examples include, but are not limited to: acetone, acetophenone, methyl isobutyl ketone or methyl pyrrolidone.

The term "nitrile solvent" used in the present invention refers to a group derived from the substitution of one or more hydrogen atoms on the "$C_{1-6}$ alkyl" by one or more "cyano", wherein the "cyano" and "$C_{1-6}$ alkyl" are as defined above. Its specific examples include, but are not limited to: acetonitrile or propionitrile.

The term "aliphatic hydrocarbon solvent" used in the present invention refers to a hydrocarbon compound having the basic properties of an aliphatic compound and having 1 to 10 carbon atoms, wherein the carbon atoms in the molecule are linked to a chain-like carbon skeleton in which the two ends are opened and do not form a ring, for example saturated aliphatic hydrocarbon, including alkane solvent. Its specific examples include, but are not limited to: n-butane, n-pentane, n-hexane or n-heptane.

The term " alicyclic hydrocarbon solvent" used in the present invention refers to a hydrocarbon compound having similar properties to aliphatic hydrocarbon and having a cyclic carbon skeleton with 1 to 8 ring atoms. Its specific examples include, but are not limited to: cyclopentane and cyclohexane.

The term "amide solvent" used in the present invention refers to a compound having a carbonyl amino (—C(O)N—) and having 1 to 10 carbon atoms. Its specific examples include, but are not limited to: N,N-dimethylformamide and N,N-dimethylacetamide.

The term "arene solvent" used in the present invention refers to a general term for a carbon ring compound and a derivative thereof, wherein the molecule has a conjugated system of a closed ring, and the number of $\pi$ electrons conforms to the Huckel rule. Its specific examples include, but are not limited to: isopropylbenzene and xylene.

The term "halohydrocarbon solvent" used in the present invention refers to a group derived from "$C_{1-6}$alkyl" on which one or more hydrogen atoms are substituted by one or more "halogen atom", wherein the "halogen atom" and "$C_{1-6}$ alkyl" are as defined above. Its specific examples include, but are not limited to: methyl chloride, dichloromethane, chloroform and carbon tetrachloride.

The term "nitroalkane solvent" used in the present invention refers to a group derived from "$C_{1-6}$alkyl" on which one or more hydrogen atoms are substituted by one or more "nitro", wherein the "$C_{1-6}$alkyl" are as defined above. Its specific examples include, but are not limited to: nitromethane.

The term "mixed solvent" used in the present invention refers to a solvent obtained by mixing one or more different kinds of organic solvents in a certain ratio, or a solvent obtained by mixing an organic solvent and water in a certain ratio. The mixed solvent is preferably a mixed solvent of one or more alcohols, a mixed solvent of an alcohol and an ether, a mixed solvent of an alcohol and an aliphatic hydrocarbon, a mixed solvent of an ether and an aliphatic hydrocarbon, a mixed solvent of an alcohol and water, a mixed solvent of a halohydrocarbon and a nitrile, a mixed solvent of an amide and water, or a mixed solvent of an ether and water, wherein the alcohol, ether, aliphatic hydrocarbon, halohydrocarbon, amide and nitrile are as defined above.

The term "X-ray powder diffraction spectrum" or "XRPD" used in the present invention refers to a powder X-ray diffraction spectrum that is obtained according to the Bragg formula $2d \sin \theta = n\lambda$ (where $\lambda$ is the wavelength of the X-ray, $\lambda$=1.54056Å, the order of diffraction n is any positive integer, generally taking the first-order diffraction peak, n=1), when the X-ray is incident on a certain atomic plane of a crystal or a partial crystal sample having a d-lattice plane spacing at a glancing angle $\theta$ (the complementary angle of incidence angle, also called the Bragg angle), the Bragg equation can be satisfied.

The term "differential scanning calorimetry" or "DSC" used in the present invention means to measure the temperature difference and heat flow difference between the sample and the reference during the heating or constant temperature process of the sample, to characterize all physical and chemical changes associated with the thermal effect, and to obtain phase change information of the sample.

The term "2θ " or "2θ angle" used in the present invention refers to the diffraction angle, θ is the Bragg angle, and the unit of which is ° or degree. The error range of 2θ is from ±0.1 to ±0.5, preferably from ±0.1 to ±0.3, and more preferably ±0.2.

The term "interplanar spacing" or "interplanar distance (d value)" used in the present invention means that the space lattice selects three unparallel unit vectors a, b, c, wherein each of them connects two adjacent lattice dots, and the three vectors divide the lattice into juxtaposed parallel juxtagonal units, called the interplanar spacing. The space lattice is divided according to the determined parallelepiped unit lines to obtain a set of linear grids, which is called a space lattice or a lattice. The lattice reflects the periodicity of the crystal structure with geometric points and lines. Different crystal planes have different interplanar spacings (i.e., distance between two adjacent parallel crystal planes); the unit is Å or angstrom.

The present invention also relates to a pharmaceutical composition comprising the crystal form A, B, C or D of the compound of formula (I) and optionally one or more pharmaceutically acceptable carriers and/or diluents. The pharmaceutical composition can be formulated into any one of pharmaceutically acceptable dosage forms. For example, the crystal form A, B, C or D of the compound of formula (I) or the pharmaceutical formulation of the present invention can be formulated into a tablet, capsule, pill, granule, solution, suspension, syrup, injection (including injection solution, sterile powder for injection, and concentrated solution for injection), suppository, inhalant or spray.

In addition, the pharmaceutical composition of the present invention can also be administrated to a patient or subject in need of such treatment by any suitable administration mode, such as oral, parenteral, rectal, intrapulmonary or topical administration. For oral administration, the pharmaceutical composition can be formulated into an oral formulation, for example, an oral solid formulation such as a tablet, capsule, pill, granule and the like; or an oral liquid formulation such as an oral solution, oral suspension, syrup and the like. When formulated into an oral formulation, the pharmaceutical composition can further comprise a suitable filler, binder, disintegrator, lubricant and the like. For parenteral administration, the pharmaceutical composition can be formulated into an injection formulation including an injection solution, sterile powder for injection and concentrated solution for injection. When formulated into an injection formulation, the pharmaceutical composition can be produced by a conventional method in current pharmaceutical industry. When an injection formulation is formulated, an additional agent may not be added to the pharmaceutical formulation, or a suitable additional agent may be added depending on the nature of the medicament. For rectal administration, the pharmaceutical composition can be formulated into a suppository and the like. For intrapulmonary administration, the pharmaceutical composition can be formulated into an inhalant or spray and the like. In certain preferred embodiments, the crystal form A, B, C or D of the compound of formula (I) of the present invention is present in the pharmaceutical composition or medicament in a therapeutically and/or prophylactically effective amount. In certain preferred embodiments, the crystal form A, B, C or D of the compound of formula (I) of the present invention is present in the pharmaceutical composition or medicament in unit dose.

The crystal form A, B, C or D of the compound of formula (I) of the present invention can be used to prepare a medicament for treating a disease associated with EZH2 inhibitor. Therefore, the present application also relates to a use of the crystal form A, B, C or D of the compound of formula (I) of the present invention in the preparation of a medicament for treating a disease associated with EZH2 inhibitor. Moreover, the present application also relates to a method for inhibiting a disease associated with EZH2 inhibitor, comprising administering a therapeutically and/or prophylactically effective amount of the crystal form A, B, C or D of the compound of formula (I) of the present invention or the pharmaceutical composition of the present invention to a subject in need thereof.

In certain preferred embodiments, the disease is a disease associated with EZH2 inhibitor selected from pain.

Advantageous Effects of the Present Invention

Compared with the prior art, the technical solution of the present invention has the following advantages:

Studies have shown that the crystal forms A, B, C and D of the compound of formula (I) prepared according to present invention have a good stability and high purity. The single crystals of crystal forms A and D are obtained. The crystal forms A, B, C and D of the compound of formula (I) prepared by the technical solution of the present invention can meet the production, transportation and storage requirements of drug products. Its preparation process is stable, repeatable and controllable, and can be adapted to industrial production.

DETAILED DESCRIPTION OF THE INVENTION

Figure 1:
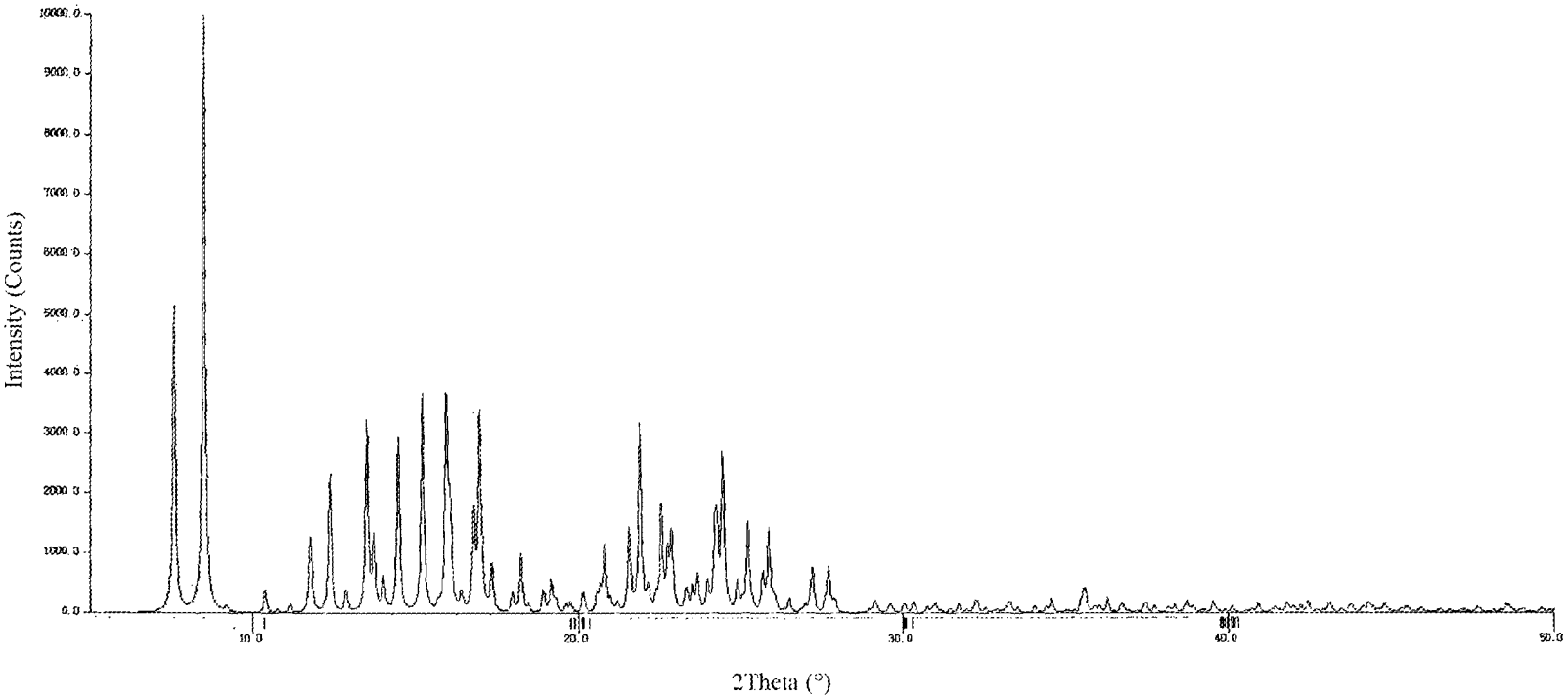
FIG. 1 shows the XRPD spectrum of crystal form A of the compound of formula (I).

The present invention will be illustrated by the following examples in detail. The examples of the present invention are merely intended to describe the technical solution of the present invention, and should not be considered as limiting the spirit and scope of the present invention.

Test conditions for the instruments used in the experiments:

1. Differential Scanning calorimeter, DSC

Instrument type: Mettler Toledo DSC3$^{+}$ STAR$^{e}$ System

Purging gas: Nitrogen (50 mL/min)

Heating rate: 10.0° C./min

Temperature range: 20-250° C.

2. X-ray Powder Diffraction, XRPD

Instrument type: BRUKER D8 Discover A25 X-ray powder diffractometer

Ray: monochromatic Cu—Kα ray (λ=1.5406 Å)

Scanning mode: θ/2,θ Scanning range: 10-48°

Voltage: 40 kV, Electric current: 40 mA

3. Dynamic Vapour Sorption, DVS

Instrument type: DVS advantage

Temperature: 25° C.

Solvent: water

Humidity change: 0-95-0-95-0% RH, dm/dt=0.002

Comparative Example 1.

Preparation method in Example 2 of WO2017084494 (PCT/CN2016/104318)

Preparation of

N-((4,6-dimethyl-2-oxo-1,2-dihydropyridin-3-yl)methyl)-5-ethyl-6-(ethyl(tetrahydro-2 H-pyran-4-yl)amino)-2-(piperidin-1-ylmethyl)benzofuran-4-carboxamide (the compound of formula (I))

(I)

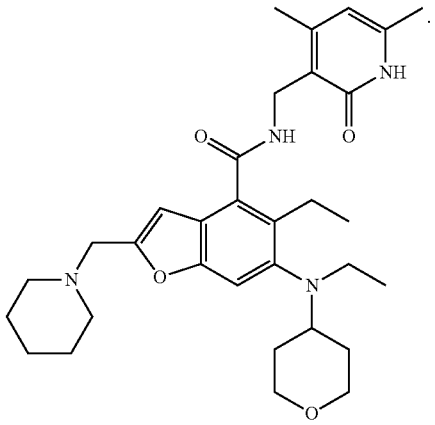

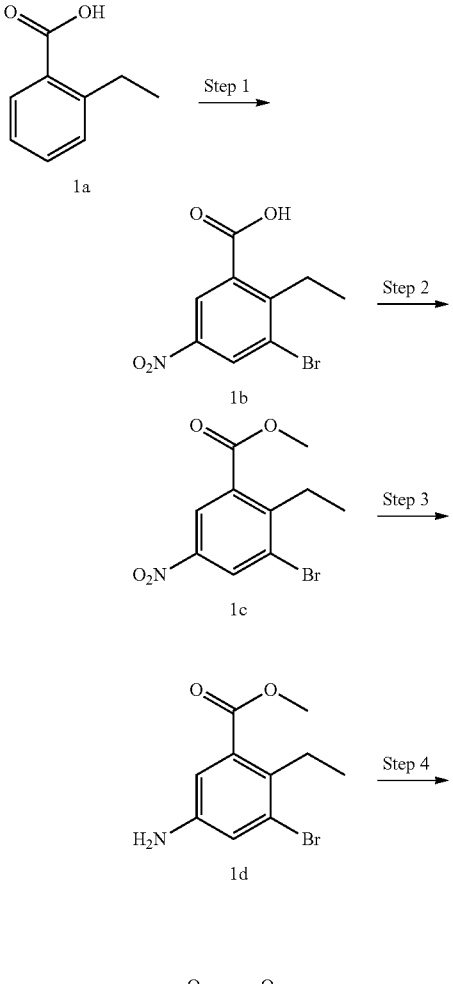

-continued
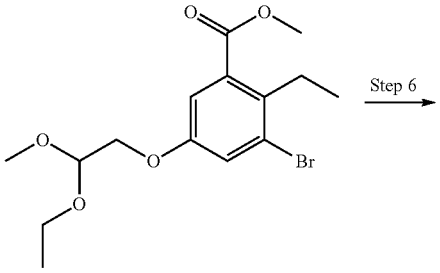
1f
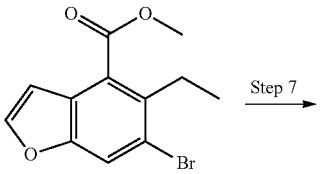
1g
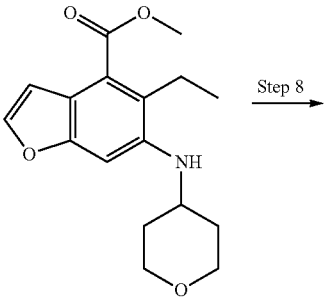
1h
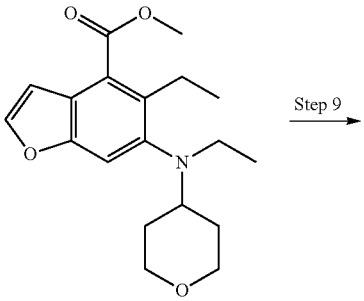
1i
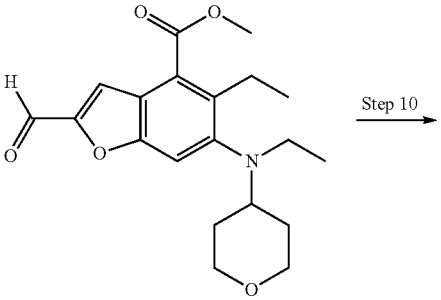
1j
-continued
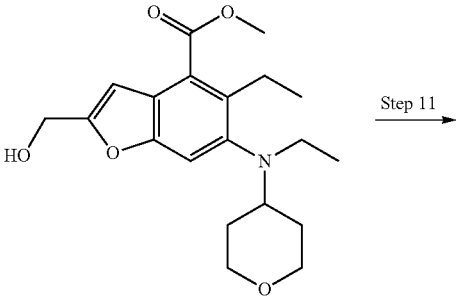
1k
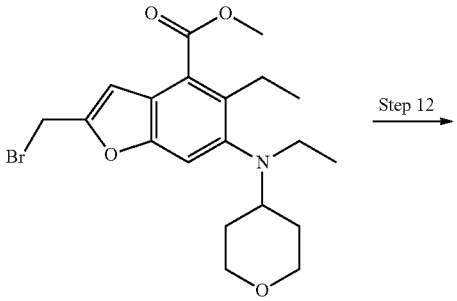
1l
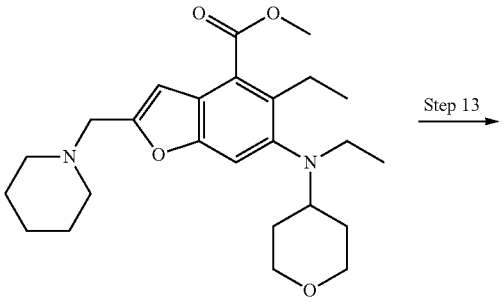
1m
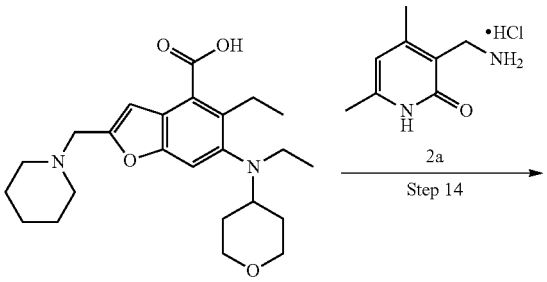
1n -continued

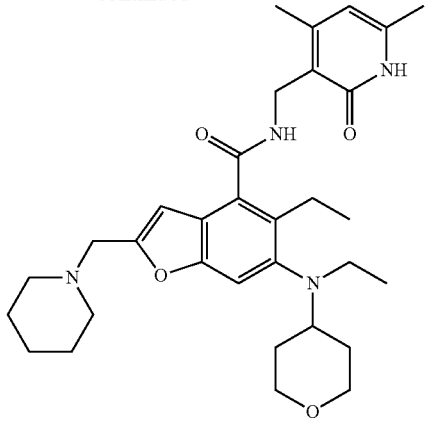

(I)

Step 1

3-Bromo-2-ethyl-5-nitrobenzoic acid 1b

2-Ethylbenzoic acid 1a (20.0 g, 133 mmol, prepared according to the method disclosed in "Journal of the American Chemical Society, 1991, 113(13), 4931-6") was added to 150 mL of sulfuric acid, and then sodium nitrate (11.3 g, 133 mmol) was added in batches in an ice bath. The reaction solution was stirred for 3 hours, and then N-bromosuccinimide (2.6 g, 14.5 mmol) was added in batches. The reaction mixture was stirred for 1 hour at 60° C. After the reaction was completed, the reaction solution was poured to ice water, stirred well and filtered. The filtrate was washed with water, and concentrated under reduced pressure to obtain the crude title product 3-bromo-2-ethyl-5-nitrobenzoic acid 1b (35 g) as a white solid, which was directly used in the next step without purification.

Step 2

Methyl 3-bromo-2-ethyl-5-nitrobenzoate 1c

The crude 3-bromo-2-ethyl-5-nitrobenzoic acid 1b (35 g, 128 mmol) was dissolved in 200 mL of N,N-dimethylformamide, then iodomethane (21.8 g, 153 mmol) and potassium carbonate (35.3 g, 255 mmol) were added. The reaction mixture was stirred for 2 hours at room temperature. After the reaction was completed, the reaction solution was concentrated under reduced pressure. The reaction solution was added with excess water, and extracted with ethyl acetate. The organic phases were combined, washed with water and saturated sodium chloride solution, dried over anhydrous sodium sulfate, and filtered. The filtrate was concentrated under reduced pressure to obtain the crude title product methyl 3-bromo-2-ethyl-5-nitrobenzoate 1c (36 g) as a yellow oil, which was directly used in the next step without purification.

Step 3

Methyl 5-amino-3-bromo-2-ethylbenzoate 1d

The crude methyl 3-bromo-2-ethyl-5-nitrobenzoate 1c (35.0 g, 121 mmol) was added to 250 mL of ethanol and 150 mL of water. The reaction solution was heated to 70° C., added with ammonium chloride (52.8 g, 969 mmol), then added with iron powder (34 g, 606 mmol) in batches. The reaction system was stirred for 2 hours at 70° C. After the reaction was completed, the reaction solution was filtered through celite while hot. The filter cake was washed with hot ethanol, then the filtrate was combined and concentrated under reduced pressure. Ethyl acetate and saturated sodium bicarbonate solution were added. Two phases were separated, and the aqueous phase was extracted with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with n-hexane and ethyl acetate as the eluent to obtain the title product methyl 5-amino-3-bromo-2-ethylbenzoate 1d (22.0 g, yield 70%) as a yellow solid.

Step 4

Methyl 3-bromo-2-ethyl-5-hydroxybenzoate 1e

Methyl 5-amino-3-bromo-2-ethylbenzoate 1d (15.0 g, 58 mmol) was dissolved in 10 mL of acetonitrile, then 200 mL of 10% sulfuric acid was added. The reaction solution was stirred well and cooled to 3° C. in an ice-salt bath, then added dropwise with 10 mL of a pre-prepared solution of sodium nitrite (4.4 g, 64 mmol). The reaction solution was stirred for 4 hours at the above temperature, added dropwise with 200 mL of 50% sulfuric acid, then stirred for 1 hour at 90° C. After the reaction was completed, the reaction solution was extracted three times with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with n-hexane and ethyl acetate as the eluent to obtain the title product methyl 3-bromo-2-ethyl-5-hydroxybenzoate 1e (5.5 g, yield 37%) as a brown solid.

Step 5

Methyl 3-bromo-5-(2,2-diethoxyethoxy)-2-ethylbenzoate 1f

Methyl 3-bromo-2-ethyl-5-hydroxybenzoate 1e (35 g, 135 mmol) was dissolved in 200 mL of N,N-dimethylformamide, then 2-bromo-1,1-diethoxyethane (40 g, 202 mmol) and potassium carbonate (37 g, 269 mmol) were added. The reaction system was stirred at 120° C. for 12 hours. After the reaction was completed, the reaction solution was concentrated under reduced pressure to remove N,N-dimethylformamide. The reaction solution was added with water, and extracted three times with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with n-hexane and ethyl acetate as the eluent to obtain the title product methyl 3-bromo-5-(2,2-diethoxyethoxy)-2-ethylbenzoate 1f (40 g, yield 80%) as a light yellow oil.

Step 6

Methyl 6-bromo-5-ethylbenzofuran-4-carboxylate 1g

Polyphosphoric acid (30 g) was added to 400 mL of toluene. The reaction solution was heated to 100° C., and added with 50 mL of a pre-prepared solution of methyl 3-bromo-5-(2,2-diethoxyethoxy)-2-ethylbenzoate 1f (40 g, 107 mmol) in toluene under stirring. The reaction solution was stirred for 16 hours at 100° C. After the reaction was completed, the supernatant was decanted. The residue was added with water and ethyl acetate. Two phases were separated, and the aqueous phase was extracted with ethyl acetate. The organic phases were combined, washed with saturated sodium carbonate solution and saturated sodium chloride solution, dried over anhydrous sodium sulfate, and filtered. The filtrate was concentrated under reduced pressure, and the resulting residue was purified by silica gel column chromatography with n-hexane and ethyl acetate as the eluent to obtain the title product methyl 6-bromo-5-ethylbenzofuran-4-carboxylate 1g (11.8 g, yield 39%) as a yellow solid.

Step 7

Methyl 5-ethyl-6-((tetrahydro-2H-pyran-4-y0amino) benzofuran-4-carboxylate 1h

Methyl 6-bromo-5-ethylbenzofuran-4-carboxylate ig (11.0 g, 39 mmol), tetrahydro-2H-pyran-4-amine (5.89 g, 58 mmol), tris(dibenzylideneacetone)dipalladium (3.6 g, 3.9 mmol), (0.9 mmol) bis(diphenylphosphino)-1,1'-binaphthalene (4.86 g, 7.8 mmol) and cesium carbonate (38 g, 117 mmol) were dissolved in 100 mL of toluene. The reaction solution was stirred for 12 hours at 100° C. After the reaction was completed, the reaction solution was filtered through celite, and the filter cake was washed with ethyl acetate. The organic phases were combined, dried over anhydrous sodium sulfate, and filtered. The filtrate was concentrated under reduced pressure, and the resulting residue was purified by silica gel column chromatography with n-hexane and ethyl acetate as the eluent to obtain the title product methyl 5-ethyl-6-((tetrahydro-2H-pyran-4-yl)amino)benzofuran-4-carboxylate 1h (10.0 g, yield 85%) as a yellow solid.

Step 8

Methyl 5-ethyl-6-(ethyl(tetrahydro-2H-pyran-4-y0amino)benzofuran-4-carboxylate 1i Methyl 5-ethyl-6-((tetrahydro-2H-pyran-4-yl)amino)benzofuran-4-carboxylate 1h (10.0 g, 0.033 mmol) was dissolved in 150 mL of 1,2-dichloroethane, then acetaldehyde (7.2 g, 0.165 mmol) and acetic acid (9.9 g, 0.165 mmol) were added. The reaction solution was stirred for 1 hour, and added with sodium triacetoxyborohydride (20.8 g, 0.1 mmol). The reaction solution was stirred for 12 hours at room temperature. After the reaction was completed, the reaction solution was concentrated under reduced pressure, neutralized with saturated sodium bicarbonate solution, and extracted with ethyl acetate.

The organic phases were combined, washed with saturated sodium chloride solution, dried over anhydrous sodium sulfate, and filtered. The filtrate was concentrated under reduced pressure, and the resulting residue was purified by silica gel column chromatography with n-hexane and ethyl acetate as the eluent to obtain the title product methyl 5-ethyl-6-(ethyl(tetrahydro-2H-pyran-4-yl)amino)benzofuran-4-carboxylate 1i (7.8 g, yield 71%) as a white solid.

MS m/z (LC-MS): 332.4 [M+1]

Step 9

Methyl 5-ethyl-6-(ethyl(tetrahydro-2H-pyran-4-yl) amino)-2-formylbenzofuran-4-carboxylate 1j Methyl 5-ethyl-6-(ethyl(tetrahydro-2H-pyran-4-yl) amino)benzofuran-4-carboxylate 1i (1.6 g, 4.8 mmol) was dissolved in 25 mL of tetrahydrofuran. The reaction solution was cooled to −70° C., and added dropwise with 2.0 M lithium diisopropylamide (3.6 mL, 7.3 mmol) under an argon atmosphere. The reaction solution was stirred for 90 minutes, and added with N,N-dimethylformamide (536 mg, 7.3 mmol). The reaction solution was stirred for 2 hours, then slowly warmed up to room temperature. The reaction solution was added with excess ammonium chloride, stirred well and extracted three times with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with n-hexane and ethyl acetate as the eluent to obtain the title product methyl 5-ethyl-6-(ethyl(tetrahydro-2H-pyran-4-yl)amino)-2-formylbenzofuran-4-carboxylate 1j (1.3 g, yield 75%) as a yellow oil.

MS m/z (ESI):360.2 [M+1]

Step 10

Methyl 5-ethyl-6-(ethyl(tetrahydro-2H-pyran-4-yl) amino)-2-(hydroxymethyl)benzofuran-4-carboxylate 1k Methyl 5-ethyl-6-(ethyl(tetrahydro-2H-pyran-4-yl) amino)-2-formylbenzofuran-4-carboxylate 1j (1.4 g, 3.9 mmol) was dissolved in 5 mL of tetrahydrofuran and 10 mL of methanol, then sodium borohydride (222 mg, 5.8 mmol) was added. The reaction solution was stirred for 30 minutes at room temperature. After the reaction was completed, the reaction solution was concentrated under reduced pressure, added with water and saturated sodium bicarbonate solution, and extracted three times with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with n-hexane and ethyl acetate as the eluent to obtain the title product methyl 5 -ethyl-6-(ethyl (tetrahydro-2H-pyran-4-yl)amino)-2-(hydroxymethyl)benzofuran-4-carboxylate 1k (1.4 g, yield 99%) as a yellow oil.

Step 11

Methyl 2-(bromomethyl)-5-ethyl-6-(ethyl(tetrahydro-2H-pyran-4-yl)amino)benzofuran-4-carboxylate 11

Methyl 5-ethyl-6-(ethyl(tetrahydro-2H-pyran-4-yl) amino)-2-(hydroxylmethyl) benzofuran-4-carboxylate 1k (1.0 g, 2.8 mmol) was dissolved in 30 mL of tetrahydrofuran, then phosphorus tribromide (1.12 g, 4.2 mmol) was added dropwise. The reaction solution was stirred for 12 hours at room temperature. After the reaction was completed, the reaction solution was neutralized with saturated sodium bicarbonate solution, and extracted with ethyl acetate three times. The organic phases were combined, washed with saturated sodium chloride solution, dried over anhydrous sodium sulfate, and filtered. The filtrate was concentrated under reduced pressure to obtain the crude title product methyl 2-(bromomethyl)-5-ethyl-6-(ethyl(tetrahydro-2H-pyran-4-yl)amino)benzofuran-4-carbo xylate 11 (1.15 g) as a yellow oil, which was directly used in the next step without purification.

Step 12

Methyl5-ethyl-6-(ethyl(tetrahydro-2H-pyran-4-yl) amino)-2-(piperidin-1-ylmethyl)benzofuran-4-carboxylate 1m The crude methyl 2-(bromomethyl)-5-ethyl-6-(ethyl(tetrahydro-2H-pyran-4-yl)amino)benzofuran-4-carbo xylate 11 (1.15 g, 2.7 mmol) was dissolved in 15 mL of acetonitrile, then 10 mL of a pre-prepared solution of piperidine (362 mg, 4.3 mmol) in acetonitrile were added dropwise. The reaction solution was stirred for 30 minutes at room temperature. After the reaction was completed, the reaction solution was concentrated under reduced pressure, and added with ethyl acetate and saturated sodium bicarbonate solution. Two phases were separated, and the aqueous phase was extracted with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with dichloromethane and methanol as the eluent to obtain the title product methyl 5 -ethyl-6-(ethyl(tetrahydro-2H-pyran-4-yl)amino)-2-(piperidin-1-ylmethyl)benzofuran-4-carboxylate 1m (1.2 g, yield 99%) as a yellow oil.

MS m/z (LC-MS): 429.2[M+1]

Step 13

5-Ethyl-6-(ethyl(tetrahydro-2H-pyran-4-yl)amino)-2-(piperidin-1-ylmethyl)benzofuran-4-carboxylic acid 1n Methyl 5-ethyl-6-(ethyl(tetrahydro-2H-pyran-4-yl) amino)-2-(piperidin-1-ylmethyl) benzofuran-4-carboxylate 1m (1.2 g, 2.7 mmol) was dissolved in 5 mL of tetrahydrofuran and 20 mL of methanol, then 5 mL of 4 M sodium hydroxide solution were added. The reaction solution was stirred for 12 hours at 60° C. After the reaction was completed, concentrated hydrochloric acid was added to adjust the pH of the reaction solution to 4. The mixture was concentrated under reduced pressure, and the residue was dissolved in a mixed solvent of dichloromethane and methanol (V:V=5:1) and filtered. The filter cake was washed with a mixed solvent of dichloromethane and methanol (V:V=5:1). The filtrates were combined, and concentrated under reduced pressure to obtain the crude title product 5-ethyl-6-(ethyl(tetrahydro-2H-pyran-4-yl)amino)-2-(piperidin-1-ylmethyl)benzofuran-4-carboxylic acid 1n (1.1 g) as a yellow solid, which was directly used in the next step without purification.

MS m/z (LC-MS): 415.2[M+1]

Step 14

N-((4,6-dimethyl-2-oxo-1,2-dihydropyridin-3 -yl) methyl)5-ethyl-6-(ethyl(tetrahydro-2H-pyran-4-yl)amino)-2-(piperidin-1-ylmethyl)benzofuran-4-carboxamide (the compound of formula (I)) 5-Ethyl-6-(ethyl(tetrahydro-2H-pyran-4-yl)amino)-2-(piperidin-1-ylmethyl)benzof uran-4-carboxylic acid in (1.0 g, 2.4 mmol) was dissolved in 30 mL of N,N-dimethylformamide, then 1-ethyl-3-(3-dimethylaminopropyl)carbodiimide (696 mg, 3.6 mmol), 1-hydroxybenzotriazole (490 mg, 3.6 mmol) and N,N-diisopropylethylamine (1.56 g, 12.1 mmol) were added. The reaction solution was stirred for 1 hour, then added with 3-(aminomethyl)-4,6-dimethylpyridin-2(1H)-one hydrochloride 2a (593 mg, 3.0 mmol, prepared according to the method disclosed in the patent application "WO2014097041"). The reaction solution was stirred for 12 hours at room temperature. After the reaction was completed, the reaction solution was added with excess water, and extracted with a mixed solvent of dichloromethane and methanol (V:V=8:1). The organic phases were combined, washed with water and saturated sodium chloride solution, dried over anhydrous sodium sulfate, and filtered. The filtrate was concentrated under reduced pressure, and the resulting residue was purified by silica gel column chromatography with dichloromethane and methanol as the eluent to obtain the title product N-((4,6-dimethyl-2-oxo-1,2-dihy dropyridin-3 -yl)methyl)-5-ethyl-6-(ethyl(tetrahy dro-2 H-pyran-4-yl)amino)-2-(piperidin-1-ylmethyl)benzofuran-4-carboxamide (I) (750 mg, yield 57%) as a white solid.

MS m/z (ESI): 549.7 [M+1]

Figure 17:
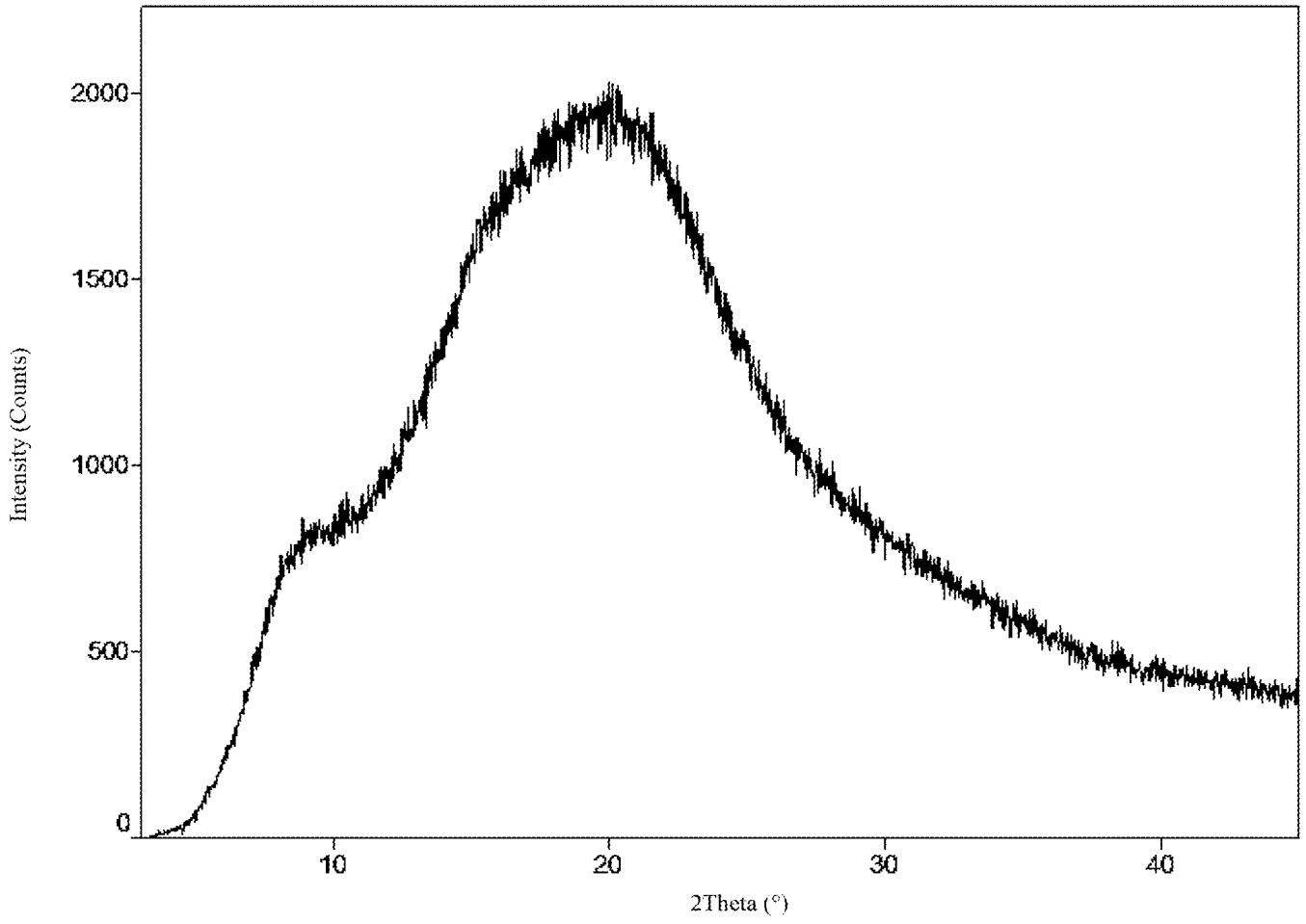
FIG. 17 shows the XRPD spectrum of amorphous form of the compound of formula (I).

The white solid product was identified as amorphous form by XRPD spectrum. The XRPD spectrum of the amorphous form is shown in FIG. 17.

EXAMPLE 1

Preparation of Crystal Form A

The crude produfct N-((4,6-dimethyl-2-oxo-1,2-dihy dropyridin-3 -yl)methyl)-5-ethyl-6-(ethyl(tetrahydro-2 H-pyran-4-yl)amino)-2-(piperidin-1-ylmethyl)benzofuran-4-carboxamide (20 mg, 0.036 mmol) obtained in Comparative example 1 was added to a reaction flask, and a mixed solvent of dichloromethane-acetonitrile (v:v, 1:10, 500 μL) was added. The reaction solution was stirred at 25° C. for one hour, and filtrated. The filtrate was placed in a clean flask, and slowly volatilized until the solvent was completely dried to obtain a white to pale yellow solid. The XRPD spectrum of the solid sample is shown in FIG. 1, and the characteristic peak positions are shown in the following table:

TABLE 1

Characteristic peaks of crystal form A

| Peak No. | 2θ[°] | d[Å] |
|---|---|---|
| Peak 1 | 7.60 | 11.62 |
| Peak 2 | 8.51 | 10.38 |
| Peak 3 | 10.37 | 8.53 |
| Peak 4 | 11.16 | 7.92 |
| Peak 5 | 11.80 | 7.5 |
| Peak 6 | 12.38 | 7.14 |
| Peak 7 | 12.89 | 6.86 |
| Peak 8 | 13.52 | 6.55 |
| Peak 9 | 13.73 | 6.44 |
| Peak 10 | 14.03 | 6.31 |
| Peak 11 | 14.48 | 6.11 |
| Peak 12 | 15.23 | 5.81 |
| Peak 13 | 15.99 | 5.54 |
| Peak 14 | 16.10 | 5.5 |
| Peak 15 | 16.43 | 5.39 |
| Peak 16 | 16.82 | 5.27 |
| Peak 17 | 16.99 | 5.21 |

TABLE 1-continued

| Characteristic peaks of crystal form A | | |
|---|---|---|
| Peak No. | 2θ[°] | d[Å] |
| Peak 18 | 17.35 | 5.11 |
| Peak 19 | 18.24 | 4.86 |
| Peak 20 | 18.92 | 4.69 |
| Peak 21 | 19.17 | 4.63 |
| Peak 22 | 20.68 | 4.29 |
| Peak 23 | 20.82 | 4.26 |
| Peak 24 | 21.57 | 4.12 |
| Peak 25 | 21.91 | 4.05 |
| Peak 26 | 22.57 | 3.94 |
| Peak 27 | 22.76 | 3.90 |
| Peak 28 | 22.88 | 3.88 |
| Peak 29 | 23.53 | 3.78 |
| Peak 30 | 23.68 | 3.75 |
| Peak 31 | 24.00 | 3.71 |
| Peak 32 | 24.29 | 3.66 |
| Peak 33 | 24.47 | 3.64 |
| Peak 34 | 24.91 | 3.57 |
| Peak 35 | 25.24 | 3.53 |
| Peak 36 | 25.72 | 3.46 |
| Peak 37 | 25.90 | 3.44 |
| Peak 38 | 27.23 | 3.27 |
| Peak 39 | 27.74 | 3.21 |
| Peak 40 | 35.63 | 2.52 |

EXAMPLE 2

Preparation of Single Crystal of Crystal Form A

Figure 15:
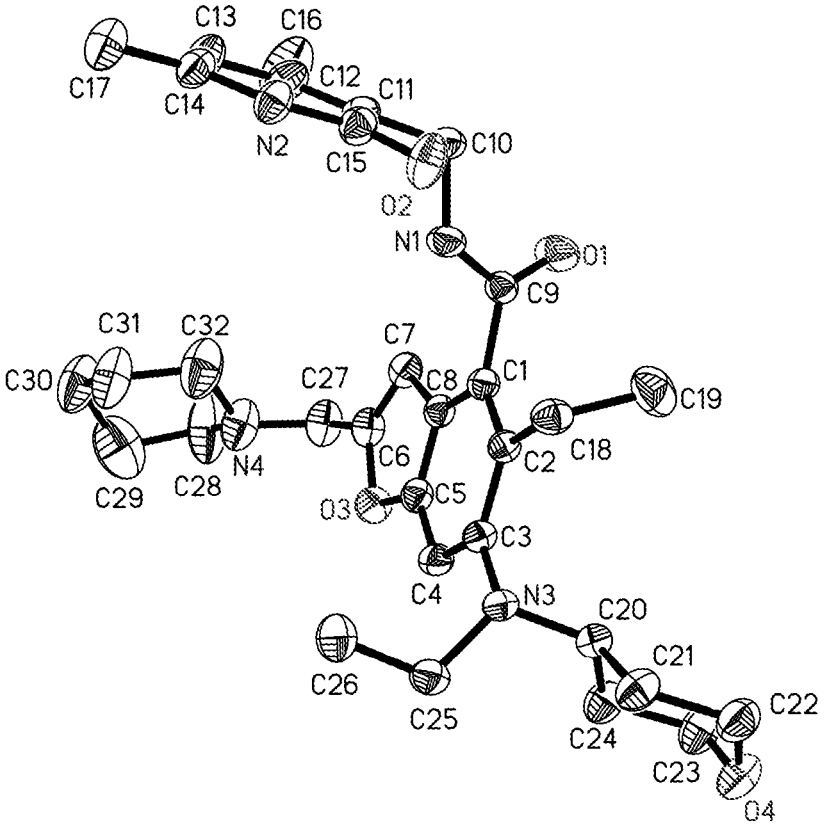
FIG. 15 shows the X-ray single crystal diffraction molecular stereostructure diagram of crystal form A of the compound of formula (I).

The crude product N-((4,6-dimethyl-2-oxo-1,2-dihy dropyridin-3 -yl)methyl)-5-ethyl-6-(ethyl(tetrahy dro-2 H-pyran-4-yl)amino)-2-(piperidin-1-ylmethyl)benzofuran-4-carboxamide (30 mg, 0.055 mmol) obtained in Comparative example 1 was added to a reaction flask, and dissolved in a mixed solvent of acetonitrile and dichloromethane (v/v, 10:1, 1 mL). The mouth of the flask was sealed by a sealing film which was punctured two to three small holes. The solvent was volatilized to obtain a single crystal. The single molecular stereostructure of the crystal sample is shown in FIG. 15 by single crystal X-ray diffraction (XRD), and the unit cell parameters are shown in the following table:

TABLE 2

| Unit cell parameters of single crystal of crystal form A | | |
|---|---|---|
| Parameters | | Values |
| Crystal system | | Orthorhombic crystal system |
| Space group | | P bca |
| Unit cell parameters | a (Å) | 17.051(3) |
| | b (Å) | 15.840(3) |
| | c (Å) | 23.2549(5) |
| | α (°) | 90.0 |
| | β (°) | 90.0 |
| | γ (°) | 90.0 |
| Unit cell volume V ($Å^3$) | | 6279(2) |
| Z (Asymmetric unit number in unit cell) | | 8 |
| Calculated density ($g/cm^3$) | | 1.161 |

EXAMPLE 3

Preparation of Crystal Form B

Figure 2:
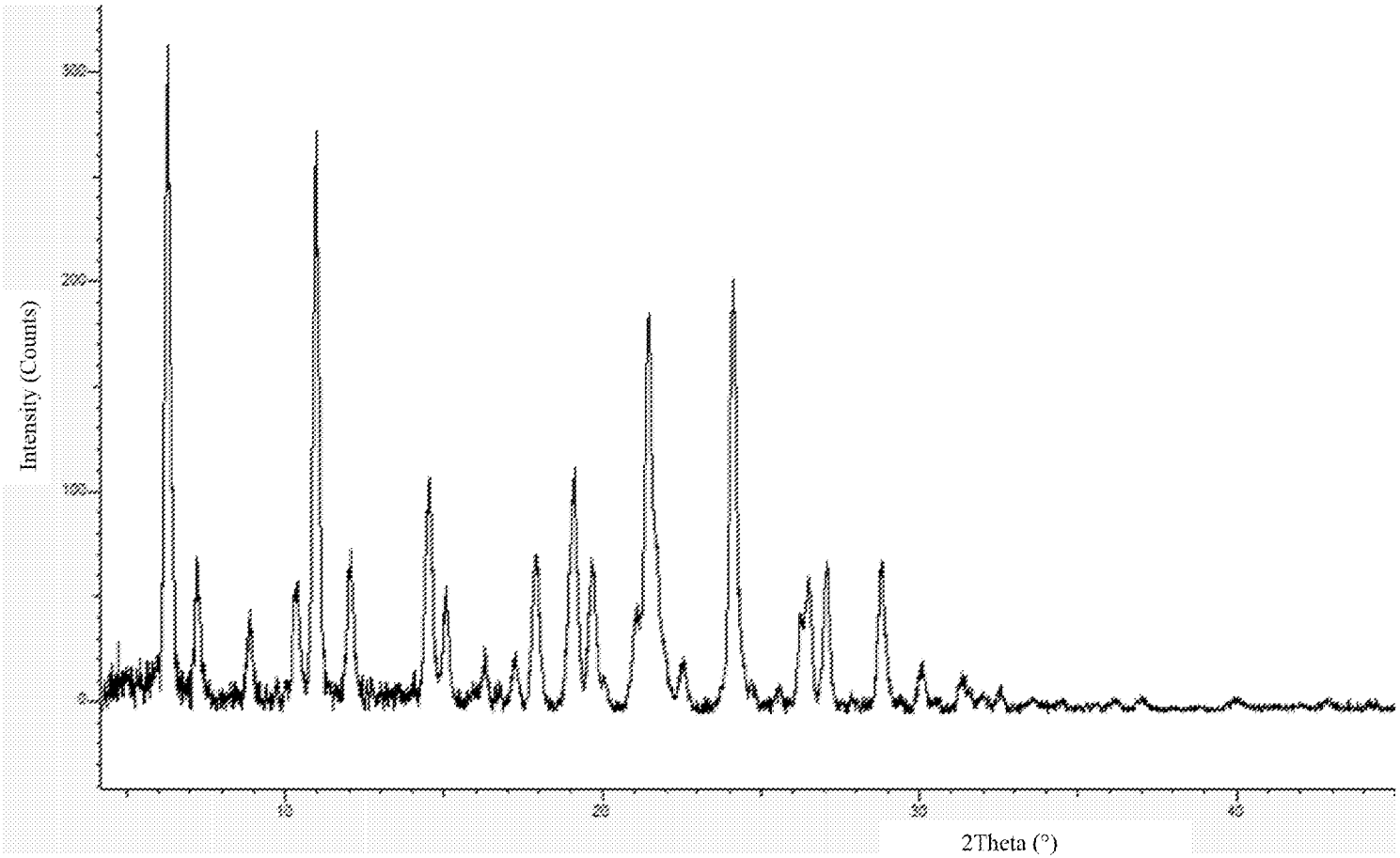
FIG. 2 shows the XRPD spectrum of crystal form B of the compound of formula (I).
Figure 3:
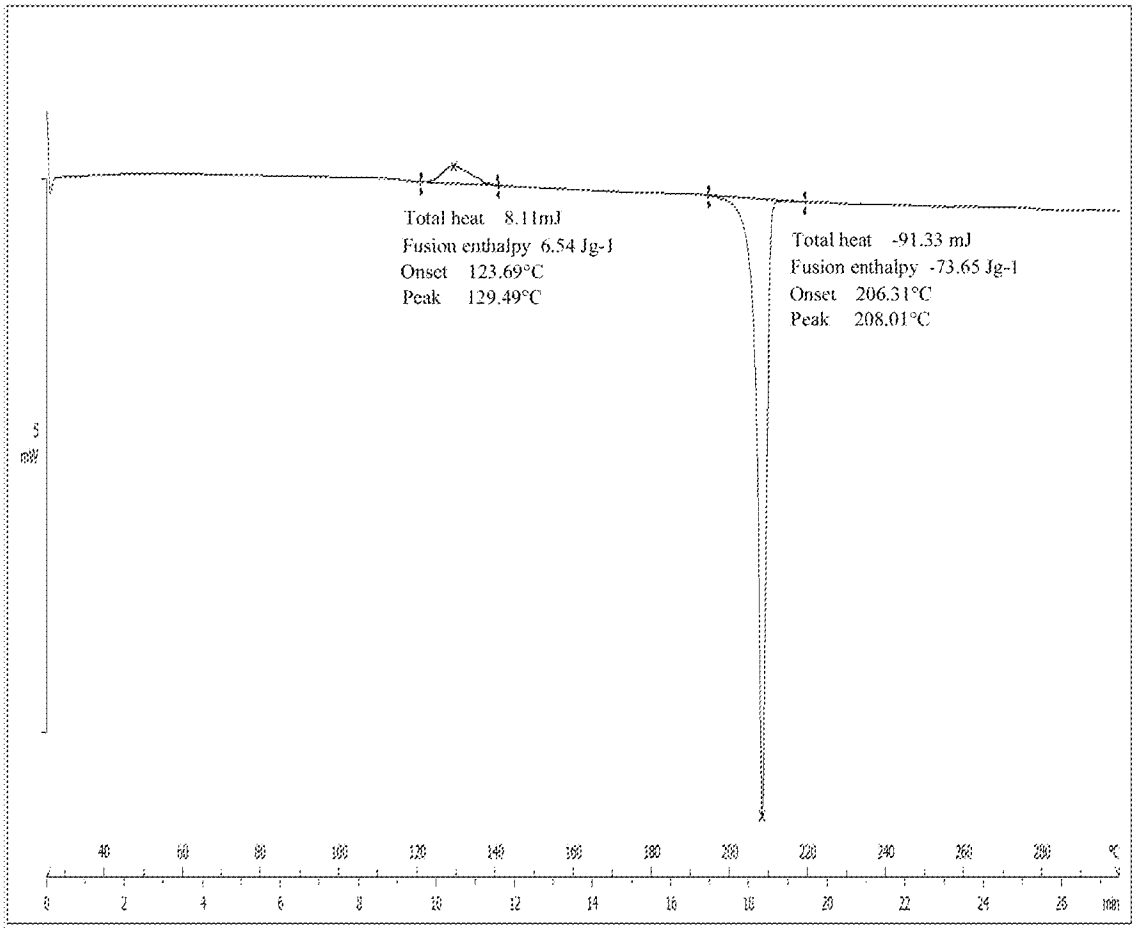
FIG. 3 shows the DSC spectrum of crystal form B of the compound of formula (I).

The crude product N-((4,6-dimethyl-2-oxo-1,2-dihy dropyridin-3 -yl)methyl)-5 -ethyl-6-(ethyl(tetrahy dro-2 H-pyran-4-yl)amino)-2-(piperidin-1-ylmethyl)benzofuran-4-carboxamide (30 mg, 0.055 mmol) obtained in Comparative example 1 was added to a reaction flask, and dissolved in ethanol (300 μL). The mouth of the flask was sealed by a sealing film which was punctured two to three small holes. The solution was placed still at room temperature until the solvent volatilized to dryness to obtain a white to pale yellow solid. The XRPD spectrum of the crystal sample is shown in FIG. 2. The DSC spectrum is shown in FIG. 3, in which there are one endothermic peak and one exothermic during the temperature-rise period, the onset of the exothermic peak is at about 123.69° C., and the onset melting temperature is about 206.31° C. The crystal form was defined as crystal form B, and the characteristic peak positions are shown in the following table:

TABLE 3

| Characteristic peaks of crystal form B | | |
|---|---|---|
| Peak No. | 2θ[°] | d[Å] |
| Peak 1 | 6.31 | 13.99 |
| Peak 2 | 7.24 | 12.19 |
| Peak 3 | 8.92 | 9.90 |
| Peak 4 | 10.38 | 8.52 |
| Peak 5 | 10.99 | 8.04 |
| Peak 6 | 12.07 | 7.33 |
| Peak 7 | 14.56 | 6.08 |
| Peak 8 | 15.10 | 5.86 |
| Peak 9 | 16.36 | 5.42 |
| Peak 10 | 17.29 | 5.12 |
| Peak 11 | 17.94 | 4.94 |
| Peak 12 | 19.13 | 4.64 |
| Peak 13 | 19.71 | 4.50 |
| Peak 14 | 21.12 | 4.20 |
| Peak 15 | 21.48 | 4.13 |
| Peak 16 | 22.59 | 3.93 |
| Peak 17 | 24.15 | 3.68 |
| Peak 18 | 25.45 | 3.50 |
| Peak 19 | 26.28 | 3.39 |
| Peak 20 | 26.52 | 3.36 |
| Peak 21 | 27.10 | 3.29 |
| Peak 22 | 28.83 | 3.09 |
| Peak 23 | 30.07 | 2.97 |
| Peak 24 | 31.37 | 2.85 |
| Peak 25 | 32.56 | 2.75 |
| Peak 26 | 33.65 | 2.66 |
| Peak 27 | 34.64 | 2.59 |
| Peak 28 | 36.09 | 2.49 |
| Peak 29 | 37.13 | 2.42 |
| Peak 30 | 40.04 | 2.25 |

EXAMPLE 4

Preparation of Crystal Form B

The crude product N-((4,6-dimethyl-2-oxo-1,2-dihy dropyridin-3 -yl)methyl)-5 -ethyl-6-(ethyl(tetrahy dro-2 H-pyran-4-yl)amino)-2-(piperidin-1-ylmethyl)benzofuran-4-carboxamide (30 mg, 0.055 mmol) obtained in Comparative example 1 was added to a reaction flask, and dissolved in ethanol (300 μL). The solution was added with water (900 μL) as an anti-solvent to precipitate a crystal. The mixture was filtered and dried to obtain a pale yellow solid. The crystal sample was identified as crystal form B by XRPD.

EXAMPLE 5

Preparation of Crystal Form C

Figure 4:
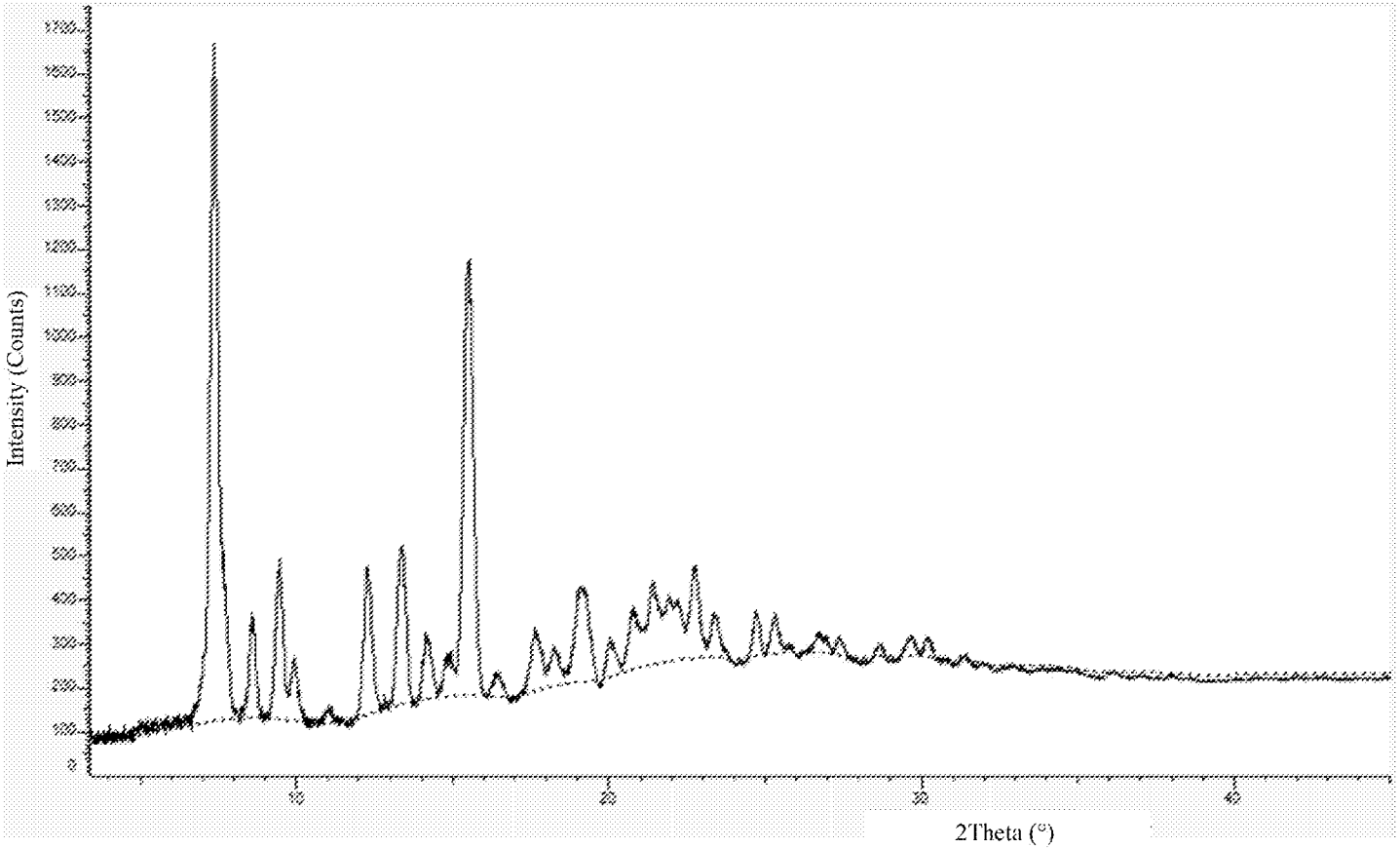
FIG. 4 shows the XRPD spectrum of crystal form C of the compound of formula (I).
Figure 5:
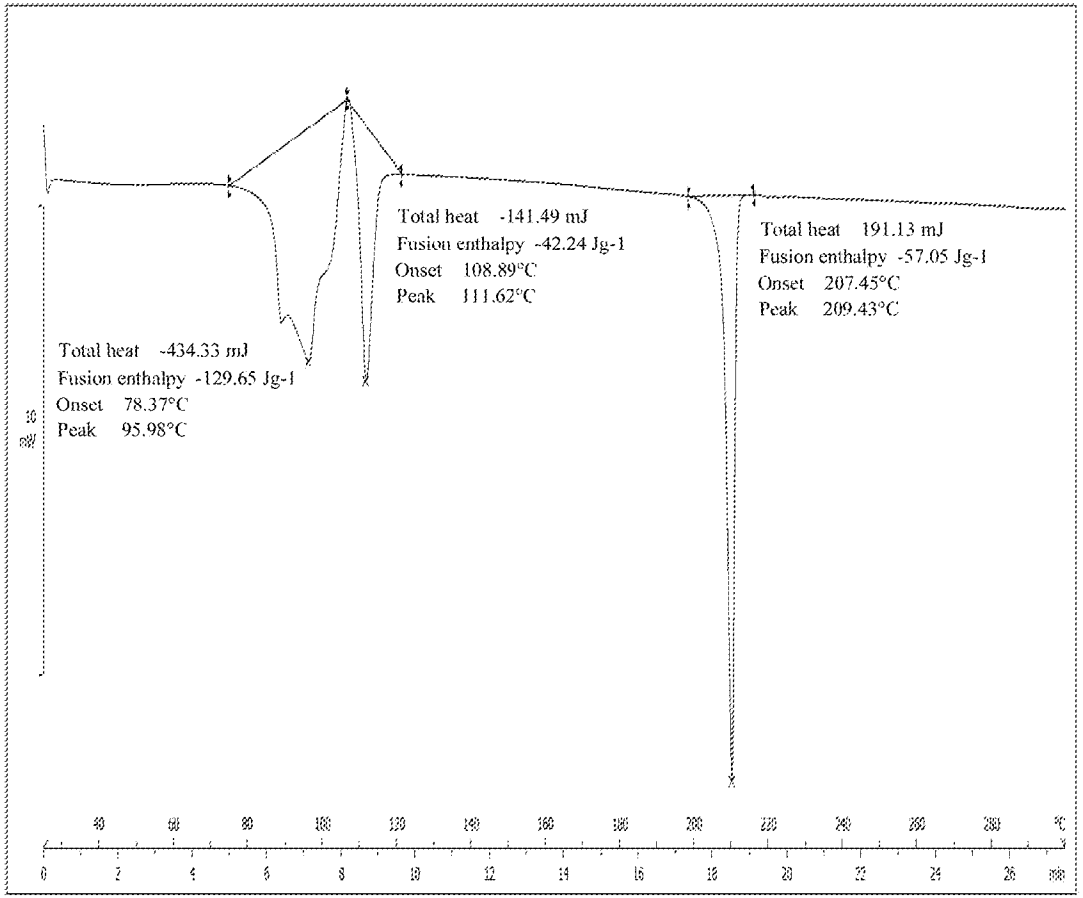
FIG. 5 shows the DSC spectrum of crystal form C of the compound of formula

The crude product N-((4,6-dimethyl-2-oxo-1,2-dihydropyridin-3 -yl)methyl)-5 -ethyl-6-(ethyl(tetrahydro-2 H-pyran-4-yl)amino)-2-(piperidin-1-ylmethyl)benzofuran- 4-carboxamide (30 mg, 0.055 mmol) obtained in Comparative example 1 was added to a reaction flask, and dissolved in 1,4-dioxane (1 mL). The solution was added with n-heptane (2 mL) to precipitate a crystal. The mixture was filtered and dried to obtain a white to pale yellow powder. The XRPD spectrum of the crystal sample is shown in FIG. 4. The DSC spectrum is shown in FIG. 5, in which there are multiple endothermic peaks. The crystal form was defined as crystal form C, and the characteristic peak positions are shown in the following table:

TABLE 4

Characteristic peaks of crystal form C

| Peak No. | 2θ[°] | d[Å] |
|---|---|---|
| Peak 1 | 7.40 | 11.93 |
| Peak 2 | 8.62 | 10.25 |
| Peak 3 | 9.49 | 9.32 |
| Peak 4 | 9.96 | 8.88 |
| Peak 5 | 11.12 | 7.95 |
| Peak 6 | 12.32 | 7.18 |
| Peak 7 | 13.39 | 6.61 |
| Peak 8 | 14.21 | 6.23 |
| Peak 9 | 14.85 | 5.96 |
| Peak 10 | 15.52 | 5.71 |
| Peak 11 | 16.50 | 5.37 |
| Peak 12 | 17.67 | 5.01 |
| Peak 13 | 18.28 | 4.85 |
| Peak 14 | 19.15 | 4.63 |
| Peak 15 | 19.17 | 4.63 |
| Peak 16 | 20.06 | 4.42 |
| Peak 17 | 20.80 | 4.27 |
| Peak 18 | 21.42 | 4.15 |
| Peak 19 | 21.89 | 4.06 |
| Peak 20 | 22.20 | 4.00 |
| Peak 21 | 22.78 | 3.90 |
| Peak 22 | 23.41 | 3.80 |
| Peak 23 | 24.74 | 3.60 |
| Peak 24 | 25.34 | 3.51 |
| Peak 25 | 26.70 | 3.34 |
| Peak 26 | 27.38 | 3.25 |
| Peak 27 | 28.64 | 3.11 |
| Peak 28 | 29.63 | 3.01 |
| Peak 29 | 30.20 | 2.96 |
| Peak 30 | 31.15 | 2.87 |

EXAMPLE 6

Preparation of Crystal Form D

Figure 6:
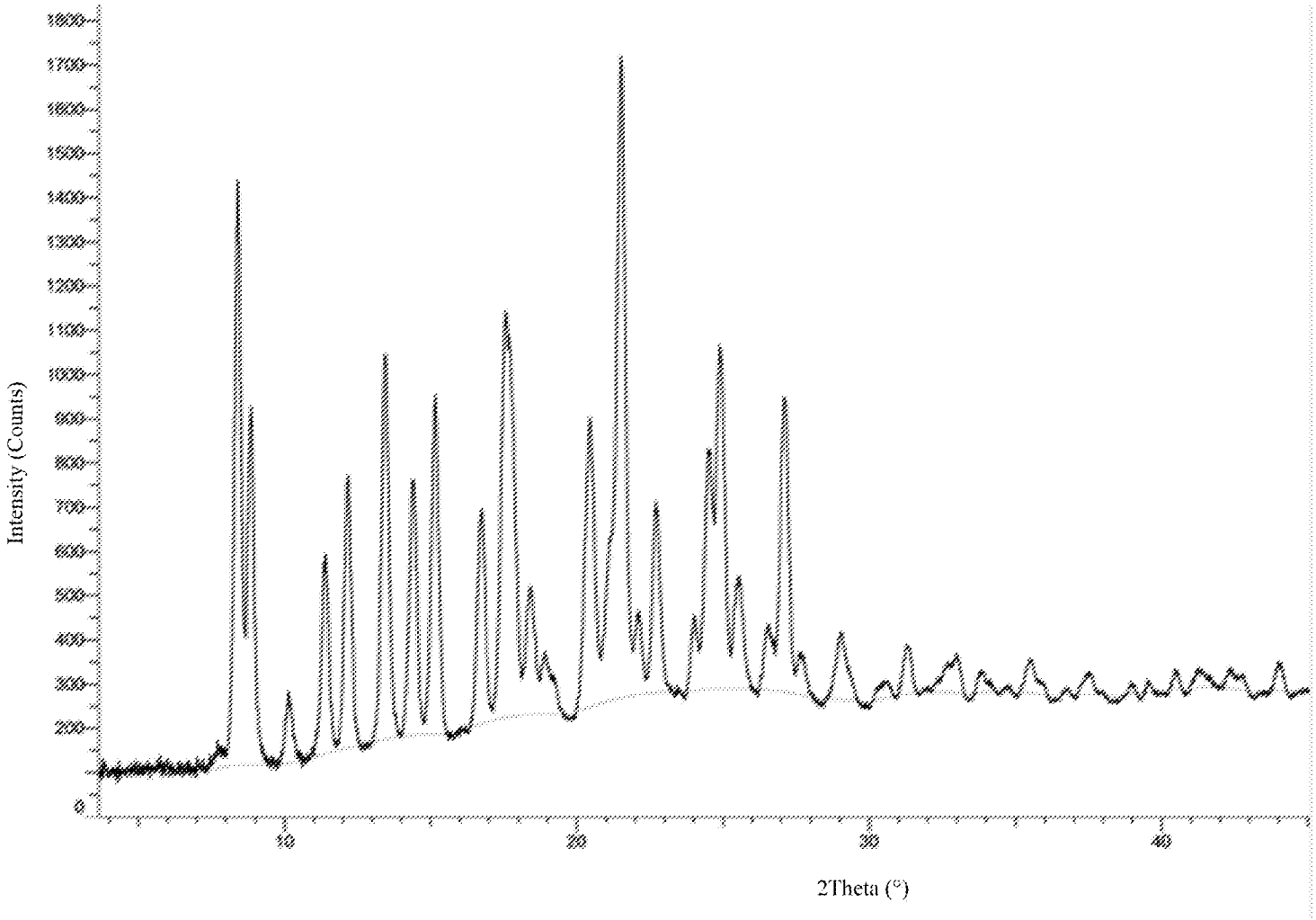
FIG. 6 shows the XRPD spectrum of crystal form D of the compound of formula
Figure 7:
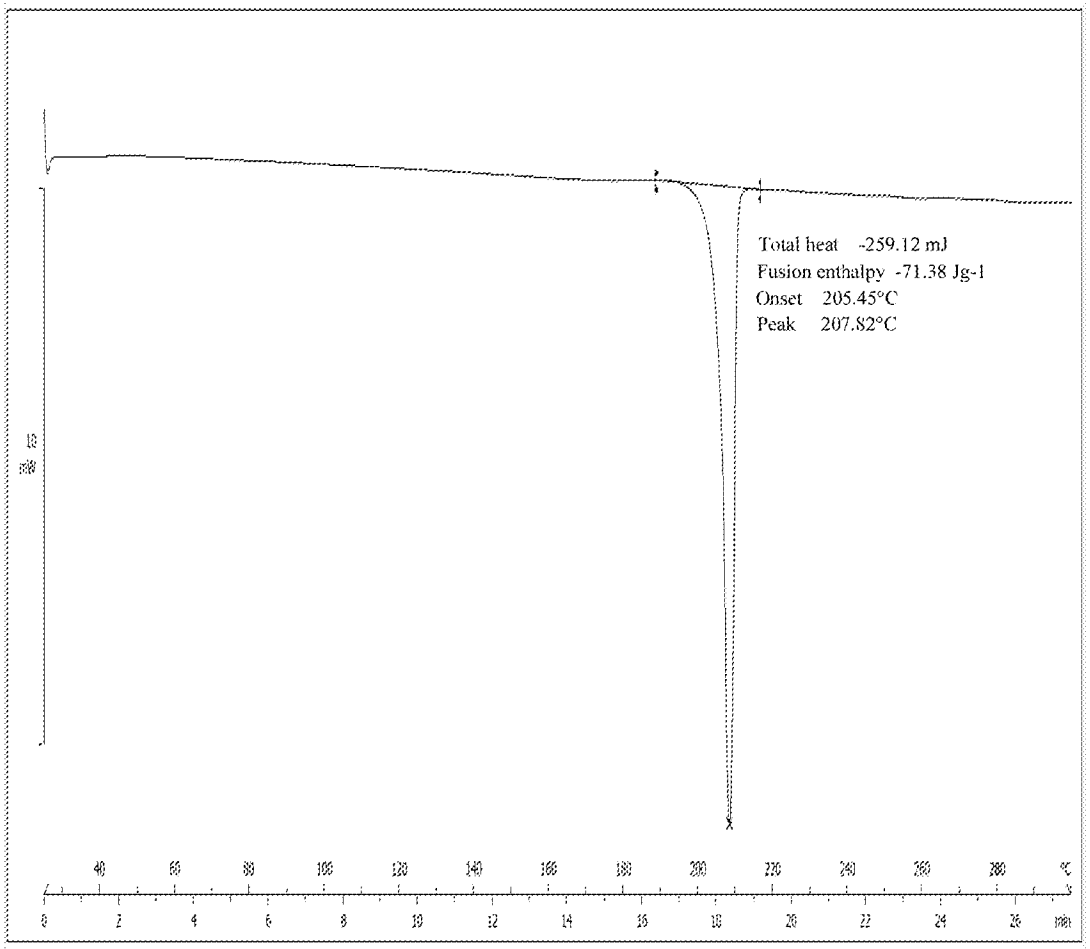
FIG. 7 shows the DSC spectrum of crystal form D of the compound of formula
Figure 8:
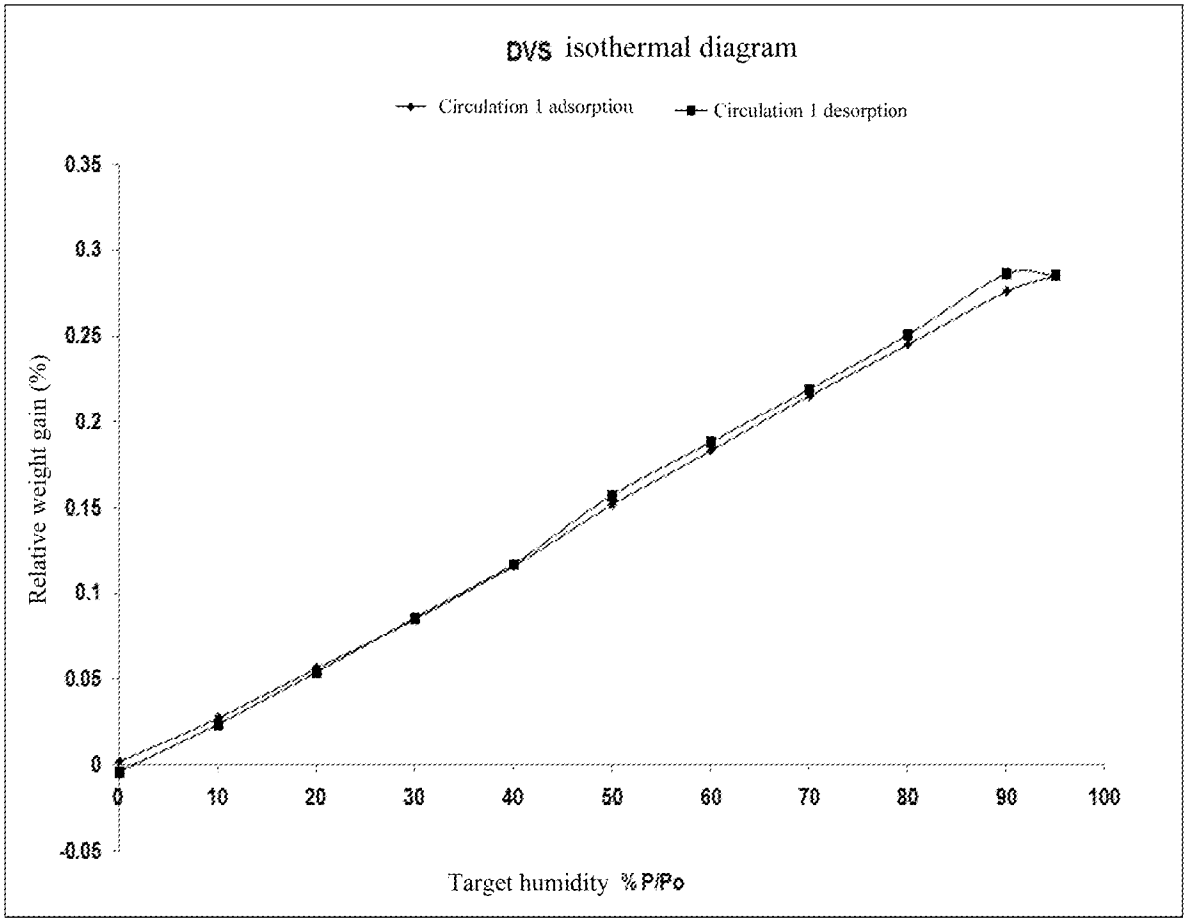
FIG. 8 shows the DVS circulation 1 diagram of crystal form D of the compound of formula (I).
Figure 9:
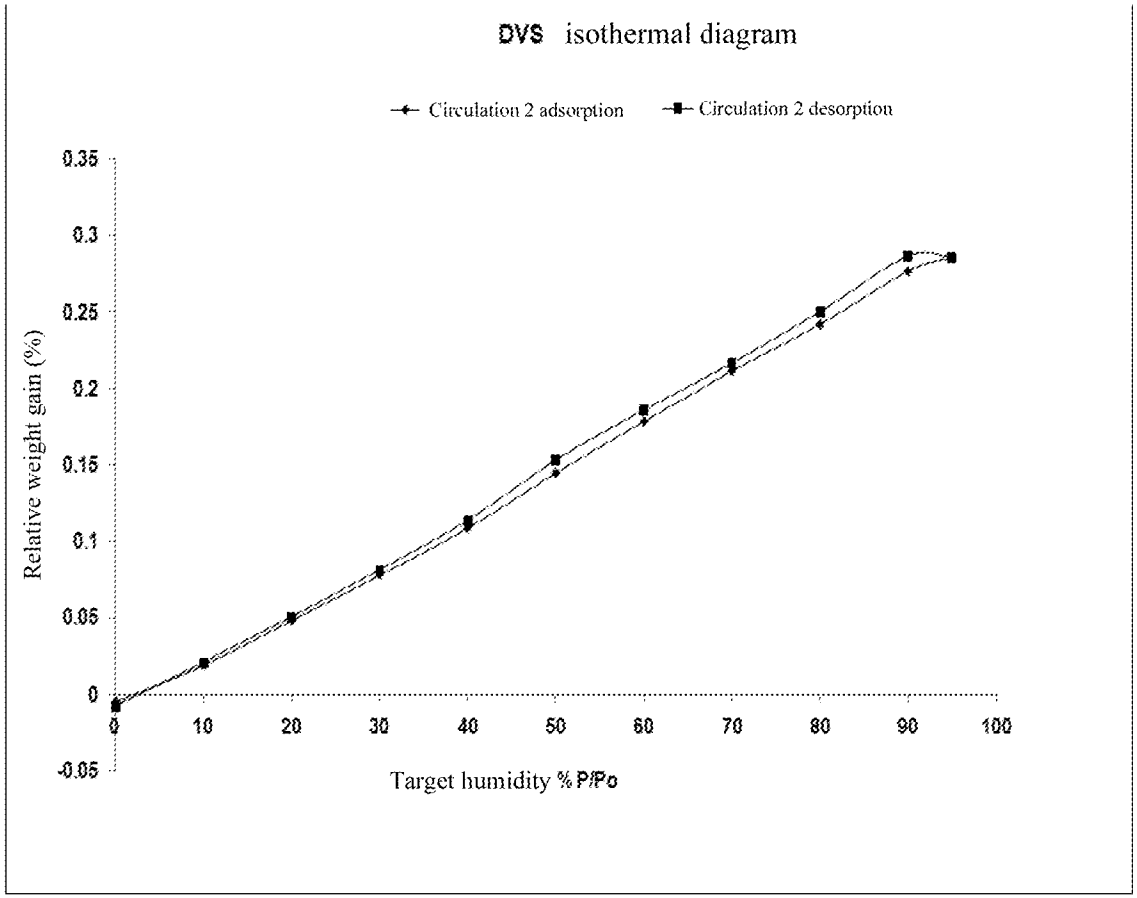
FIG. 9 shows the DVS circulation 2 diagram of crystal form D of the compound of formula (I).

The crude product N-((4,6-dimethyl-2-oxo-1,2-dihydropyridin-3 -yl)methyl)-5 -ethyl-6-(ethyl(tetrahydro-2 H-pyran-4-yl)amino)-2-(piperidin-1-ylmethyl)benzofuran-4-carboxamide (50 mg, 0.091 mmol) obtained in Comparative example 1 was added to a reaction flask, and methanol (100 μL) was added. The solution was stirred at 25° C. for five days, filtrated and dried under vacuum to obtain a white to pale yellow powder. The XRPD spectrum of the crystal sample is shown in FIG. 6. The DSC spectrum is shown in FIG. 7, in which the onset melting temperature is about 205.45° C. The crystal form was defined as crystal form D. It can be seen from the DVS diagrams of FIGS. 8 and 9 that the crystal form D has no obvious hygroscopicity. The characteristic peak positions are shown in the following table:

TABLE 5

Characteristic peaks of crystal form D

| Peak No. | 2θ[°] | d[Å] |
|---|---|---|
| Peak 1 | 8.41 | 10.50 |
| Peak 2 | 8.85 | 9.98 |
| Peak 3 | 10.15 | 8.71 |
| Peak 4 | 11.38 | 7.77 |
| Peak 5 | 12.18 | 7.26 |
| Peak 6 | 13.45 | 6.58 |
| Peak 7 | 14.40 | 6.14 |
| Peak 8 | 15.15 | 5.84 |
| Peak 9 | 16.73 | 5.29 |
| Peak 10 | 17.59 | 5.04 |
| Peak 11 | 17.68 | 5.01 |
| Peak 12 | 18.42 | 4.81 |
| Peak 13 | 18.91 | 4.69 |
| Peak 14 | 19.22 | 4.61 |
| Peak 15 | 20.45 | 4.34 |
| Peak 16 | 21.15 | 4.20 |
| Peak 17 | 21.51 | 4.13 |
| Peak 18 | 22.11 | 4.02 |
| Peak 19 | 22.72 | 3.91 |
| Peak 20 | 24.03 | 3.70 |
| Peak 21 | 24.53 | 3.63 |
| Peak 22 | 24.91 | 3.57 |
| Peak 23 | 25.54 | 3.49 |
| Peak 24 | 26.54 | 3.36 |
| Peak 25 | 27.11 | 3.29 |
| Peak 26 | 27.61 | 3.23 |
| Peak 27 | 29.04 | 3.07 |
| Peak 28 | 30.49 | 2.93 |
| Peak 29 | 31.31 | 2.85 |
| Peak 30 | 33.00 | 2.71 |
| Peak 31 | 33.88 | 2.64 |
| Peak 32 | 35.52 | 2.53 |
| Peak 33 | 37.53 | 2.39 |
| Peak 34 | 40.46 | 2.23 |
| Peak 35 | 41.36 | 2.18 |
| Peak 36 | 42.40 | 2.13 |
| Peak 37 | 44.02 | 2.06 |

Example 7

Preparation of Single Crystal of Crystal Form D

Figure 16:
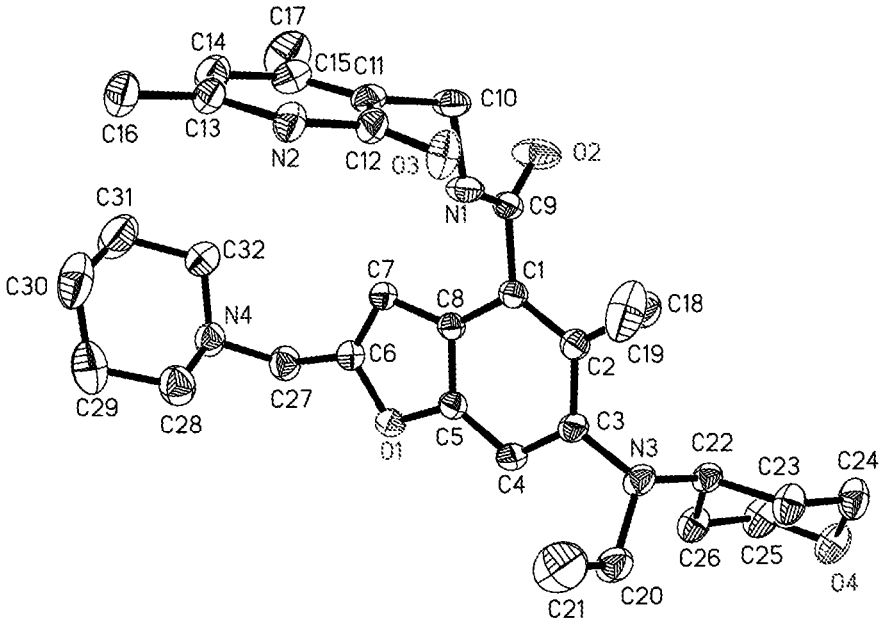
FIG. 16 shows the X-ray single crystal diffraction molecular stereostructure diagram of crystal form D of the compound of formula (I).

The crude product N-((4,6-dimethyl-2-oxo-1,2-dihydropyridin-3 -yl)methyl)-5-ethyl-6-(ethyl(tetrahydro-2 H-pyran-4-yl)amino)-2-(piperidin-1-ylmethyl)benzofuran-4-carboxamide (30mg, 0.055 mmol) obtained in Comparative example 1 was added to a reaction flask, and dissolved in a mixed solvent of methanol and pure water (v/v, 6:1, 1 mL). The mouth of the flask was sealed by a sealing film which was punctured two to three small holes. The solvent was volatilized to obtain a single crystal. The single molecular stereostructure of the crystal sample is shown in FIG. 16 by single crystal X-ray diffraction (XRD), and the unit cell parameters are shown in the following table:

TABLE 6

Unit cell parameters of single crystal of crystal form D

| Parameters | | Values |
|---|---|---|
| Crystal system | | Orthorhombic crystal system |
| Space group | | P bca |
| Unit cell parameters | a (Å) | 17.4737(6) |
| | b (Å) | 17.5933(5) |
| | c (Å) | 19.9907(7) |
| | α (°) | 90.0 |
| | β (°) | 90.0 |
| | γ (°) | 90.0 |

TABLE 6-continued

| Unit cell parameters of single crystal of crystal form D | |
|---|---|
| Parameters | Values |
| Unit cell volume V (Å$^3$) | 6145.5(3) |
| Z (Asymmetric unit number in unit cell) | 8 |
| Calculated density (g/cm$^3$) | 1.186 |

EXAMPLE 8

Preparation of Single Crystal of Crystal Form D)

The crude product N-((4,6-dimethyl-2-oxo-1,2-dihydropyridin-3-yl)methyl)-5-ethyl-6-(ethyl(tetrahydro-2 H-pyran-4-yl)amino)-2-(piperidin-1-ylmethyl)benzofuran-4-carboxamide (30 mg, 0.055 mmol) obtained in Comparative example 1 was added to a reaction flask, and dissolved in a mixed solvent of ethanol and pure water (v/v, 6:1, 1 mL). The mouth of the flask was sealed by a sealing film which was punctured two to three small holes. The solvent was volatilized to obtain a crystal which was identified as the single crystal of crystal form D by single crystal X-ray diffraction (XRD).

EXAMPLE 9

Preparation of Crystal Form D

The crude product N-((4,6-dimethyl-2-oxo-1,2-dihydropyridin-3-yl)methyl)-5-ethyl-6-(ethyl(tetrahydro-2 H-pyran-4-yl)amino)-2-(piperidin-1-ylmethyl)benzofuran-4-carboxamide (30 mg, 0.055 mmol) obtained in Comparative example 1 was added to a reaction flask, and ethyl acetate (300 μL) was added. The mixture was pulped at room temperature for two hours, filtrated and dried to obtain a pale yellow solid, which was identified as crystal form D by XRPD.

EXAMPLE 10

Preparation of Crystal Form D

The crude product N-((4,6-dimethyl-2-oxo-1,2-dihydropyridin-3-yl)methyl)-5-ethyl-6-(ethyl(tetrahydro-2 H-pyran-4-yl)amino)-2-(piperidin-1-ylmethyl)benzofuran-4-carboxamide (30 mg, 0.055 mmol) obtained in Comparative example 1 was added to a reaction flask, and propylene glycol methyl ether (300 μL) was added. The mixture was pulped at room temperature for two hours, filtrated and dried to obtain a pale yellow solid, which was identified as crystal form D by XRPD.

EXAMPLE 11

Preparation of Crystal Form D

The crude product N-((4,6-dimethyl-2-oxo-1,2-dihydropyridin-3 -yl)methyl)-5 -ethyl-6-(ethyl(tetrahy dro-2 H-pyran-4-yl)amino)-2-(piperidin-1-ylmethyl)benzofuran-4-carboxamide (30 mg, 0.055 mmol) obtained in Comparative example 1 was added to a reaction flask, and cyclohexane (300 μL) was added. The mixture was pulped at 25° C. for two hours, filtrated and dried to obtain a pale yellow solid, which was identified as crystal form D by XRPD.

EXAMPLE 12

Preparation of Crystal Form D

The crude product N-((4,6-dimethyl-2-oxo-1,2-dihydropyridin-3-yl)methyl)-5-ethyl-6-(ethyl(tetrahydro-2 H-pyran-4-yl)amino)-2-(piperidin-1-ylmethyl)benzofuran-4-carboxamide (30 mg, 0.055 mmol) obtained in Comparative example 1 was added to a reaction flask, and xylene (300 μL) was added. The mixture was pulped at 25° C. for two hours, filtrated and dried to obtain a pale yellow solid, which was identified as crystal form D by XRPD.

EXAMPLE 13

Preparation of Crystal Form D

The crude product N-((4,6-dimethyl-2-oxo-1,2-dihydropyridin-3 -yl)methyl)-5-ethyl-6-(ethyl(tetrahydro-2 H-pyran-4-yl)amino)-2-(piperidin-1-ylmethyl)benzofuran-4-carboxamide (30 mg, 0.055 mmol) obtained in Comparative example 1 was added to a reaction flask, and acetonitrile (300 μL) was added. The mixture was pulped at 50° C. for two hours, filtrated and dried to obtain a pale yellow solid, which was identified as crystal form D by XRPD.

EXAMPLE 14

Preparation of Crystal Form D)

The crude product N-((4,6-dimethyl-2-oxo-1,2-dihydropyridin-3-yl)methyl)-5-ethyl-6-(ethyl(tetrahydro-2 H-pyran-4-yl)amino)-2-(piperidin-1-ylmethyl)benzofuran-4-carboxamide (30 mg, 0.055 mmol) obtained in Comparative example 1 was added to a reaction flask, and acetone (300 μL) was added. The mixture was pulped at 50° C. for two hours, filtrated and dried to obtain a pale yellow solid, which was identified as crystal form D by XRPD.

EXAMPLE 15

Preparation of Crystal Form D

The crude product N-((4,6-dimethyl-2-oxo-1,2-dihydropyridin-3-yl)methyl)-5-ethyl-6-(ethyl(tetrahydro-2 H-pyran-4-yl)amino)-2-(piperidin-1-ylmethyl)benzofuran-4-carboxamide (30 mg, 0.055 mmol) obtained in Comparative example 1 was added to a reaction flask, and nitromethane (300 μL) was added. The mixture was pulped at 50° C. for two hours, filtrated and dried to obtain a pale yellow solid, which was identified as crystal form D by XRPD.

EXAMPLE 16

Preparation of crystal form D

The crude product N-((4,6-dimethyl-2-oxo-1,2-dihydropyridin-3-yl)methyl)-5-ethyl-6-(ethyl(tetrahydro-2 H-pyran-4-yl)amino)-2-(piperidin-1-ylmethyl)benzofuran-4-carboxamide (30 mg, 0.055 mmol) obtained in Comparative example 1 was added to a reaction flask, and dimethylformamide (300 μL) was added. The mixture was pulped for two hours, filtrated at 50° C. and dried to obtain a pale yellow solid, which was identified as crystal form D by XRPD.

EXAMPLE 17

Preparation of Crystal Form D

The crude product N-((4,6-dimethyl-2-oxo-1,2-dihydropyridin-3-yl)methyl)-5-ethyl-6-(ethyl(tetrahydro-2 H-pyran-4-yl)amino)-2-(piperidin-1-ylmethyl)benzofuran-4-carboxamide (30mg, 0.055 mmol) obtained in Comparative example 1 was added to a reaction flask, and dissolved in isopropanol (1 mL). The solvent was volatilized, and the resulting solid was then dried to obtain a pale yellow solid, which was identified as crystal form D by XRPD.

EXAMPLE 18

Preparation of Crystal Form D

The crude product N-((4,6-dimethyl-2-oxo-1,2-dihydropyridin-3-yl)methyl)-5-ethyl-6-(ethyl(tetrahydro-2 H-pyran-4-yl)amino)-2-(piperidin-1-ylmethyl)benzofuran-4-carboxamide (30 mg, 0.055 mmol) obtained in Comparative example 1 was added to a reaction flask, and dissolved in a mixed solvent of methanol and water (v/v, 19:1, 300 μL). The solvent was volatilized, and the resulting solid was then filtrated and dried to obtain a pale yellow solid, which was identified as crystal form D by XRPD.

EXAMPLE 19

Preparation of Crystal Form D

The crude product N-((4,6-dimethyl-2-oxo-1,2-dihydropyridin-3-yl)methyl)-5 -ethyl-6-(ethyl(tetrahydro-2 H-pyran-4-yl)amino)-2-(piperidin-1-ylmethyl)benzofuran-4-carboxamide (30 mg, 0.055 mmol) obtained in Comparative example 1 was added to a reaction flask, and dissolved in dioxane (1 mL). The solvent was volatilized, and the resulting solid was then dried to obtain a pale yellow solid, which was identified as crystal form D by XRPD.

EXAMPLE 20

Preparation of Crystal Form D

The crude product N-((4,6-dimethyl-2-oxo-1,2-dihy dropyridin-3-yl)methyl)-5-ethyl-6-(ethyl(tetrahydro-2 H-pyran-4-yl)amino)-2-(piperidin-1-ylmethyl)benzofuran-4-carboxamide (30 mg, 0.055 mmol) obtained in Comparative example 1 was added to a reaction flask, and dissolved in tetrahydrofuran (300 μL). The solution was added with water (900 μL) as an anti-solvent, and the resulting solid was then filtrated and dried to obtain a pale yellow solid, which was identified as crystal form D by XRPD.

EXAMPLE 21

Preparation of Crystal Form D

The crude product N-((4,6-dimethyl-2-oxo-1,2-dihydropyridin-3-yl)methyl)-5-ethyl-6-(ethyl(tetrahydro-2 H-pyran-4-yl)amino)-2-(piperidin-1-ylmethyl)benzofuran-4-carboxamide (30 mg, 0.055 mmol) obtained in Comparative example 1 was added to a reaction flask, and dimethyl sulfoxide (100 μL) was added. The mixture was pulped at 50° C., filtrated and dried to obtain a pale yellow solid, which was identified as crystal form D by XRPD.

EXAMPLE 22

Preparation of Crystal Form D

The crude product N-((4,6-dimethyl-2-oxo-1,2-dihydropyridin-3-yl)methyl)-5-ethyl-6-(ethyl(tetrahydro-2 H-pyran-4-yl)amino)-2-(piperidin-1-ylmethyl)benzofuran-4-carboxamide (30 mg, 0.055 mmol) obtained in Comparative example 1 was added to a reaction flask, and dichloromethane (100 μL) was added. The mixture was pulped at 25° C., filtrated and dried to obtain a pale yellow solid, which was identified as crystal form D by XRPD.

EXAMPLE 23

Preparation of Crystal Form D

The crude product N-((4,6-dimethyl-2-oxo-1,2-dihydropyridin-3-yl)methyl)-5-ethyl-6-(ethyl(tetrahydro-2 H-pyran-4-yl)amino)-2-(piperidin-1-ylmethyl)benzofuran-4-carboxamide (30 mg, 0.055 mmol) obtained in Comparative example 1 was added to a reaction flask, and methanol (100 μL) was added. The mixture was pulped at 50° C., filtrated and dried to obtain a pale yellow solid, which was identified as crystal form D by XRPD.

EXAMPLE 24.

Study of the Long-Term, Accelerated Stability of Crystal Forms B and D

The sample of crystal form B was spread flat in the air to test sample stability under conditions of 25° C.-65% relative humidity (RH), and the sampling time was Day 20. The sample of crystal form D was spread flat in the air to test sample stability under conditions of 40° C.-75% RH and 25° C.-65% RH, and the sampling time was Day 20.

Figure 10:
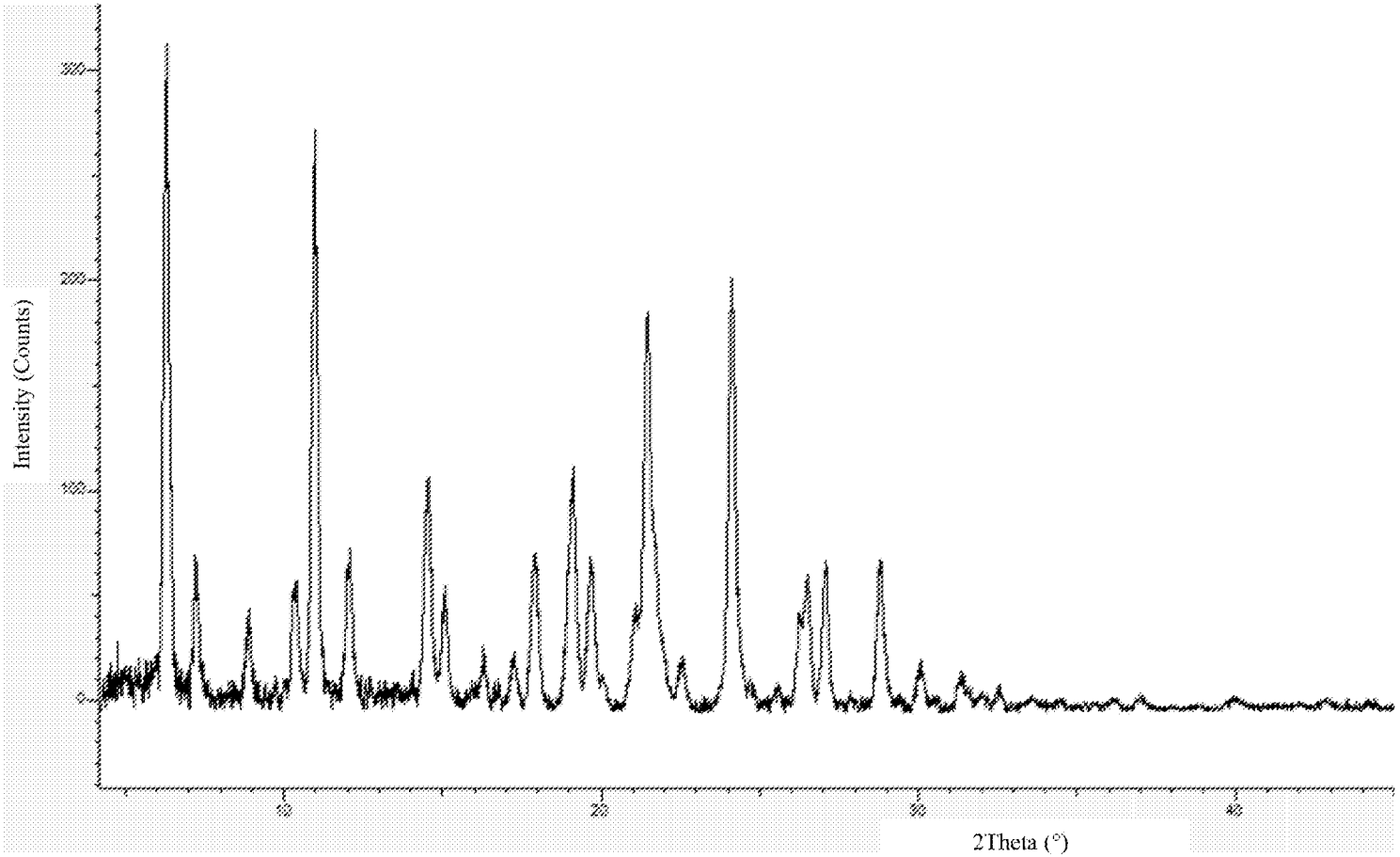
FIG. 10 shows the XRPD spectrum of crystal form B of the compound of formula (I) on Day 0.

Test results:

FIG. 10 shows the XRPD spectrum of crystal form B on Day 0.

Figure 11:
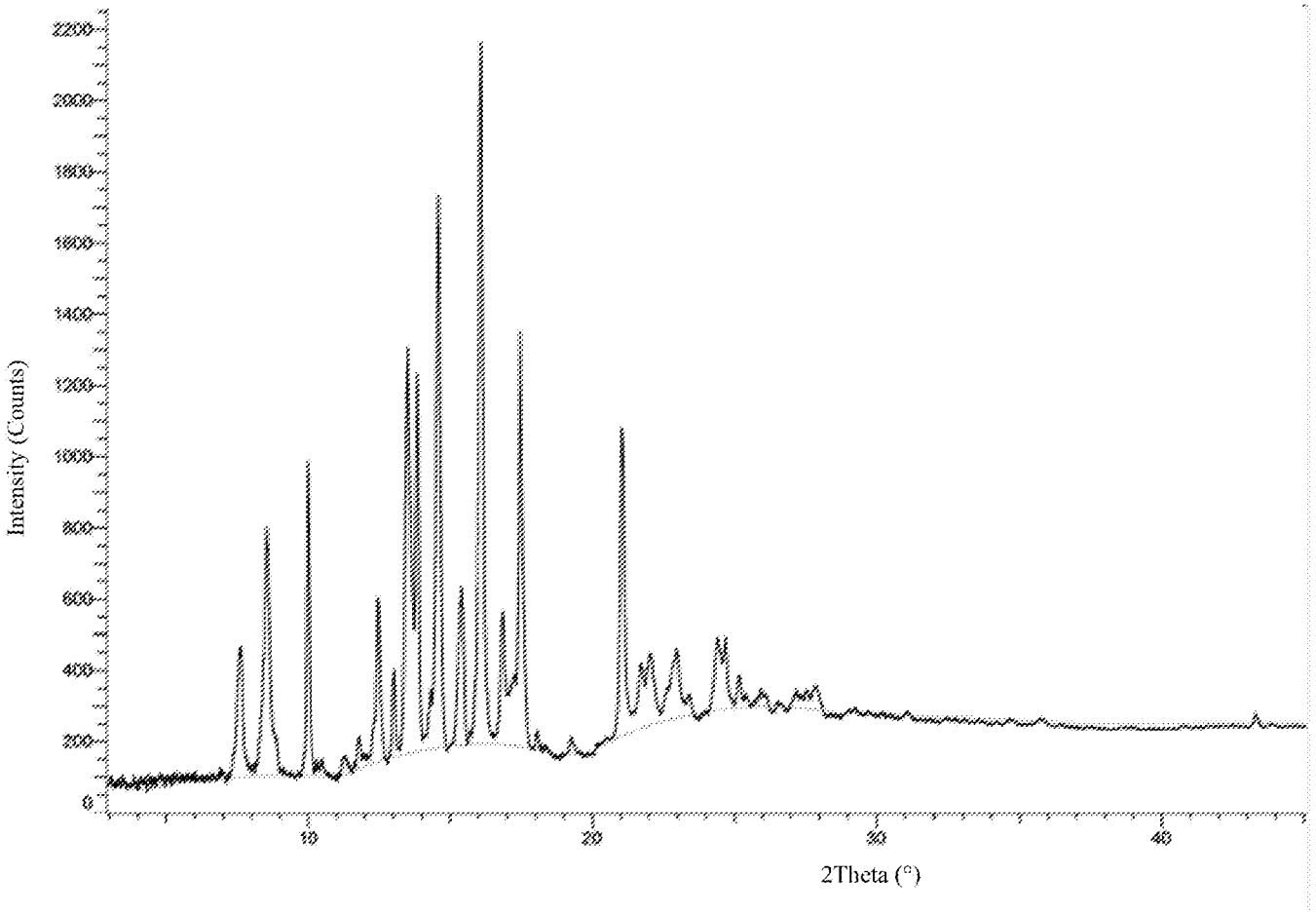
FIG. 11 shows the XRPD spectrum of crystal form B of the compound of formula (I) after 20 days under the conditions of 25° C., RH 65%.

FIG. 11 shows the XRPD spectrum of crystal form B after 20 days under the conditions of 25° C., RH 65% for 20 days.

Figure 12:
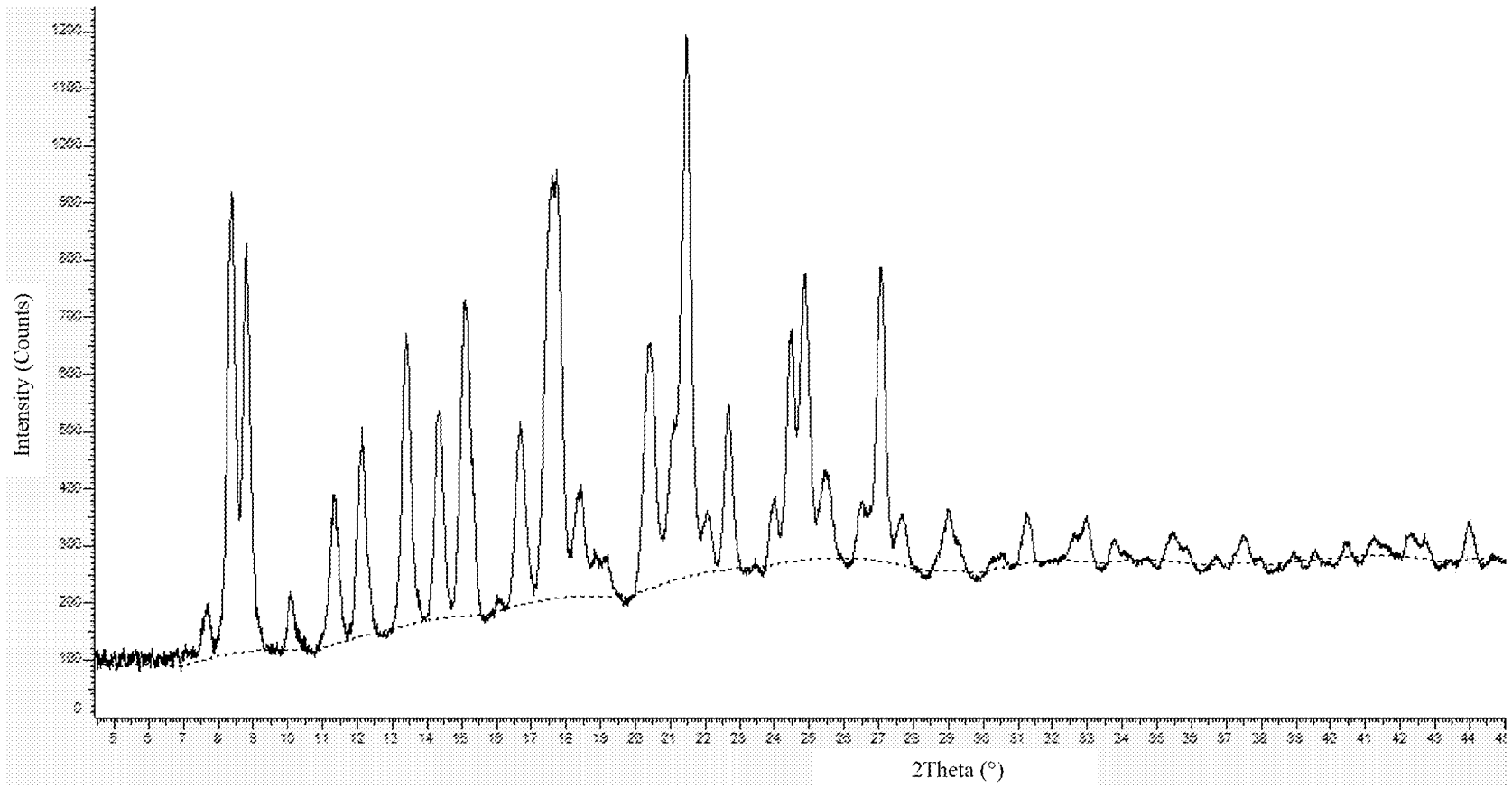
FIG. 12 shows the XRPD spectrum of crystal form D of the compound of formula (I) on Day 0.

FIG. 12 shows the XRPD spectrum of crystal form D on Day 0.

Figure 13:
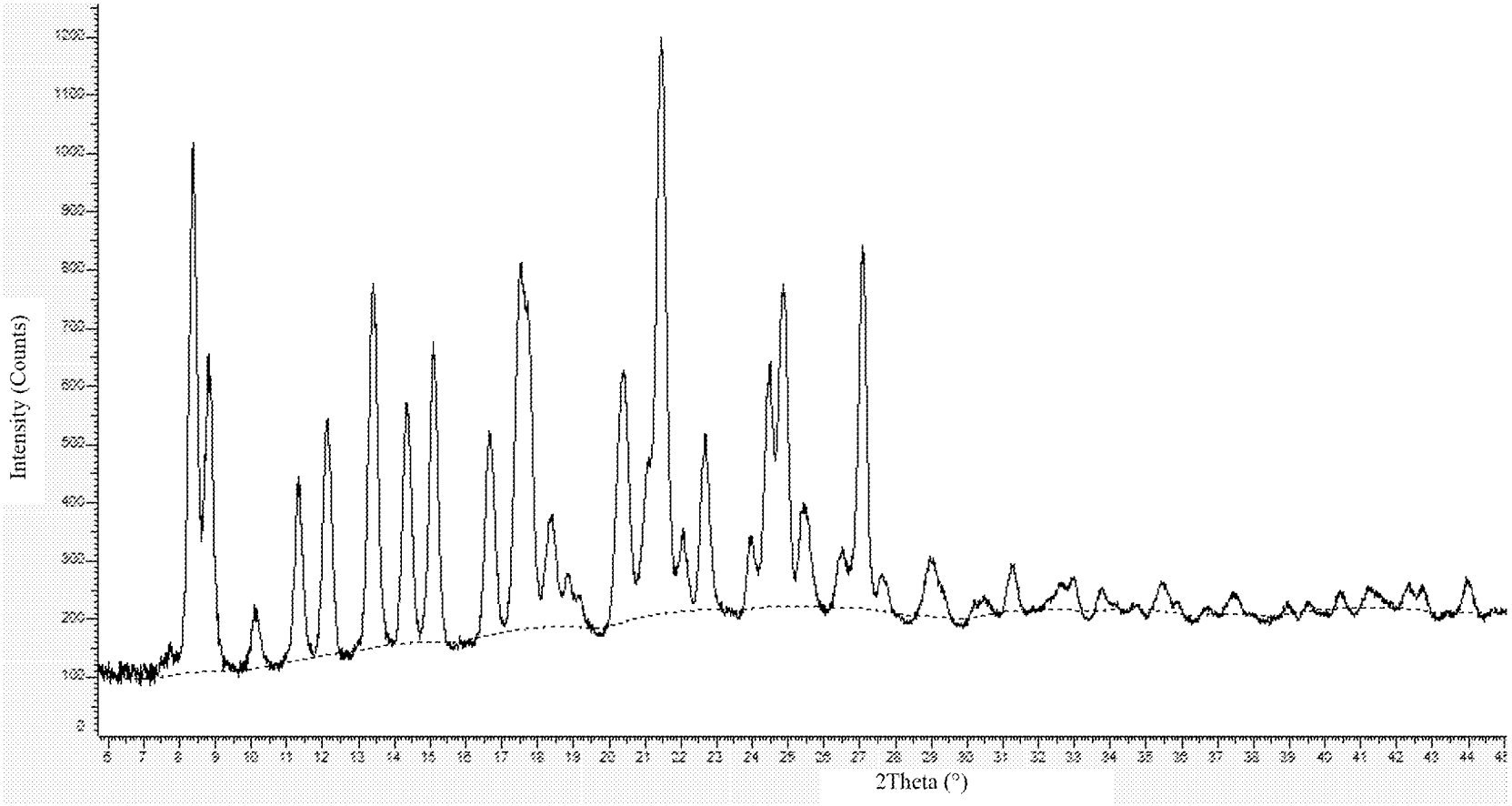
FIG. 13 shows the XRPD spectrum of crystal form D of the compound of formula (I) after 20 days under the conditions of 40° C., RH 75%.

FIG. 13 shows the XRPD spectrum of crystal form D after 20 days under the conditions of 40° C., RH 75% for 20 days.

Figure 14:
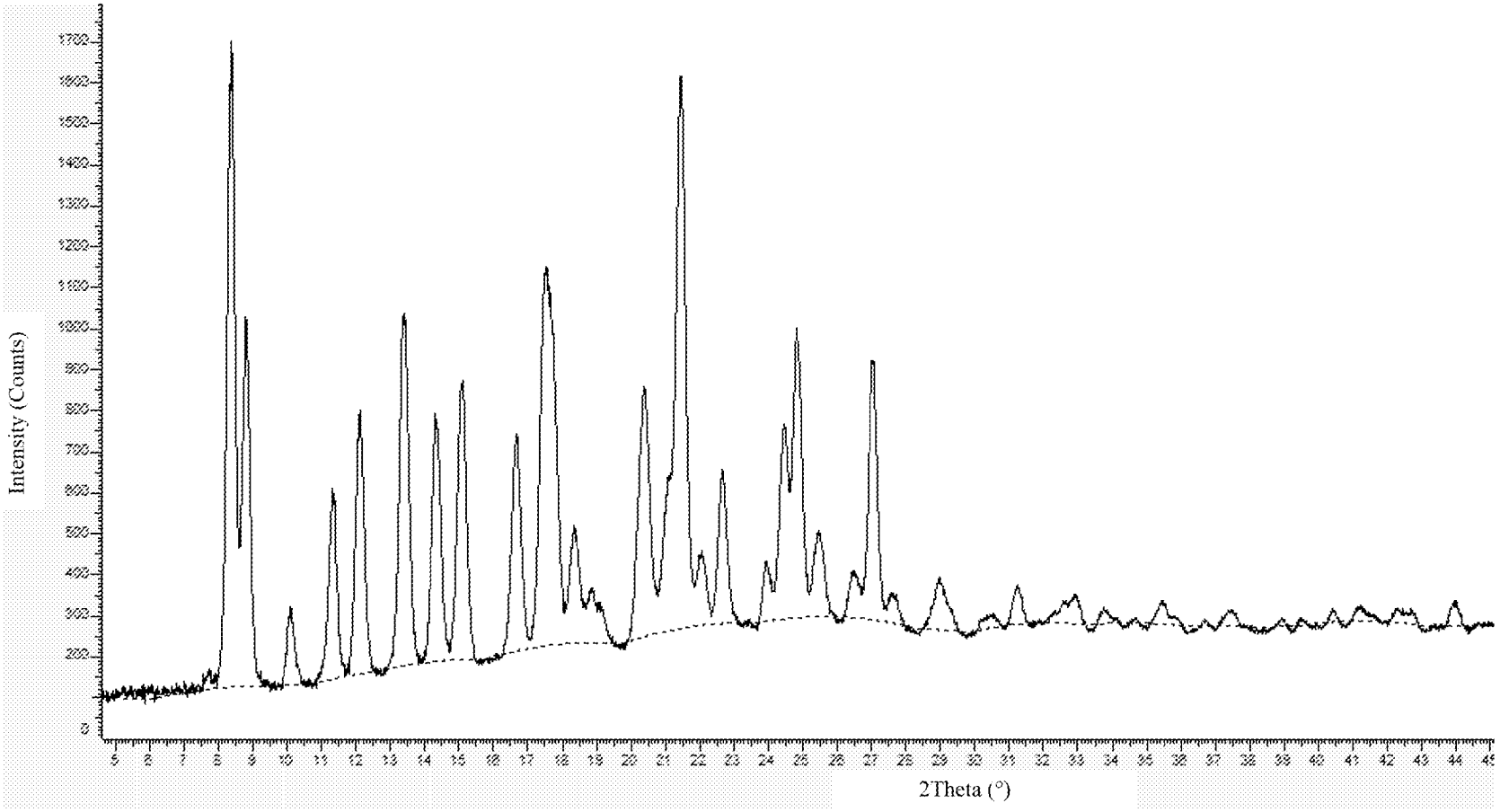
FIG. 14 shows the XRPD spectrum of crystal form D of the compound of formula (I) after 20 days under the conditions of 25° C., RH 65%.

FIG. 14 shows the XRPD spectrum of crystal form D after 20 days under the conditions of 25° C., RH 65% for 20 days.

Test conclusion:

The results of the stability study shown in FIGS. 12, 13 and 14 indicates that the XRPD peaks of the crystal form D of the compound of formula (I) has not changed substantially under the placement conditions of 40° C.-75% RH, and the crystal form is stable. The results shown in FIGS. 10 and 11 indicates that the XRPD peaks of the crystal form B of the compound of formula (I) has changed significantly under the placement conditions of 25° C.-65% RH. It can be seen that the physical stability of crystal form D is better than that of crystal form B under the placement conditions of 25° C.-65%RH.

What is claimed is:

1. A compound of formula (I):

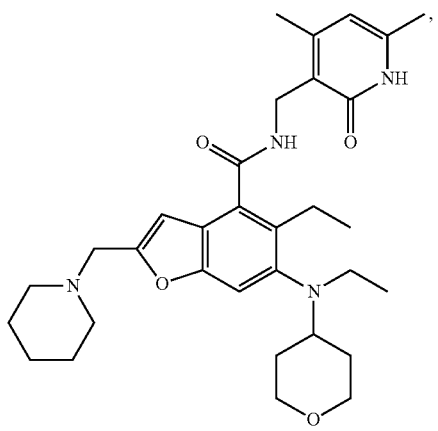

having a crystal form selected from the group consisting of crystal form A, crystal form B, crystal form C, and crystal form D, wherein:

the crystal form A has a powder X-ray diffraction spectrum comprising characteristic peaks at diffraction angles 2θ±0.2 of 7.60, 8.51, 11.80, 12.38, 13.52, 13.73, 14.48, 15.23, 15.99, 16.10, 16.82, 16.99, 17.35, 18.24, 20.82, 21.57, 21.91, 22.57, 22.76, 22.88, 24.29, 24.47, 25.24, 25.90, 27.23 and 27.74 using Cu-Kα radiation;

the crystal form B has a powder X-ray diffraction spectrum comprising characteristic peaks at diffraction angle 2θ±0.2 of 6.31, 7.24, 10.99, 12.07, 14.56, 17.94, 19.13, 19.71, 21.48, 24.15, 27.10 and 28.83 using Cu-Kα radiation;

the crystal form C has a powder X-ray diffraction spectrum comprising characteristic peaks at diffraction angles 2θ±0.2 of 7.40, 8.62, 9.49, 12.32, 13.39, 15.52, 19.15, 19.17, 21.42 and 22.78 using Cu-Kα radiation; and the crystal form D has a powder X-ray diffraction spectrum comprising characteristic peaks at diffraction angles 2θ±0.2 of 8.41, 8.85, 11.38, 12.18, 13.45, 15.15, 16.73, 17.59, 17.68, 20.45, 21.51, 22.72, 24.53, 24.91 and 27.11 using Cu-Kα radiation.

2. The compound according to claim 1, wherein the crystal form is crystal form A.

3. The compound according to claim 2, wherein the crystal form A has the powder X-ray diffraction spectrum comprising characteristic peaks at diffraction angles 2θ±0.2 of 7.60, 8.51, 10.37, 11.16, 11.80, 12.38, 12.89, 13.52, 13.73, 14.03, 14.48, 15.23, 15.99, 16.10, 16.43, 16.82, 16.99, 17.35, 18.24, 18.92, 19.17, 20.68, 20.82, 21.57, 21.91, 22.57, 22.76, 22.88, 23.53, 23.68, 24.00, 24.29, 24.47, 24.91, 25.24, 25.72, 25.90, 27.23, 27.74 and 35.63 using Cu-Kα radiation.

4. A method for preparing the compound according to claim 2, selected from the group consisting of:

method I, the method comprising dissolving the compound of formula (I) in a solvent, crystallizing the compound of formula (I) from the solvent using a crystallization method to obtain a crystal, filtering and drying the crystal to obtain the crystal form A, wherein the solvent is selected from the group consisting of an amide solvent, a mixed solvent of an amide solvent and water, and a mixed solvent of a halohydrocarbon and a nitrile, the amide solvent is selected from the group consisting of N,N-dimethylformamide and N,N-dimethylacetamide, the halohydrocarbon solvent is dichloromethane, and the nitrile solvent is acetonitrile, and the crystallization method is selected from the group consisting of room temperature crystallization, cooling crystallization, solvent volatilization crystallization and crystallization induced by addition of a seed crystal;

method II, the method comprising dissolving the compound of formula (I) in a first solvent to obtain a mixture, adding an anti-solvent to the mixture, crystallizing the compound of formula (I) from the first solvent and anti-solvent using a crystallization method to obtain a crystal, filtering and drying the crystal to obtain the crystal form A, wherein the first solvent is an alcohol solvent selected from the group consisting of methanol and isopropanol, the anti-solvent is water, and the crystallization method is selected from the group consisting of room temperature crystallization, cooling crystallization, solvent volatilization crystallization and crystallization induced by addition of a seed crystal; and method III, the method comprising adding the compound of formula (I) to a solvent to obtain a mixture, pulping the mixture to obtain a crystal, filtering and drying the crystal to obtain the crystal form A, wherein the solvent is selected from the group consisting of a mixed solvent of an amide solvent and water, and a mixed solvent of a halohydrocarbon and a nitrile, the amide solvent is selected from the group consisting of N,N-dimethylformamide and N,N-dimethylacetamide, the halohydrocarbon solvent is dichloromethane, and the nitrile solvent is acetonitrile.

5. The compound[crystal form] according to claim 1, wherein the crystal form is crystal form B.

6. The compound according to claim 5, wherein the crystal form B has the powder X-ray diffraction spectrum comprising characteristic peaks at diffraction angles 2θ±0.2 of 6.31, 7.24, 8.92, 10.38, 10.99, 12.07, 14.56, 15.10, 16.36, 17.29, 17.94, 19.13, 19.71, 21.12, 21.48, 22.59, 24.15, 25.45, 26.28, 26.52, 27.10, 28.83, 30.07, 31.37, 32.56, 33.65, 34.64, 36.09, 37.13 and 40.04 using Cu-Kα radiation.

7. A method for preparing the compound according to claim 5, selected from the group consisting of:

method I, the method comprising dissolving the compound of formula (I) in a solvent, crystallizing the compound of formula (I) from the solvent using a crystallization method to obtain a crystal, filtering and drying the crystal to obtain the crystal form B, wherein the solvent is ethanol, and the crystallization method is selected from the group consisting of room temperature crystallization, cooling crystallization, solvent volatilization crystallization and crystallization induced by addition of a seed crystal; and method II, the method comprising dissolving the compound of formula (I) in a first solvent to obtain a mixture, adding an anti-solvent to the mixture, crystallizing the compound of formula (I) from the first solvent and the anti-solvent using a crystallization method to obtain a crystal, filtering and drying the crystal to obtain the crystal form B, wherein the first solvent is ethanol, and the anti-solvent is water, the crystallization method is selected from the group consisting of room temperature crystallization, cooling crystallization, solvent volatilization crystallization and crystallization induced by addition of a seed crystal.

8. The compound according to claim 1, wherein the crystal form is crystal form C.

9. The compound according to claim 8, wherein the crystal form C has the powder X-ray diffraction spectrum comprising characteristic peaks at diffraction angles [2θ±0.2 of] 2θ±0.2 of 7.40, 8.62, 9.49, 9.96, 11.12, 12.32, 13.39, 14.21, 14.85, 15.52, 16.50, 17.67, 18.28, 19.15, 19.17, 20.06, 20.80, 21.42, 21.89, 22.20, 22.78, 23.41, 24.74, 25.34, 26.70, 27.38, 28.64, 29.63, 30.20 and 31.15 using Cu-Kα radiation.

10. A method for preparing the compound according to claim 8, the method comprising:

dissolving the compound of formula (I) in a first solvent to obtain a mixture, adding an anti-solvent to the mixture, crystallizing the compound of formula (I) from the first solvent and the anti-solvent using a crystallization method to obtain a crystal, filtering and drying the crystal to obtain the crystal form C, wherein the first solvent is an ether solvent, the ether solvent is 1,4-dioxane, the anti-solvent is selected from the group consisting of an aliphatic hydrocarbon solvent and an alicyclic hydrocarbon solvent, and the aliphatic hydrocarbon solvent is n-heptane, the alicyclic hydrocarbon solvent is cyclohexane, and the crystallization method is selected from the group consisting of room temperature crystallization, cooling crystallization, solvent volatilization crystallization and crystallization induced by addition of a seed crystal.

11. The compound according to claim 1, wherein the crystal form is crystal form D.

12. The compound according to claim 11, wherein the crystal form D has the powder X-ray diffraction spectrum comprising characteristic peaks at diffraction angles 2θ±0.2 of 8.41, 8.85, 10.15, 11.38, 12.18, 13.45, 14.40, 15.15, 16.73, 17.59, 17.68, 18.42, 18.91, 19.22, 20.45, 21.15, 21.51, 22.11, 22.72, 24.03, 24.53, 24.91, 25.54, 26.54, 27.11, 27.61, 29.04, 30.49, 31.31, 33.00, 33.88, 35.52, 37.53, 40.46, 41.36, 42.40 and 44.02 using Cu-Kα radiation.

13. A method for preparing the compound according to claim 11, selected from the group consisting of:

method I, the method comprising dissolving the compound of formula (I) in a solvent, crystallizing the compound of formula (I) from the solvent using a crystallization method to obtain a crystal, filtering and drying the crystal to obtain the crystal form D, wherein the solvent is selected from the group consisting of an alcohol solvent, an ether solvent, a mixed solvent of an alcohol and water, a mixed solvent of an ether and water, a mixed solvent of an alcohol and an aliphatic hydrocarbon, and a mixed solvent of an ether and an aliphatic hydrocarbon, the alcohol solvent is selected from the group consisting of methanol, ethanol and isopropanol, the ether solvent is selected from the group consisting of tetrahydrofuran and 1,4-dioxane, and the aliphatic hydrocarbon solvent is n-heptane, and the crystallization method is selected from the group consisting of room temperature crystallization, cooling crystallization, solvent volatilization crystallization and crystallization induced by addition of a seed crystal;

method II, the method comprising dissolving the compound of formula (I) in a first solvent to obtain a mixture, adding an anti-solvent to the mixture, crystallizing the compound of formula (I) from the first solvent and the anti-solvent using a crystallization method to obtain a crystal, filtering and drying the crystal to obtain the crystal form D, wherein the first solvent is selected from the group consisting of an alcohol solvent and an ether solvent, the alcohol solvent is selected from the group consisting of methanol and isopropanol, the ether solvent is tetrahydrofuran, and the anti-solvent is water; or the [good] *first* solvent is an ether solvent, the ether solvent is tetrahydrofuran, the anti-solvent is selected from the group consisting of an aliphatic hydrocarbon solvent and an alicyclic hydrocarbon solvent, the aliphatic hydrocarbon solvent is n-heptane, and the alicyclic hydrocarbon solvent is cyclohexane, and the crystallization method is selected from the group consisting of room temperature crystallization, cooling crystallization, solvent volatilization crystallization and crystallization induced by addition of a seed crystal; and method III, the method comprising adding the compound of formula (I) to a solvent to obtain a mixture, pulping the mixture to obtain a crystal, filtering and drying the crystal to obtain the crystal form D, wherein the solvent is selected from the group consisting of water, an ester, an ether, an aliphatic hydrocarbon, an alicyclic hydrocarbon, a nitroalkane solvent, an arene, an alcohol, a nitrile, a halohydrocarbon, a ketone, a sulfoxide, an amide, a mixed solvent of an alcohol and an ether, a mixed solvent of an alcohol and water, and a mixed solvent of one or more [alcohol] *alcohols*, the ester solvent is selected from the group consisting of ethyl acetate, isopropyl acetate and butyl acetate, the ether solvent is selected from the group consisting of tetrahydrofuran, 1,4-dioxane, propylene glycol methyl ether and methyl [tert- butyl] *tert-butyl* ether, the aliphatic hydrocarbon is n-heptane, the alicyclic hydrocarbon is cyclohexane, the nitroalkane solvent is nitromethane, the arene solvent is selected from the group consisting of xylene and cumene, the alcohol solvent is selected from the group consisting of methanol, ethanol and isopropanol, the nitrile solvent is acetonitrile, the halohydrocarbon solvent is dichloromethane, the ketone solvent is acetone, the sulfoxide is dimethyl sulfoxide, the amide solvent is selected from the group consisting of N,N-dimethylformamide and N,N-dimethylacetamide, the mixed solvent of one or more [alcohol] *alcohols* is selected from the group consisting of a mixed solvent of methanol and ethanol, a mixed solvent of methanol and isopropanol, and a mixed solvent of ethanol and isopropanol.

14. A pharmaceutical composition comprising the compound according to claim 1 and one or more pharmaceutically acceptable carriers, diluents or excipients.

15. A method for treating a disease associated with *one or more of an* EZH2 [inhibitor] *amplification or overexpression* in a subject in need thereof comprising administering to the subject an effective amount of the pharmaceutical composition according to claim 14.

16. The method according to claim 15, wherein the disease associated with [EZH2 inhibitor] *one or more of an EZH2 amplification or overexpression* is selected from the group consisting of lymphoma, leukemia, breast cancer, lung cancer, prostate cancer, ovarian cancer, liver cancer, melanoma, rhabdoid tumor, synovial sarcoma, mesothelioma, cervical cancer, colon cancer, rectal cancer, stomach cancer, pancreatic cancer, brain cancer, skin cancer, oral cancer, bone cancer, kidney cancer, bladder cancer, fallopian tube tumor, ovarian tumor, peritoneal tumor, glioma, glioblastoma, head and neck tumor and myeloma.

17. The method according to claim 16, wherein the leukemia is selected from the group consisting of chronic myeloid leukemia, acute myeloid leukemia and mixed lineage leukemia, and wherein the lymphoma is selected from the group consisting of non-Hodgkin lymphoma, diffuse large B-cell lymphoma and follicular lymphoma.

*18. The method according to claim 17, wherein the leukemia is chronic myeloid leukemia, acute myeloid leukemia, or mixed lineage leukemia.*

*19. The method according to claim 17, wherein the lymphoma is non-Hodgkin's lymphoma, diffuse large B-cell lymphoma, or follicular lymphoma.*

*20. The method according to claim 19, wherein the lymphoma is non Hodgkin's lymphoma.*

*21. The method according to claim 19, wherein the lymphoma is diffuse large B-cell lymphoma.*

*22. The method according to claim 19, wherein the lymphoma is follicular lymphoma.*

*23. The method according to claim 16, wherein the tumor or cancer is an ovarian tumor or an ovarian cancer.*

*24. A compound of formula (I):*

(I)

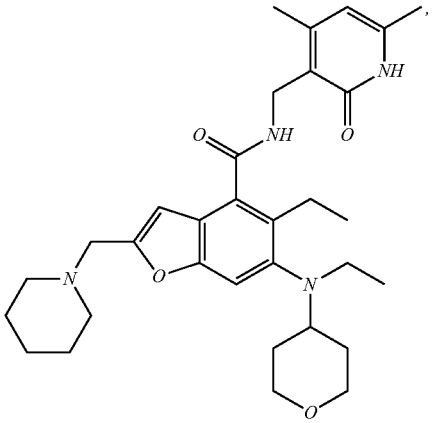

*having a crystal form A, wherein the crystal form A has a powder X-ray diffraction spectrum comprising characteristic peaks at diffraction angles 2θ±0.2 of 7.60, 8.51, 15.23, 15.99, and 16.82 using Cu-Kα radiation.*

*25. The compound according to claim 24, wherein the crystal form A has the powder X-ray diffraction spectrum comprising characteristic peaks at different angles 2θ±0.2 of 7.60, 8.51, 13.52, 14.48, 15.23, 15.99, 16.82, and 21.91 using Cu-Kα radiation.*

*26. The compound according to claim 25, wherein the crystal form A has a powder X-ray diffraction spectrum comprising characteristic peaks at diffraction angles 2θ±0.2 of 7.60, 8.51, 11.80, 12.38, 13.52, 14.48, 15.23, 15.99, 16.10, 16.82, 21.91, 22.57, 24.29, and 24.47 using Cu-Kα radiation.*

*27. The compound according to claim 26, wherein the crystal form A has the powder X-ray diffraction spectrum comprising characteristic peaks at diffraction angles 2θ±0.2 of 7.60, 8.51, 11.80, 12.38, 13.52, 13.73, 14.48, 15.23, 15.99, 16.10, 16.82, 16.99, 17.35, 18.24, 20.82, 21.57, 21.91, 22.57, 22.76, 22.88, 24.29, 24.47, 25.24, 25.90, 27.23, and 27.74 using Cu-Kα radiation.*

*28. A pharmaceutical composition comprising the compound according to claim 24 and one or more pharmaceutically acceptable carriers, diluents or excipients.*

*29. A method for inhibiting EZH2 in a subject in need thereof, comprising administering to the subject a pharmaceutical composition according to claim 28.*

*30. A method for treating a disease associated with one or more of an EZH2 amplification or overexpression in a subject in need thereof comprising administering to the subject an effective amount of the pharmaceutical composition according to claim 28.*

*31. The method according to claim 30, wherein the disease associated with one or more of an EZH2 amplification or overexpression is selected from the group consisting of lymphoma, leukemia, breast cancer, lung cancer, prostate cancer, ovarian cancer, liver cancer, melanoma, rhabdoid tumor, synovial sarcoma, mesothelioma, cervical cancer, colon cancer, rectal cancer, stomach cancer, pancreatic cancer, brain cancer, skin cancer, oral cancer, bone cancer, kidney cancer, bladder cancer, fallopian tube tumor, ovarian tumor, peritoneal tumor, glioma, glioblastoma, head and neck tumor and myeloma.*

*32. The method according to claim 31, wherein the leukemia is selected from the group consisting of chronic myeloid leukemia, acute myeloid leukemia and mixed lineage leukemia.*

*33. The method according to claim 31, wherein the lymphoma is non-Hodgkin's lymphoma, diffuse large B-cell lymphoma, or follicular lymphoma.*

*34. The method according to claim 33, wherein the lymphoma is non-Hodgkin's lymphoma.*

*35. The method according to claim 33, wherein the lymphoma is diffuse large B-cell lymphoma.*

*36. The method according to claim 33, wherein the lymphoma is follicular lymphoma.*

*37. The method according to claim 31, wherein the disease is an ovarian tumor or an ovarian cancer.*

*38. A compound of formula (I):*

(I)

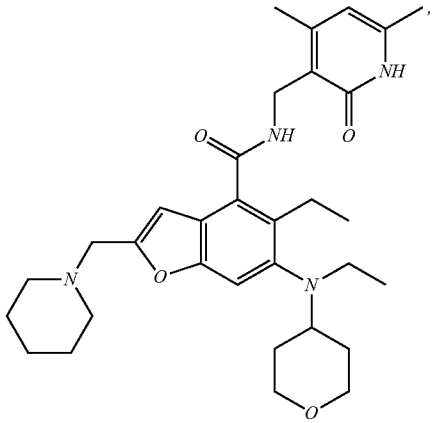

*having a crystal form A, wherein the crystal form A has a powder X-ray diffraction spectrum comprising characteristic peaks at different angles 2θ±0.2 of 7.60, 8.51, 15.23, 15.99, and 16.82 using Cu-Kα radiation, prepared by a process selected from the group consisting of:*

*method I, the method comprising dissolving the compound of formula (I) in a solvent, crystallizing the compound of formula (I) from the solvent using a crystallization method to obtain a crystal, filtering and drying the crystal to obtain the crystal form A, wherein the solvent is selected from the group consisting of an amide solvent, a mixed solvent of an amide solvent and water, and a mixed solvent of halohydrocarbon and a nitrile, the amide solvent is selected from the group*

*consisting of N,N-dimethylformamide and N,N-dimethylacetamide, the halohydrocarbon solvent is dichloromethane, and the nitrile solvent is acetonitrile, and the crystallization method is selected from the group consisting of room temperature crystallization, cooling crystallization, solvent volatilization crystallization and crystallization induced by addition of a seed crystal;*

*method II, the method comprising dissolving the compound of formula (I) in a first solvent to obtain a mixture, adding an anti-solvent to the mixture, crystallizing the compound of formula (I) from the first solvent and anti-solvent using a crystallization method to obtain a crystal, filtering and drying the crystal to obtain the crystal form A, wherein the first solvent is an alcohol solvent selected from the group consisting of methanol and isopropanol, the anti-solvent is water, and the crystallization method is selected from the group consisting of room temperature crystallization, cooling crystallization, solvent volatilization crystallization and crystallization induced by addition of a seed crystal; and*

*method III, the method comprising adding the compound of formula (I) to a solvent to obtain a mixture, pulping the mixture to obtain a crystal, filtering and drying the crystal to obtain the crystal form A, wherein the solvent is selected from the group consisting of a mixed solvent of an amide solvent and water, and a mixed solvent of a halohydrocarbon and a nitrile, the amide solvent is selected from the group consisting of N,N-dimethylformamide and N,N-dimethylacetamide, the halohydrocarbon solvent is dichloromethane, and the nitril solvent is acetonitrile.*

*39. A compound of formula (I):*

(I)

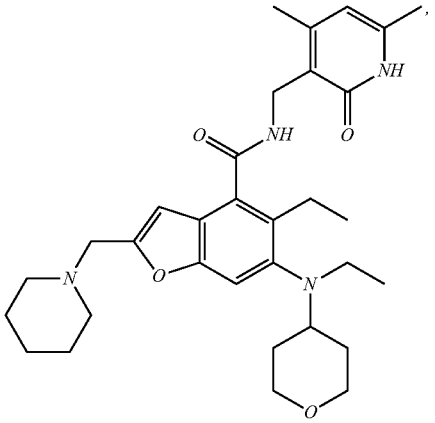

*having a crystal form B, wherein the crystal form B has a powder X-ray diffraction spectrum comprising characteristic peaks at diffraction angles 2θ±0.2 of 6.31, 10.99, 19.13, 21.48, and 24.15 using Cu-Kα radiation.*

*40. The compound according to claim 39, wherein the crystal form B has the powder X-ray diffraction spectrum comprising characteristic peaks at diffraction angles 2θ±0.2 of 6.31, 10.99, 12.07, 14.56, 17.94, 19.13, 21.48, and 24.15 using Cu-Kα radiation.*

*41. The compound according to claim 40, wherein the crystal form B has a powder X-ray diffraction spectrum comprising characteristic peaks at diffraction angles 2θ±0.2 of 6.31, 7.24, 10.99, 12.07, 14.56, 17.94, 19.13, 19.71, 21.48, 24.15, 27.10, and 28.83 using Cu-Kα radiation.*

*42. The compound according to claim 41, wherein the crystal form B has the powder X-ray diffraction spectrum comprising characteristic peaks at diffraction angles 2θ±0.2 of 6.31, 7.24, 8.92, 10.38, 10.99, 12.07, 14.56, 15.10, 17.94, 19.13, 19.71, 21.48, 24.15, 26.52, 27.10, and 28.83 using Cu-Kα radiation.*

*43. A pharmaceutical composition comprising the compound according to claim 39 and one or more pharmaceutically acceptable carriers, diluents or excipients.*

*44. A method for inhibiting EXH2 in a subject in need thereof, comprising administering to the subject a pharmaceutical composition according to claim 43.*

*45. A method for treating a disease associated with one or more of an EZH2 amplification or overexpression in a subject in need thereof comprising administering to the subject an effective amount of the pharmaceutical composition according to claim 43.*

*46. The method according to claim 45, wherein the disease associated with one or more of an EZH2 amplification or overexpression is selected from the group consisting of lymphoma, leukemia, breast cancer, lung cancer, prostate cancer, ovarian cancer, liver cancer, melanoma, rhabdoid tumor, synovial sarcoma, mesothelioma, cervical cancer, colon cancer, rectal cancer, stomach cancer, pancreatic cancer, brain cancer, skin cancer, oral cancer, bone cancer, kidney cancer, bladder cancer, fallopian tube tumor, ovarian tumor, peritoneal tumor, glioma, glioblastoma, head and neck tumor and myeloma.*

*47. The method according to claim 46, wherein the leukemia is selected from the group consisting of chronic myeloid leukemia, acute myeloid leukemia and mixed lineage leukemia.*

*48. The method according to claim 46, wherein the lymphoma is non-Hodgkin's lymphoma, diffuse large B-cell lymphoma, or follicular lymphoma.*

*49. The method according to claim 48, wherein the lymphoma is non-Hodgkin's lymphoma.*

*50. The method according to claim 48, wherein the lymphoma is diffuse large B-cell lymphoma.*

*51. The method according to claim 48, wherein the lymphoma is follicular lymphoma.*

*52. The method according to claim 46, wherein the disease is an ovarian tumor or an ovarian cancer.*

*53. A compound of formula (I):*

(I)

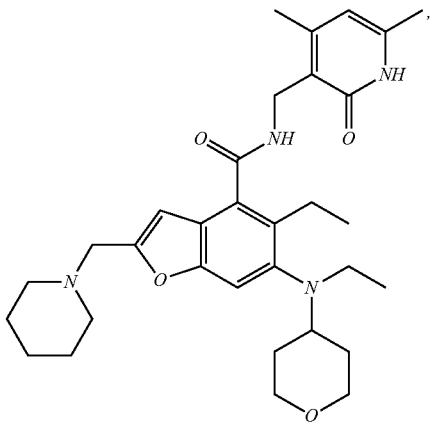

*having a crystal form B, wherein the crystal form B has a powder X-ray diffraction spectrum comprising characteristic peaks at diffraction angles 2θ±0.2 of 6.31, 10.99, 19.13, 21.48, and 24.15 using Cu-Kα radiation, prepared by a process selected from the group consisting of:*

*method I, the method comprising dissolving the compound of formula (I) in a solvent, crystallizing the compound of formula (I) from the solvent using a crystallization method to obtain a crystal, filtering and drying the crystal to obtain the crystal form B, wherein the solvent is ethanol, and the crystallization method is selected from the group consisting of room temperature crystallization, cooling crystallization, solvent volatilization crystallization and crystallization induced by addition of a seed crystal; and*

*method II, the method comprising dissolving the compound of formula (I) in a first solvent to obtain a mixture, adding an anti-solvent to the mixture, crystallizing the compound of formula (I) from the first solvent and the anti-solvent using a crystallization method to obtain a crystal, filtering and drying the crystal to obtain the crystal form B, wherein the first solvent is ethanol, and the anti-solvent is water, the crystallization method is selected from the group consisting of room temperature crystallization, cooling crystallization, solvent volatilization crystallization and crystallization induced by addition of a seed crystal.*

*54. A compound of formula (I):*

(I)

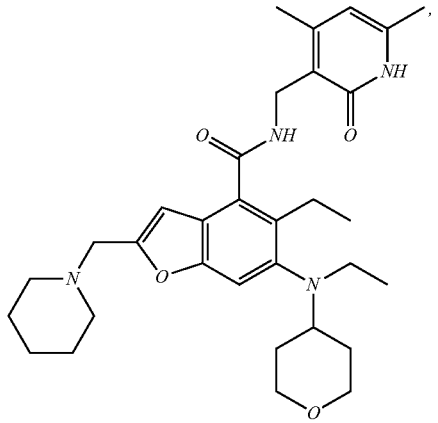

*having a crystal form C, wherein the crystal form C has a powder X-ray diffraction spectrum comprising characteristic peaks a diffraction angles 2θ±0.2 of 7.40, 9.49, 12.32, 13.39, and 15.52 using Cu-Kα radiation.*

*55. The compound according to claim 54, wherein the crystal form C has the powder X-ray diffraction spectrum comprising characteristic peaks at diffraction angles 2θ±0.2 of 7.40, 8.62, 9.49, 12.32, 13.39, 15.52, 22.78 using Cu-Kα radiation.*

*56. The compound according to claim 55, wherein the crystal form C has a powder X-ray diffraction spectrum comprising characteristic peaks at diffraction angles 2θ±0.2 of 7.40, 8.62, 9.49, 12.32, 13.39, 15.52, 19.15, 19.17, 21.42, and 22.78 using Cu-Kα radiation.*

*57. The compound according to claim 56, wherein the crystal form C has the powder X-ray diffraction spectrum comprising characteristic peaks at diffraction angles 2θ±0.2 of 7.40, 8.62, 9.49, 9.96, 12.32, 13.39, 14.21, 15.52, 17.67, 18.28, 19.15, 19.17, 21.42, 22.78, 24.74, and 25.34 using Cu-Kα radiation.*

*58. A pharmaceutical composition comprising the compound according to claim 54 and one or more pharmaceutically acceptable carriers, diluents or excipients.*

*59. A method for inhibiting EZH2 in a subject in need thereof, comprising administering to the subject a pharmaceutical composition according to claim 58.*

*60. A method for treating a disease associated with one or more of an EZH2 amplification or overexpression in a subject in need thereof comprising administering to the subject an effective amount of the pharmaceutical composition according to claim 58.*

*61. The method according to claim 60, wherein the disease associated with one or more of an EZH2 amplification or overexpression is selected from the group consisting of lymphoma, leukemia, breast cancer, lung cancer, prostate cancer, ovarian cancer, liver cancer, melanoma, rhabdoid tumor, synovial sarcoma, mesothelioma, cervical cancer, colon cancer, rectal cancer, stomach cancer, pancreatic cancer, brain cancer, skin cancer, oral cancer, bone cancer, kidney cancer, bladder cancer, fallopian tube tumor, ovarian tumor, peritoneal tumor, glioma, glioblastoma, head and neck tumor and myeloma.*

*62. The method according to claim 61, wherein the leukemia is selected from the group consisting of chronic myeloid leukemia, acute myeloid leukemia and mixed lineage leukemia.*

*63. The method according to claim 61, wherein the lymphoma is non-Hodgkin's lymphoma, diffuse large B-cell lymphoma, or follicular lymphoma.*

*64. The method according to claim 63, wherein the lymphoma is non-Hodgkin's lymphoma.*

*65. The method according to claim 63, wherein the lymphoma is diffuse large B-cell lymphoma.*

*66. The method according to claim 63, wherein the lymphoma is follicular lymphoma.*

*67. The method according to claim 61, wherein the disease is an ovarian tumor or an ovarian cancer.*

*68. A compound of formula (I):*

(I)

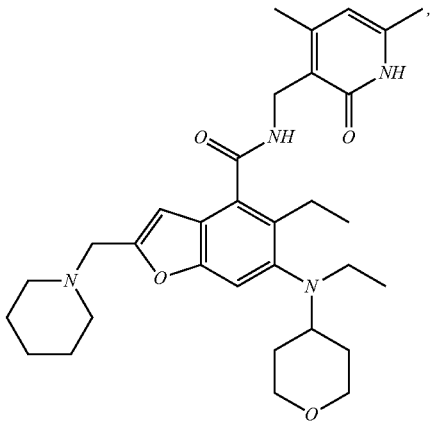

*having a crystal form C, wherein the crystal form C has a powder X-ray diffraction spectrum comprising characteristic peaks at diffraction angles 2θ±0.2 of 7.40, 9.49, 12.32, 13.39, and 15.52 using Cu-Kα radiation, prepared by a process comprising dissolving the compound of formula (I)*

*in a first solvent to obtain a mixture, adding and anti-solvent to the mixture, crystallizing the compound of formula (I) from the first solvent and the anti-solvent using a crystallization method to obtain a crystal, filtering and drying the crystal to obtain the crystal form C, wherein the first solvent is an ether solvent, the ether solvent is 1,4-dioxane, the anti-solvent is selected from the group consisting of an aliphatic hydrocarbon solvent and an alicyclic hydrocarbon solvent, and the aliphatic hydrocarbon solvent is n-heptane, the alicyclic hydrocarbon solvent is cyclohexane, and the crystallization method is selected from the group consisting of room temperature crystallization, cooling crystallization, solvent volatilization crystallization and crystallization induced by addition of a seed crystal.*

*69. A compound of formula (I):*

(I)

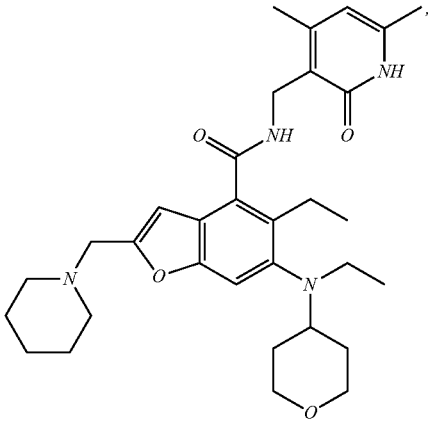

*having a crystal form D, wherein the crystal form D has a powder X-ray diffraction spectrum comprising characteristic peaks at diffraction angles 2θ±0.2 of 8.41, 13.45, 17.59, 21.51, and 24.91 using Cu-Kα radiation.*

*70. The compound according to claim 69, wherein the crystal form D has the powder X-ray diffraction spectrum comprising characteristic peaks at diffraction angles 2θ±0.2 of 8.41, 8.85, 13.45, 15.15, 17.59, 17.68, 21.51, 24.91, and 27.11 using Cu-Kα radiation.*

*71. The compound according to claim 70, wherein the crystal form D has a powder X-ray diffraction spectrum comprising characteristic peaks at diffraction angles 2θ±0.2 of 8.41, 8.85, 11.38, 12.18, 13.45, 15.15, 16.73, 17.59, 17.68, 20.45, 21.51, 22.72, 24.53, 24.91 and 27.11 using Cu-Kα radiation.*

*72. The compound according to claim 71, wherein the crystal form D has the powder X-ray diffraction spectrum comprising characteristic peaks at diffraction angles 2θ±0.2 of 8.41, 8.85, 11.38, 12.18, 13.45, 14.40, 15.15, 16.73, 17.59, 17.68, 18.42, 20.45, 21.15, 21.51, 22.11, 22.72, 24.03, 24.53, 24.91, 25.54, 26.54, 27.11, 27.61, and 29.04 using Cu-Kα radiation.*

*73. A pharmaceutical composition comprising the compound according to claim 69 and one or more pharmaceutically acceptable carriers, diluents or excipients.*

*74. A method for inhibiting EZH2 in a subject in need thereof, comprising administering to the subject a pharmaceutical composition according to claim 73.*

*75. A method for treating a disease associated with one or more of an EZH2 amplification or overexpression in a subject in need thereof comprising administering to the subject an effective amount of the pharmaceutical composition according to claim 73.*

*76. The method according to claim 75, wherein the disease associated with one or more of an EZH2 amplification or overexpression is selected from the group consisting of lymphoma, leukemia, breast cancer, lung cancer, prostate cancer, ovarian cancer, liver cancer, melanoma, rhabdoid tumor, synovial sarcoma, mesothelioma, cervical cancer, colon cancer, rectal cancer, stomach cancer, pancreatic cancer, brain cancer, skin cancer, oral cancer, bone cancer, kidney cancer, bladder cancer, fallopian tube tumor, ovarian tumor, peritoneal tumor, glioma, glioblastoma, head and neck tumor and myeloma.*

*77. The method according to claim 76, wherein the leukemia is selected from the group consisting of chronic myeloid leukemia, acute myeloid leukemia and mixed lineage leukemia.*

*78. The method according to claim 76, wherein the lymphoma is non-Hodgkin's lymphoma, diffuse large B-call lymphoma, or follicular lymphoma.*

*79. The method according to claim 78, wherein the lymphoma is non-Hodgkin's lymphoma.*

*80. The method according to claim 78, wherein the lymphoma is diffuse large B-cell lymphoma.*

*81. The method according to claim 78, wherein the lymphoma is follicular lymphoma.*

*82. The method according to claim 76, wherein the disease is an ovarian tumor or an ovarian cancer.*

*83. A compound of formula (I):*

(I)

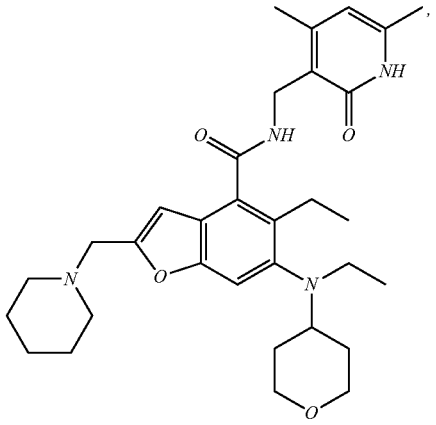

*having a crystal form D, wherein the crystal form D has a powder X-ray diffraction spectrum comprising characteristic peaks at diffraction angles 2θ±0.2 of 8.41, 13.45, 17.59, 21.51, and 24.91 using Cu-Kα radiation, prepared by a process selected from the group consisting of:*

*method I, the method comprising dissolving the compound of formula (I) in a solvent, crystallizing the compound of formula (I) from the solvent using a crystallization method to obtain a crystal, filtering and drying the crystal to obtain the crystal form D, wherein the solvent is selected from the group consisting of an alcohol solvent, an ether solvent, a mixed solvent of an alcohol and water, a mixed solvent of an ether and water, a mixed solvent of an alcohol and an aliphatic hydrocarbon, and a mixed solvent of an ether and an aliphatic hydrocarbon, the alcohol solvent is selected*

*from the group consisting of methanol, ethanol and isopropanol, the ether solvent is selected from the group consisting of tetrahydrofuran and 1,4-dioxane, and the aliphatic hydrocarbon solvent is n-heptane, and the crystallization method is selected from the group consisting of room temperature crystallization, cooling crystallization, solvent volatilization crystallization and crystallization induced by addition of a seed crystal;*

*method II, the method comprising dissolving the compound of formula (I) in a first solvent to obtain a mixture, adding an anti-solvent to the mixture, crystallizing the compound of formula (I) from the first solvent and the anti-solvent using a crystallization method to obtain a crystal, filtering and drying the crystal to obtain the crystal form D, wherein the first solvent is selected from the group consisting of an alcohol solvent and an ether solvent, the alcohol solvent is selected from the group consisting of methanol and isopropanol, the ether solvent is tetrahydrofuran, and the anti-solvent is water; or the first solvent is an ether solvent, the ether solvent is tetrahydrofuran, the anti-solvent is selected from the group consisting of an aliphatic hydrocarbon solvent and an alicyclic hydrocarbon solvent, the aliphatic hydrocarbon solvent is n-heptane, and the alicyclic hydrocarbon solvent is cyclohexane, and the crystallization method is selected from the group consisting of room temperature crystallization, cooling crystallization, solvent volatilization crystallization and crystallization induced by addition of a seed crystal; and*

*method III, the method comprising adding the compound of formula (I) to a solvent to obtain a mixture, pulping the mixture to obtain crystal, filtering and drying the crystal to obtain the crystal form D, wherein the solvent is selected from the group consisting of water, an ester, an ether, an aliphatic hydrocarbon, an alicyclic hydrocarbon, a nitroalkane solvent, an arene, an alcohol, a nitrile, a halohydrocarbon, a ketone, a sulfoxide, an amide, a mixed solvent of an alcohol and an ether, a mixed solvent of an alcohol and water, and a mixed solvent of one or more alcohols, the ester solvent is selected from the group consisting of ethyl acetate, isopropyl acetate and butyl acetate, the ether solvent is selected from the group consisting of tetrahydrofuran, 1,4-dioxane, propylene glycol methyl ether and methyl tert- butyl ether, the aliphatic hydrocarbon is n-heptane, the alicyclic hydrocarbon is cyclohexane, the nitroalkane solvent if nitromethane, the arene solvent is selected from the group consisting of xylene and cumene, the alcohol solvent is selected from the group consisting of methanol, ethanol and isopropanol, the nitril solvent is acetonitrile, the halohydrocarbon solvent is dichloromethane, the ketone solvent is acetone, the sulfoxide is dimethyl sulfoxide, the amide solvent is selected from the group consisting of N,N-dimethylformamide and N,N-dimethylacetamide, the mixed solvent of one or more alcohols is selected from the group consisting of a mixed solvent of methanol and ethanol, a mixed solvent of methanol and isopropanol, and a mixed solvent of ethanol and isopropanol.*

*84. A method for treating a tumor or cancer in a subject in need thereof, wherein the treating is associated with an EZH2 inhibitor and the tumor or cancer is selected from the group consisting of lymphoma, leukemia, breast cancer, lung cancer, prostate cancer, ovarian cancer, liver cancer, melanoma, rhabdoid tumor, synovial sarcoma, mesothelioma, cervical cancer, colon cancer, rectal cancer, stomach cancer, pancreatic cancer, brain cancer, skin cancer, oral cancer, bone cancer, kidney cancer, bladder cancer, fallopian tube tumor, ovarian tumor, peritoneal tumor, glioma, glioblastoma, head and neck tumor and myeloma, wherein the method comprises administering a therapeutically effective amount of a compound of formula (I):*

*(I)*

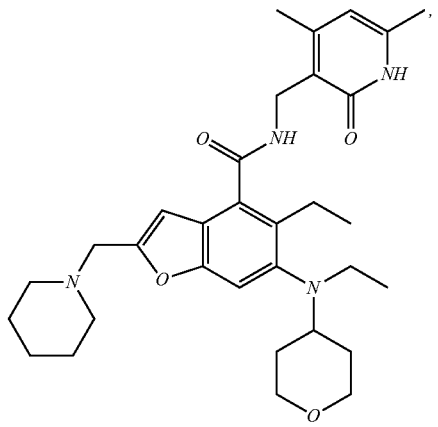

*having a crystal form selected from the group consisting of crystal form A, crystal form B, crystal form C, and crystal form D, wherein:*

*the crystal form A has a powder X-ray diffraction spectrum comprising characteristic peaks at diffraction angles 2θ±0.2 of 7.60, 8.51, 15.23, 15.99, and 16.82 using Cu-Kα radiation;*

*the crystal form B has a powder X-ray diffraction spectrum comprising characteristic peaks at diffraction angles 2θ±0.2 of 6.31, 10.99, 12.07, 14.56, 17.94, 19.13, 21.48, and 24.15 using Cu-Kα radiation;*

*the crystal form C has a powder X-ray diffraction spectrum comprising characteristic peaks at diffraction angles 2θ±0.2 of 7.40, 9.49, 12.32, 13.39, and 15.52 using Cu-Kα radiation; and*

*the crystal form D has a powder X-ray diffraction spectrum comprising characteristic peaks at diffraction angles 2θ±0.2 of 8.41, 13.45, 17.59, 21.51, and 24.91 using Cu-Kα radiation.*

*85. The method according to claim 84, wherein the crystal form is crystal form A.*

*86. The method according to claim 85, wherein the crystal form A has the powder X-ray diffraction spectrum comprising characteristic peaks at diffraction angles 2θ±0.2 of 7.60, 8.51, 13.52, 14.48, 15.23, 15.99, 16.82, and 21.91 using Cu-Kα radiation.*

*87. The method according to claim 86, wherein the crystal form A has the powder X-ray diffraction spectrum comprising characteristic peaks at diffraction angles 2θ±0.2 of 7.60, 8.51, 11.80, 12.38, 13.52, 14.48, 15.23, 15.99, 16.10, 16.82, 21.91, 22.57, 24.29, and 24.47 using Cu-Kα radiation.*

*88. The method according to claim 87, wherein the crystal form A has the powder X-ray diffraction spectrum comprising characteristic peaks at diffraction angles 2θ±0.2 of 7.60, 8.51, 11.80, 12.38, 13.52, 13.73, 14.48, 15.23, 15.99, 16.10, 16.82, 16.99, 17.35, 18.24, 20.82, 21.57, 21.91, 22.57, 22.76, 22.88, 24.29, 24.47, 25.24, 25.90, 27.23 and 27.71 using cu-Kα radiation.*

*89. The method according to claim 88, wherein the crystal form A has the powder X-ray diffraction spectrum comprising characteristic peaks at diffraction angles 2θ±0.2 of 7.60, 8.51, 10.37, 11.16, 11.80, 12.38, 12.89, 13.52, 13.73, 14.03, 14.48, 15.23, 15.99, 16.10, 16.43, 16.82, 16.99, 17.35, 18.24, 18.92, 19.17, 20.68, 20.82, 21.57, 21.91, 22.57, 22.76, 22.88, 23.53, 23.68, 24.00, 24.29, 24.47, 24.91, 25.24, 25.72, 25.90, 27.23, 27.74 and 35.63 using Cu-Kα radiation.*

*90. The method according to claim 85, wherein the leukemia is selected from the group consisting of chronic myeloid leukemia, acute myeloid leukemia and mixed lineage leukemia.*

*91. The method according to claim 85, wherein the lymphoma is non-Hodgkin's lymphoma, diffuse large B-cell lymphoma, or follicular lymphoma.*

*92. The method according to claim 91, wherein the lymphoma is non-Hodgkin's lymphoma.*

*93. The method according to claim 91, wherein the lymphoma is diffuse large B-cell lymphoma.*

*94. The method according to claim 91, wherein the lymphoma is follicular lymphoma.*

*95. The method according to claim 85, wherein the tumor or cancer is an ovarian tumor of an ovarian cancer.*

*96. The method according to claim 84, wherein the crystal form is crystal form B.*

*97. The method according to claim 96, wherein the crystal form B has the powder X-ray diffraction spectrum comprising characteristic peaks at diffraction angles 2θ±0.2 of 6.31, 10.99, 12.07, 14.56, 17.94, 19.13, 21.48, and 24.15 using Cu-Kα radiation.*

*98. The method according to claim 97, wherein the crystal form B has the powder X-ray diffraction spectrum comprising characteristic peaks at diffraction angles 2θ±0.2 of 6.31, 7.24, 10.99, 12.07, 14.56, 17.94, 19.13, 19.71, 21.48, 24.15, 27.10 and 28.83 using Cu-Kα radiation.*

*99. The method according to claim 98, wherein the crystal form B has the powder X-ray diffraction spectrum comprising characteristic peaks at diffraction angles 2θ±0.2 of 6.31, 7.24, 8.92, 10.38, 10.99, 12.07, 14.56, 15.10, 17.94, 19.13, 19.71, 21.48, 24.15, 26.52, 27.10, and 28.83 using Cu-Kα radiation.*

*100. The method according to claim 99, wherein the crystal form B has the powder X-ray diffraction spectrum comprising characteristic peaks at diffraction angles 2θ±0.2 of 6.31, 7.24, 8.92, 10.38, 10.99, 12.07, 14.56, 15.10, 16.36, 17.29, 17.94, 19.13, 19.71, 21.12, 21.48, 22.59, 24.15, 25.45, 26.28, 26.52, 27.10, 28.83, 30.07, 31.37, 32.56, 33.65, 34.64, 36.09, 37.13 and 40.04 using Cu-Kα radiation.*

*101. The method according to claim 96, wherein the leukemia is selected from the group consisting of chronic myeloid leukemia, acute myeloid leukemia and mixed lineage leukemia.*

*102. The method according to claim 96, wherein the lymphoma is non-Hodgkin's lymphoma, diffuse large B-cell lymphoma, or follicular lymphoma.*

*103. The method according to claim 102, wherein the lymphoma is non-Hodgkin's lymphoma.*

*104. The method according to claim 102, wherein the lymphoma is diffuse large B-cell lymphoma.*

*105. The method according to claim 102, wherein the lymphoma is follicular lymphoma.*

*106. The method according to claim 96, wherein the tumor or cancer is an ovarian tumor or an ovarian cancer.*

*107. The method according to claim 84, wherein the crystal form is crystal form C.*

*108. The method according to claim 107, wherein the crystal form C has the powder X-ray diffraction spectrum comprising characteristic peaks at diffraction angles 2θ±0.2 of 7.40, 8.62, 9.49, 12.32, 13.39, 15.52, and 22.78 using Cu-Kα radiation.*

*109. The method according to claim 108, wherein the crystal form C has the powder X-ray diffraction spectrum comprising characteristic peaks at diffraction angles 2θ±0.2 of 7.40, 8.62, 9.49, 12.32, 13.39, 15.52, 19.15, 19.17, 21.42 and 22.78 using Cu-Kα radiation.*

*110. The method according to claim 109, wherein the crystal form C has the powder X-ray diffraction spectrum comprising characteristic peaks at diffraction angles 2θ±0.2 of 7.40, 8.62, 9.49, 9.96, 12.32, 13.39, 14.21, 15.52, 17.67, 18.28, 19.15, 19.17, 21.42, 22.78, 24.74, and 25.34 using Cu-Kα radiation.*

*111. The method according to claim 110, wherein the crystal form C has the powder X-ray diffraction spectrum comprising characteristic peaks at diffraction angles 2θ±0.2 of 7.40, 8.62, 9.49, 9.96, 11.12, 12.32, 13.39, 14.21, 14.85, 15.52, 16.50, 17.67, 18.28, 19.15, 19.17, 20.06, 20.80, 21.42, 21.89, 22.20, 22.78, 23.41, 24.74, 25.34, 26.70, 27.38, 28.64, 29.63, 30.20 and 31.15 using Cu-Kα radiation.*

*112. The method according to claim 107, wherein the leukemia is selected from the group consisting of chronic myeloid leukemia, acute myeloid leukemia and mixed lineage leukemia.*

*113. The method according to claim 107, wherein the lymphoma is non-Hodgkin's lymphoma, diffuse large B-cell lymphoma, or follicular lymphoma.*

*114. The method according to claim 113, wherein the lymphoma is non-Hodgkin's lymphoma.*

*115. The method according to claim 113, wherein the lymphoma is diffuse large B-cell lymphoma.*

*116. The method according to claim 113, wherein the lymphoma is follicular lymphoma.*

*117. The method according to claim 107, wherein the tumor or cancer is an ovarian tumor or an ovarian cancer.*

*118. The method according to claim 84, wherein the crystal form is crystal form D.*

*119. The method according to claim 118, wherein the crystal form D has the powder X-ray diffraction spectrum comprising characteristic peaks at diffraction angles 2θ±0.2 of 8.41, 8.85, 13.45, 15.15, 17.59, 17.68, 21.51, 24.91, and 27.11 using Cu-Kα radiation.*

*120. The compound according to claim 119, wherein the crystal form D has the powder X-ray diffraction spectrum comprising characteristic peaks at diffraction angles 2θ±0.2 of 8.41, 8.85, 11.38, 12.18, 13.45, 15.15, 16.73, 17.59, 17.68, 20.45, 21.51, 22.72, 24.53, 24.91 and 27.11 using Cu-Kα radiation.*

*121. The compound according to claim 120, wherein the crystal form D has the powder X-ray diffraction spectrum comprising characteristic peaks at diffraction angles 2θ±0.2 of 8.41, 8.85, 11.38, 12.18, 13.45, 14.40, 15.15, 16.73, 17.59, 17.68, 18.42, 20.45, 21.15, 21.51, 22.11, 22.72, 24.03, 24.53, 24.91, 25.54, 26.54, 27.11, 27.61, and 29.04 using Cu-Kα radiation.*

*122. The method according to claim 121, wherein the crystal form D has the powder X-ray diffraction spectrum comprising characteristic peaks at diffraction angles 2θ±0.2 of 8.41, 8.85, 10.15, 11.38, 12.18, 13.45, 14.40, 15.15, 16.73, 17.59, 17.68, 18.42, 18.91, 19.22, 20.45, 21.15, 21.51, 22.11, 22.72, 24.03, 24.53, 24.91, 25.54, 26.54, 27.11, 27.61, 29.04, 30.49, 31.31, 33.00, 33.88, 35.52, 37.53, 40.46, 41.36, 42.40 and 44.02 using Cu-Kα radiation.*

*123. The method according to claim 118, wherein the leukemia is selected from the group consisting of chronic myeloid leukemia, acute myeloid leukemia and mixed lineage leukemia.*

*124. The method according to claim 118, wherein the lymphoma is non-Hodgkin's lymphoma, diffuse large B-cell lymphoma, or follicular lymphoma.*

*125. The method according to claim 124, wherein the lymphoma is non-Hodgkin's lymphoma.*

*126. The method according to claim 124, wherein the lymphoma is diffuse large B-cell lymphoma.*

*127. The method according to claim 124, wherein the lymphoma is follicular lymphoma.*

*128. The method according to claim 118, wherein the tumor or cancer is an ovarian tumor or an ovarian cancer.*

* * * * *